US012285766B2

(12) United States Patent
Henley

(10) Patent No.: US 12,285,766 B2
(45) **Date of Patent: *Apr. 29, 2025**

(54) ELECTRO-IONIC MASK DEVICES FOR IMPROVED PROTECTION FROM AIRBORNE BIOPATHOGENS

(71) Applicant: Julian Henley, New Orleans, LA (US)

(72) Inventor: Julian Henley, New Orleans, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/438,694

(22) Filed: Feb. 12, 2024

(65) Prior Publication Data

US 2024/0181469 A1 Jun. 6, 2024

Related U.S. Application Data

(63) Continuation of application No. 18/368,442, filed on Sep. 14, 2023, now Pat. No. 12,017,232, and a (Continued)

(51) Int. Cl.
*B03C 3/32* (2006.01)
*A61L 9/22* (2006.01)
(Continued)

(52) U.S. Cl.
CPC .................. *B03C 3/32* (2013.01); *A62B 7/10* (2013.01); *A62B 23/025* (2013.01); *B03C 3/025* (2013.01);
(Continued)

(58) Field of Classification Search
CPC ....... A62B 23/02; A62B 23/025; A62B 23/00; A62B 7/10; B03C 3/361; B03C 3/363;
(Continued)

(56) References Cited

U.S. PATENT DOCUMENTS 5,368,816 A 11/1994 Detzer
5,788,930 A 8/1998 McMurray
(Continued)

FOREIGN PATENT DOCUMENTS

CN 103585844 B 6/2015
JP 2016501589 A 1/2016
(Continued)

OTHER PUBLICATIONS

Notice of Allowance, U.S. Appl. No. 17/911,372, dated Jan. 23, 2024, 21 pgs.

(Continued)

*Primary Examiner* — Joseph D. Boecker
*Assistant Examiner* — Brian T Khong
(74) *Attorney, Agent, or Firm* — Polsinelli PC

(57) ABSTRACT

Aspects of the present disclosure include a protective mask to be worn over a nose and mouth of a wearer to protect the wearer from hazards in surrounding ambient air. The mask includes a mask portion, an airway, and an ionization filter. The mask portion includes an interior that extends over the nose and mouth of the wearer. The airway extends between the interior of the mask portion and the surrounding ambient air. The ionization filter includes an emitter within a portion of the airway, and a collector plate radially encompassing the emitter and defining at least a portion of the airway. The collector plate is electrically connected to at least first and second conductive porous filters. The first and second conductive porous filters and the collector plate collectively form at least a portion of a Faraday cage that encapsulates the emitter.

30 Claims, 49 Drawing Sheets

Related U.S. Application Data continuation of application No. PCT/US2022/071174, filed on Mar. 15, 2022, which is a continuation-in-part of application No. PCT/US2021/022386, filed on Mar. 15, 2021, said application No. 18/368,442 is a continuation of application No. PCT/US2022/071175, filed on Mar. 15, 2022, which is a continuation-in-part of application No. PCT/US2021/022386, filed on Mar. 15, 2021.

(60) Provisional application No. 63/310,810, filed on Feb. 16, 2022, provisional application No. 63/230,273, filed on Aug. 6, 2021, provisional application No. 63/113,598, filed on Nov. 13, 2020, provisional application No. 63/063,968, filed on Aug. 11, 2020, provisional application No. 63/044,768, filed on Jun. 26, 2020, provisional application No. 63/043,424, filed on Jun. 24, 2020, provisional application No. 63/027,746, filed on May 20, 2020, provisional application No. 62/988,991, filed on Mar. 13, 2020.

(51) Int. Cl.
| | | |
|---|---|---|
| *A62B 7/10* | (2006.01) | |
| *A62B 23/02* | (2006.01) | |
| *B03C 3/02* | (2006.01) | |
| *B03C 3/36* | (2006.01) | |
| *B03C 3/41* | (2006.01) | |
| *B03C 3/82* | (2006.01) | |
| *B64U 10/14* | (2023.01) | |
| *G01T 1/169* | (2006.01) | |
| *G21F 9/02* | (2006.01) | |
| *B64U 101/00* | (2023.01) | |

(52) U.S. Cl.
CPC .............. *B03C 3/363* (2013.01); *B03C 3/41* (2013.01); *B03C 3/82* (2013.01); *B64U 10/14* (2023.01); *G01T 1/169* (2013.01); *G21F 9/02* (2013.01); *A61L 9/22* (2013.01); *A61L 2209/14* (2013.01); *B03C 2201/30* (2013.01); *B64U 2101/00* (2023.01)

(58) Field of Classification Search
CPC ......... B03C 3/365; B03C 3/366; B03C 3/368; B03C 3/38; B03C 3/383; B03C 3/40; B03C 3/41; B03C 3/43; B03C 3/45; B03C 3/82; B03C 3/84; B03C 3/49; B03C 3/12; B03C 2201/10; A61L 2/0017; A61L 2/022; A61L 2/14; A61L 2/183; A61L 2/202; A61L 9/22

See application file for complete search history.

(56) References Cited

U.S. PATENT DOCUMENTS

| | | | |
|---|---|---|---|
| 7,392,806 B2 | 7/2008 | Yuen et al. | |
| 8,292,991 B2 | 10/2012 | Friday et al. | |
| 8,318,084 B2 | 11/2012 | Johnson | |
| 11,559,708 B2 | 1/2023 | Zilberstein et al. | |
| 2003/0136408 A1* | 7/2003 | Henley | B03C 3/12 |
| | | | 128/206.13 |
| 2004/0216745 A1* | 11/2004 | Yuen | A62B 19/00 |
| | | | 128/205.27 |
| 2007/0163588 A1* | 7/2007 | Hebrank | A61M 16/0069 |
| | | | 128/205.29 |
| 2017/0136270 A1* | 5/2017 | Son | B01D 53/32 |
| 2021/0346732 A1* | 11/2021 | Tu | A62B 23/02 |
| 2022/0330630 A1 | 10/2022 | Vandendorpe et al. | |
| 2024/0293686 A1 | 9/2024 | Henley | |

FOREIGN PATENT DOCUMENTS

| | | |
|---|---|---|
| RU | 201474 U1 | 12/2020 |
| WO | WO 2014/082120 A1 | 6/2014 |
| WO | WO 2021/184011 A1 | 10/2021 |
| WO | WO 2021/207098 A1 | 10/2021 |
| WO | WO 2022/198214 A1 | 9/2022 |

OTHER PUBLICATIONS

Extended European Search Report, EP21768625.2, dated Mar. 21, 2024, 8 pgs.
Non-Final Office Action, U.S. Appl. No. 17/911,374, dated May 21, 2024, 30 pgs.
International Search Report and Written Opinion, issued in connection with International Application No. PCT/US2024/018254, dated Aug. 7, 2024, 24 pgs.
EPO, Extended European Search Report, EP22772374.9, dated Sep. 30, 2024, 11 pgs.

* cited by examiner

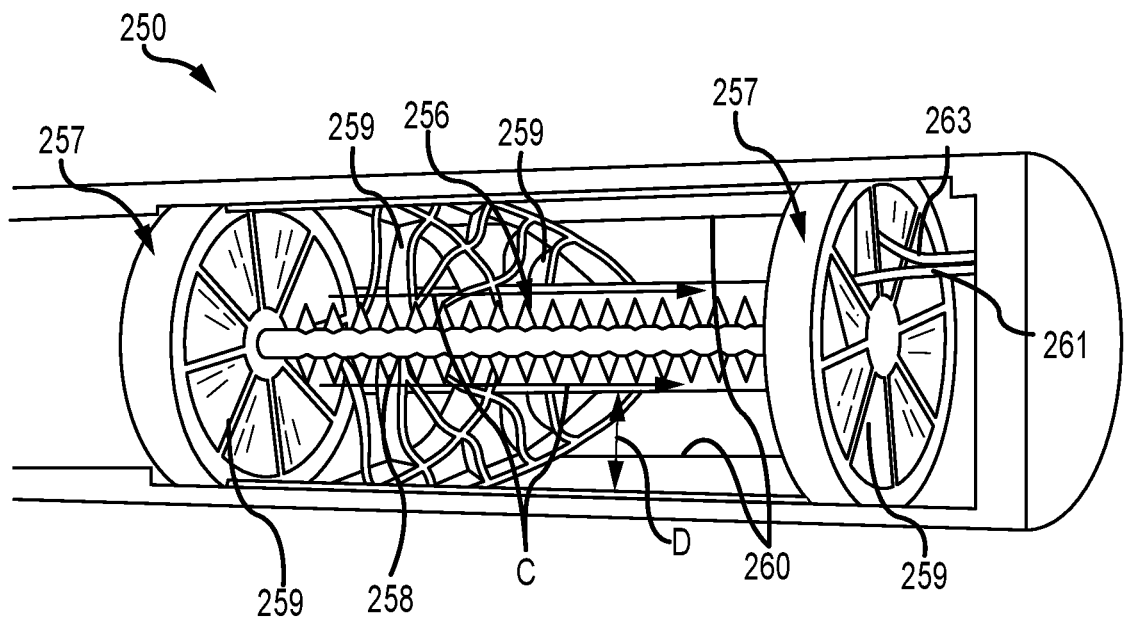
FIG.9B
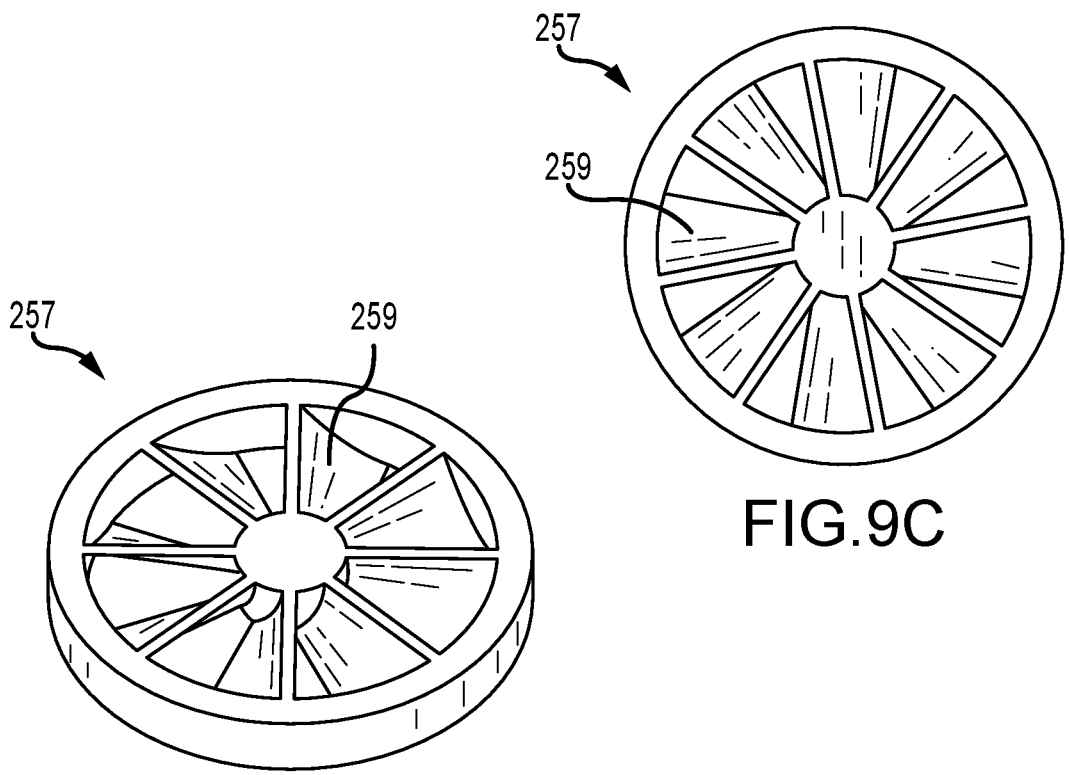
FIG.9C
FIG.9D

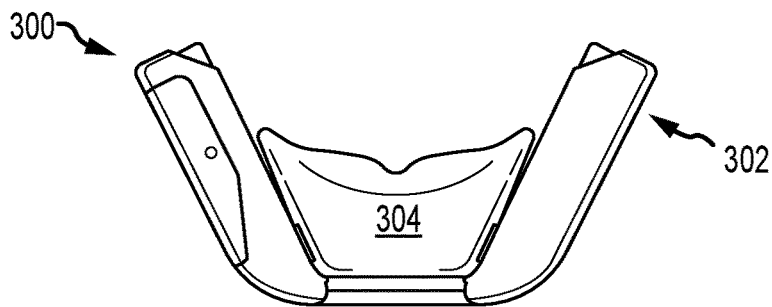
FIG.39C
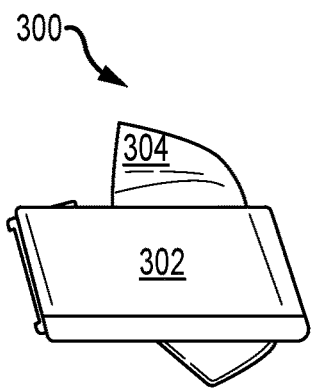 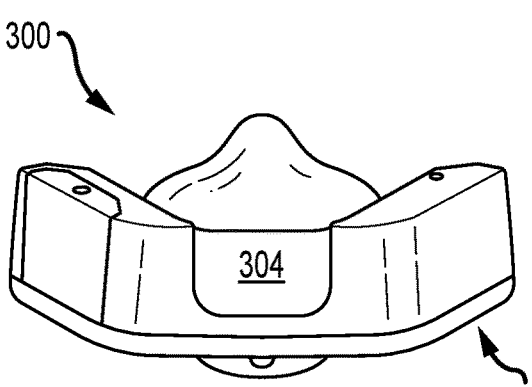 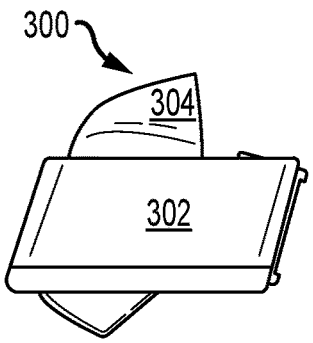
FIG.39D  FIG.39E  FIG.39F
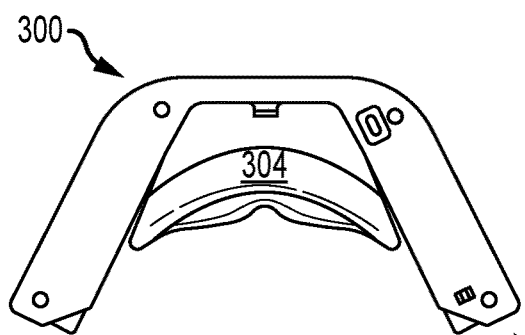
FIG.39G
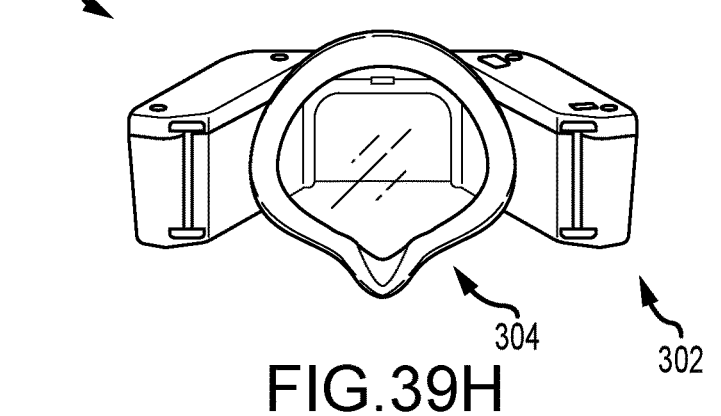
FIG.39H

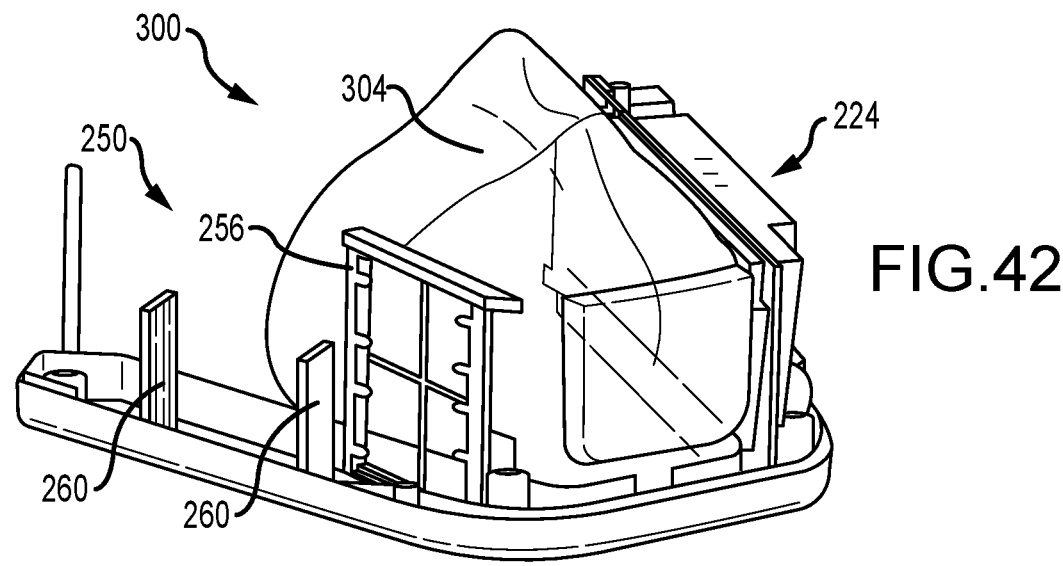
FIG.42
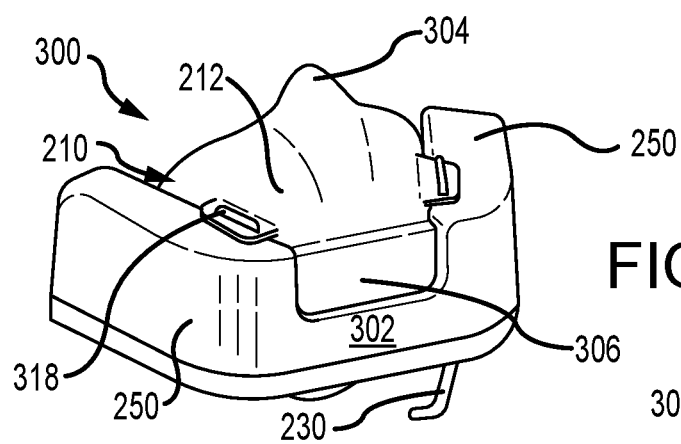
FIG.43A
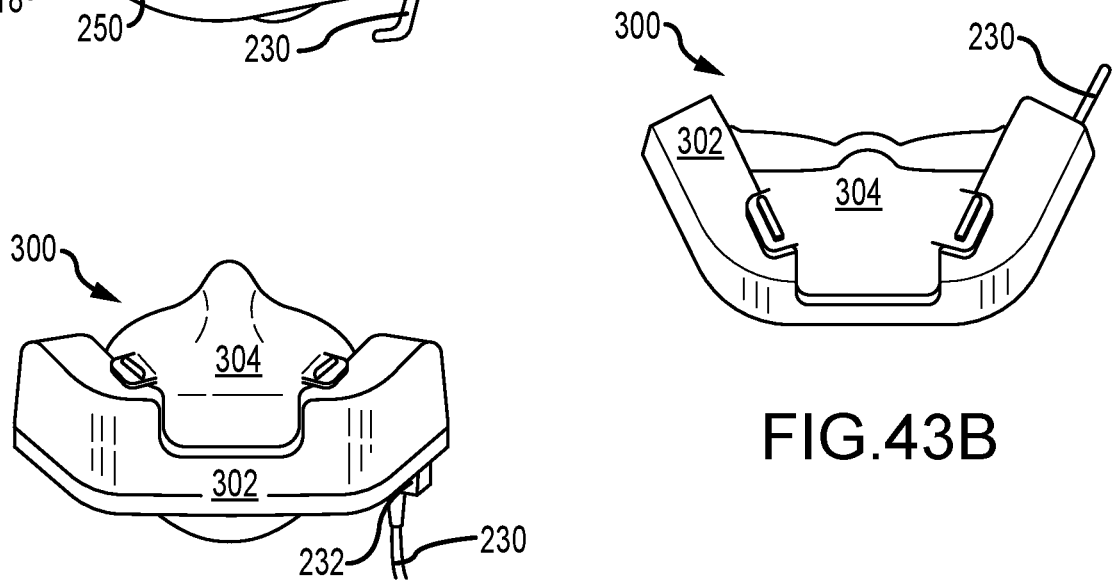
FIG.43B
FIG.43C

ELECTRO-IONIC MASK DEVICES FOR IMPROVED PROTECTION FROM AIRBORNE BIOPATHOGENS

CROSS REFERENCE TO RELATED APPLICATION

This application is a continuation of U.S. patent application Ser. No. 18/368,442, filed Sep. 14, 2023, which application is a continuation of International Patent Application No. PCT/US2022/071174, filed Mar. 15, 2022, which application is a continuation-in-part of International Patent Application No. PCT/US2021/022386 filed on Mar. 15, 2021, which application claims the benefit of priority to U.S. Provisional Patent Appln. No. 62/988,991 filed on Mar. 13, 2020, U.S. Provisional Patent Appln. No. 63/027,746 filed on May 20, 2020, U.S. Provisional Patent Appln. No. 63/043,424 filed on Jun. 24, 2020, U.S. Provisional Patent Appln. No. 63/044,768 filed on Jun. 26, 2020, U.S. Provisional Patent Appln. No. 63/063,968 filed on Aug. 11, 2020, and U.S. Provisional Patent Appln. No. 63/113,598 filed on Nov. 13, 2020.

The International Patent Application No. PCT/US2022/071174, filed Mar. 15, 2022, claims the benefit of priority to U.S. Provisional Patent Appln. No. 63/230,273 filed on Aug. 6, 2021, and U.S. Provisional Patent Appln. No. 63/310,810 filed on Feb. 16, 2022.

U.S. patent application Ser. No. 18/368,442 is also a continuation of International Patent Application No. PCT/US2022/071175, filed Mar. 15, 2022, which application is a continuation-in-part of International Patent Application No. PCT/US2021/022386, filed Mar. 15, 2021, which application claims the benefit of priority to U.S. Provisional Patent Appln. No. 62/988,991 filed on Mar. 13, 2020, U.S. Provisional Patent Appln. No. 63/027,746 filed on May 20, 2020, U.S. Provisional Patent Appln. No. 63/043,424 filed on Jun. 24, 2020, U.S. Provisional Patent Appln. No. 63/044,768 filed on Jun. 26, 2020, U.S. Provisional Patent Appln. No. 63/063,968 filed on Aug. 11, 2020, and U.S. Provisional Patent Appln. No. 63/113,598 filed on Nov. 13, 2020.

The International Patent Application No. PCT/US2022/071175, filed Mar. 15, 2022, claims the benefit of priority to U.S. Provisional Patent Appln. No. 63/230,273 filed on Aug. 6, 2021, and U.S. Provisional Patent Appln. No. 63/310,810 filed on Feb. 16, 2022.

The entirety of each of the above-referenced applications is incorporated by reference herein.

This application also incorporates by reference in its entirety U.S. Pat. No. 6,901,930 filed on Oct. 28, 2002.

FIELD OF THE INVENTION

This application relates to devices and methods for improved protection from airborne biopathogens. In particular, this application relates to wearable devices and methods of using wearable devices for particle capture and deactivation.

BACKGROUND OF THE INVENTION

It is difficult for patients and practitioners to control the transmission of airborne viruses and infections. Examples of such infections include seasonal flu, common colds, and measles, among others. Recently, COVID-19 is thought to have a component of airborne transmission and cross infection. Some researchers believe that under normal circumstances, when small airborne particles enter the lungs, some of them may directly bypass the airway defensive system which is made up of mucous membranes in the nasal and oral cavity as well as the bronchial tree. These particles may enter the distal alveolus where they can rapidly begin contacting cells of the internal organ. Such penetration of the distal alveolus is thought to be confined to the smaller particles as the larger particles are trapped by the body's own filtration system.

Although the exact mechanism of viral transmission remains a point of controversy, some investigators lean towards the fact that viral transmission occurs through touching and then movement of the fingers to enter mucous membranes where the virus can implant itself. This theory is based on the idea that the human cough sprays larger droplets that can be effectively precipitated or filtered and do not necessarily need to be inhaled.

The exact mechanism of transmission remains controversial, but some investigators postulate that the small particles penetrating the distant alveolus is a significant modality of transmission. It is quite possible that the salivary droplets and mucous droplets that contain the virus and exit an infected patient as a cough mist partially evaporate or settle onto a surface. Such micro-droplets get smaller via evaporation and may become airborne again in the proximity of the enclosed space or circulating air system such as in buildings and airplanes.

The airborne transmissibility is predicated on the functional viability of the virus outside of the body in the air, in buildings, or airplane ventilators. If a viral particle remains viable outside of the body for a period of time, it is likely to be present as a small airborne particle that infects the body via distal alveolus and that bypass the oral and nasal mucous membranes that through evolution have developed defense mechanisms against serendipitous infection.

Just like in small particle drug delivery systems, the distal alveolus remains the undefended portal to the blood stream. The same aspect of airborne COVID-19 and the fact that it has extended functional survivability outside of the body in air and surfaces raises another important limitation of existing filtration technology like the N95 mask. This limitation exists because a filter entrapment of viral particles within the mask can potentially make the mask a secondary reservoir of live virus particles near the airway, and changes in evaporative status can seed the trapped viruses back into the respiratory system. It is desirable for a mask capable of adequate entrapment of viral particles and droplets to have a virus kill technology in real-time, not via occasional and inconsistent mask cleaning protocols. It may also be desirable to kill viruses in the respiratory tract.

SUMMARY OF THE INVENTION

Aspects of the present disclosure include a protective mask to be worn over a nose and mouth of a wearer to protect the wearer from hazards in surrounding ambient air. The mask includes a mask portion, an airway, and an ionization filter. The mask portion includes an interior that extends over the nose and mouth of the wearer. The airway extends between the interior of the mask portion and the surrounding ambient air. The ionization filter includes an emitter within a portion of the airway, and a collector plate radially encompassing the emitter and defining at least a portion of the airway. The collector plate is electrically connected to at least first and second conductive porous filters. The first and second conductive porous filters and the collector plate collectively form at least a portion of a Faraday cage that encapsulates the emitter.

In one version of the protective mask, the Faraday cage may also encapsulates circuitry within the ionization filter.

In one version of the protective mask, the porous filters may include a non-conductive fibrous mesh infused with electrically conductive materials, including conductive wires.

In one version of the protective mask, the porous filters may include a mesh of conductive materials without a non-conductive mesh. For example, the mesh of conductive material may include at least one of alloys or oxides containing at least one of nickel, chromium, manganese, cobalt, iron, copper, platinum, silver, rhodium, cerium or combinations thereof. The porous filters may assist in the decomposition of ozone.

In one version of the protective mask, the Faraday cage further includes an end cap. The electrically conductive materials used to form the end cap of the Faraday cage may include at least one of copper, aluminum, or steel alloys.

In one version of the protective mask, the porous filters may have an electrically conductive mesh having a pore size at least one of the following: between 1 μm and 5 mm, between 10 μm and 2.5 mm, between 100 μm and 2.0 mm, and between 1 mm and 2 mm.

In one version of the protective mask, first and last electrodes of the emitter may be axially spaced farther apart from respective porous filters than their radial distance to the collector plate.

In one version of the protective mask, the airway includes an opening into the interior of the mask, and the opening may include a fluid filter configured to reduce the amount of, or prevent, fluids from the wearer entering the ionization filter. The fluid filter may include at least one of alloys or oxides containing at least one of nickel, chromium, manganese, cobalt, iron, copper, platinum, silver, rhodium, or cerium to assist in the decomposition of ozone.

In one version of the protective mask, the emitter may be housed at an axial center of the collector plate. The emitter may be inserted into, or removed from, the collector plate along an axial direction for cleaning or replacement.

In one version of the protective mask, turbulence vanes are located within the airway and confines of the Faraday cage to increase the incidence of particles interfacing with the emitter.

In one version of the protective mask, the airway leading to one or both open ends of the portion of the airway defined by the collector plate is a spiral. The spiral may be in the form of a spiral insert in the ionization filter. The spiral may be in the form of a spiral pathway defined in an outer housing of the ionization filter.

In one version of the protective mask, the airway leading to each open end of the portion of the airway respectively defined by the collector plate may be a spiral, a first spiral being clockwise and a second spiral being counterclockwise.

In one version of the protective mask, the airway leading to one or both open ends of the portion of the airway defined by the collector plate may be a spiral, and the spiral may be coated with, or at least partially formed of, at least one alloy or oxide containing at least one of nickel, chromium, manganese, cobalt, iron, copper, platinum, silver, rhodium, or cerium to assist in the decomposition of ozone.

In one version of the protective mask, the airway leading to one or both open ends of the portion of the airway defined by the collector plate may be a spiral with a total minimum distance of at least one of: greater than or equal to about 5 cm, greater than or equal to about 10 cm, greater than or equal to about 15 cm, greater than or equal to about 20 cm; or greater than or equal to about 22 cm.

In one version of the protective mask, the airway leading to one or both open ends of the portion of the airway defined by the collector plate may be a zigzag pathway formed by opposed and offset radially inward extending baffles.

In one version of the protective mask, the airway leading to one or both open ends of the portion of the airway defined by the collector plate may be a zigzag pathway formed by opposed and offset radially inward extending baffles, and the zigzag pathway may be coated with, or at least partially formed of, at least one alloy or oxide containing at least one of nickel, chromium, manganese, cobalt, iron, copper, platinum, silver, rhodium, or cerium to assist in the decomposition of ozone.

In one version of the protective mask, the airway leading to one or both open ends of the portion of the airway defined by the collector plate may be a zigzag pathway formed by opposed and offset radially inward extending baffles, and the zigzag pathway may have a total minimum distance of at least one of: greater than or equal to about 5 cm, greater than or equal to about 10 cm, greater than or equal to about 15 cm, greater than or equal to about 20 cm; or greater than or equal to about 22 cm.

Aspects of the present disclosure include a ventilator system for treating a patient. The system includes an endotracheal tube, an inlet tube and an outlet tube in fluid communication with the endotracheal tube, a ventilator, a first ionization filter, an ozone sensor, and a controller. The endotracheal tube is configured to be intubated into the patient. The ventilator is in fluid communication with the inlet and outlet tubes and configured to apply positive pressure to the inlet tube and a negative pressure to the outlet tube. At least the ventilator, inlet tube, and the endotracheal tube define an inspiration pathway and at least the ventilator, outlet tube, and the endotracheal tube defining an expiration pathway. The first ionization filter is positioned along the inspiration pathway. The ozone sensor is in communication with the inspiration pathway. The controller is in communication with the ozone sensor and configured to cause the first ionization filter to generate a predetermined amount of ozone.

In one version of the ventilator system, the ionization filter generates at least ozone and eliminates particles. The ionization filter includes an emitter and a collector plate. For example, the ionization filter includes: an emitter within a portion of the inspiration pathway; and a collector plate radially encompassing the emitter and defining at least a portion of the inspiration pathway. The ionization filter may further include a Faraday cage that encapsulates the emitter and collector plate.

In one version of the ventilator system, the expiration pathway also includes a second ionization filter with an emitter and a collector plate. Also, the expiration pathway may pass through an ozone decomposition device downstream of the second ionization filter. The ozone decomposition device may include at least one of alloys or oxides containing at least one of nickel, chromium, manganese, cobalt, iron, copper, platinum, silver, rhodium, or cerium to assist in the decomposition of ozone before exhausting into ambient surroundings. The ventilator system may further include an ozone sensor in communication with the expiration pathway and downstream of the ozone decomposition device, wherein the controller controls the second ionization filter such that ozone concentration downstream of the ozone decomposition device is less than 0.05 ppm.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 9B is a perspective view of the version of the ionization filter of FIG. 9A employing spiraled spacers.

FIG. 9C is a front view of a spiraled spacer employed in the ionization filter of FIG. 9B.

FIG. 9D is an isometric view of the spiraled spacer of FIG. 9C.

FIG. 39C is a top view of the electro-ionic device from FIG. 39A.

FIG. 39D is a left-side view of the electro-ionic device from FIG. 39A.

FIG. 39E is a top, front perspective view of the electro-ionic device from FIG. 39A.

FIG. 39F is a right-side view of the electro-ionic device from FIG. 39A.

FIG. 39G is a bottom view of the electro-ionic device from FIG. 39A.

FIG. 39H is a bottom, back perspective view of the electro-ionic device from FIG. 39A.

FIG. 42 is a perspective view of the electro-ionic device from FIG. 39A showing some components thereof.
FIG. 43A is a perspective view of an electro-ionic device according to an exemplary embodiment of the present disclosure.
FIG. 43B is a top view of the electro-ionic device from FIG. 43A.
FIG. 43C is a front view of the electro-ionic device from FIG. 43A.

DETAILED DESCRIPTION

Figure 1:
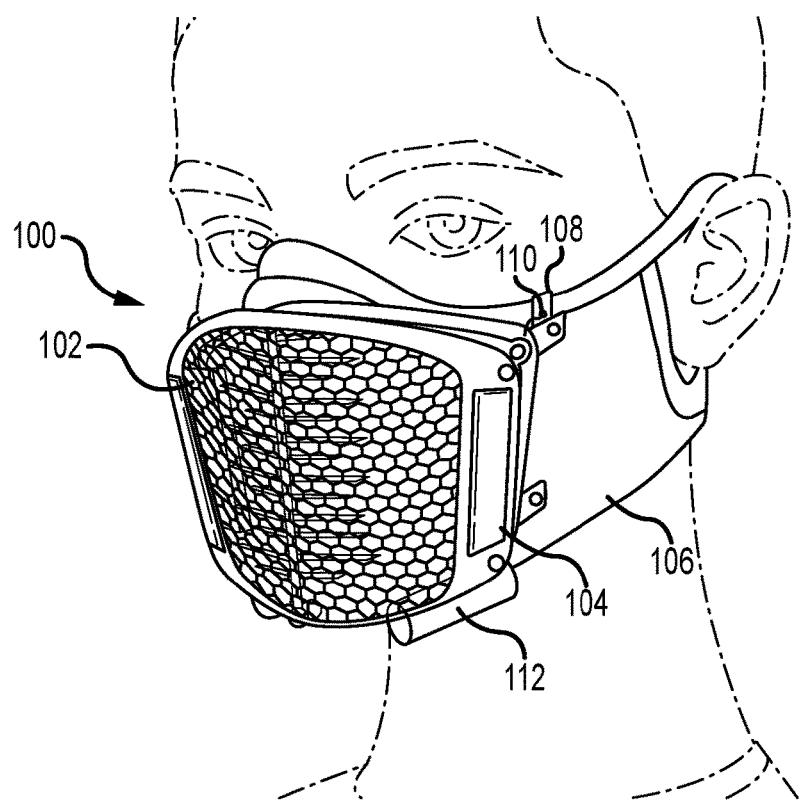
FIG. 1 is a perspective view of an electro-ionic device according to an exemplary embodiment of the present disclosure.
Figure 2:
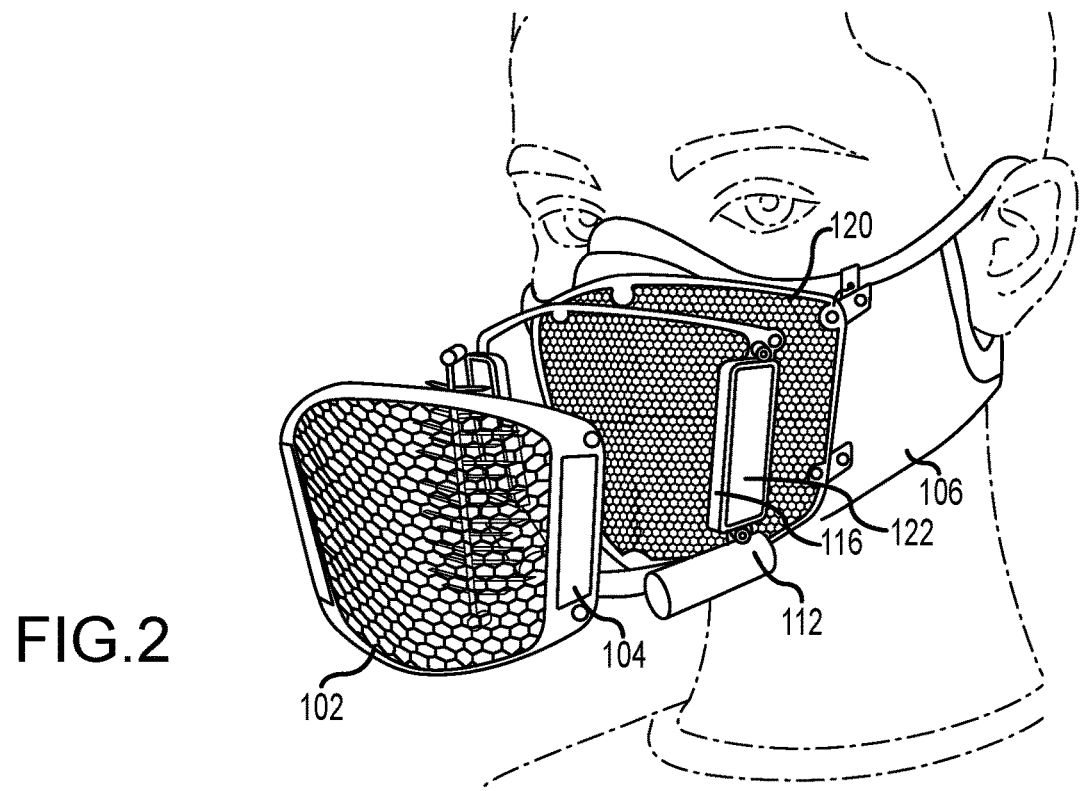
FIG. 2 is a perspective exploded view of the electro-ionic device from FIG. 1.
Figure 3:
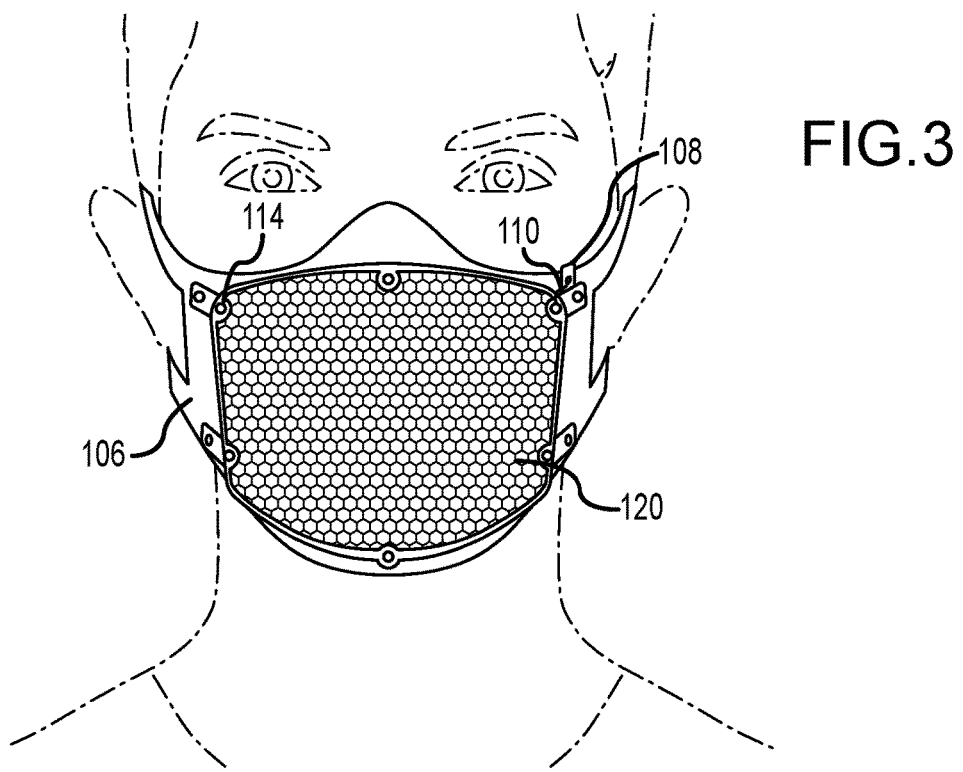
FIG. 3 is a front view the electro-ionic device from FIG. 1 showing some of the components thereof.
Figure 4:
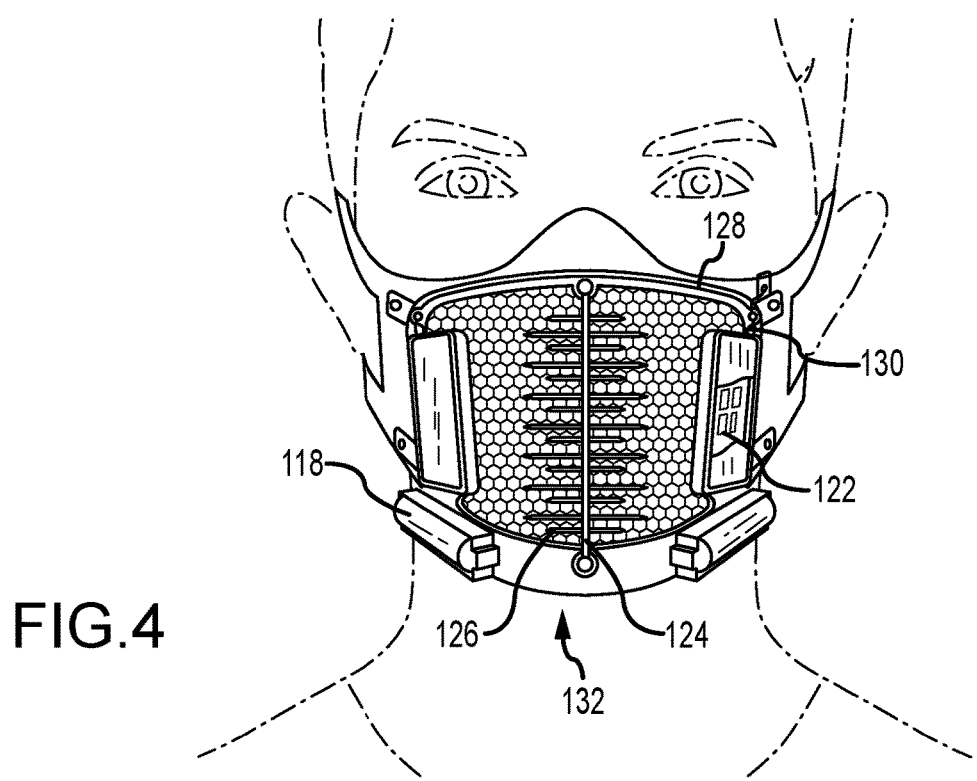
FIG. 4 is a front view the electro-ionic device from FIG. 1 showing some of the components thereof.
Figure 5:
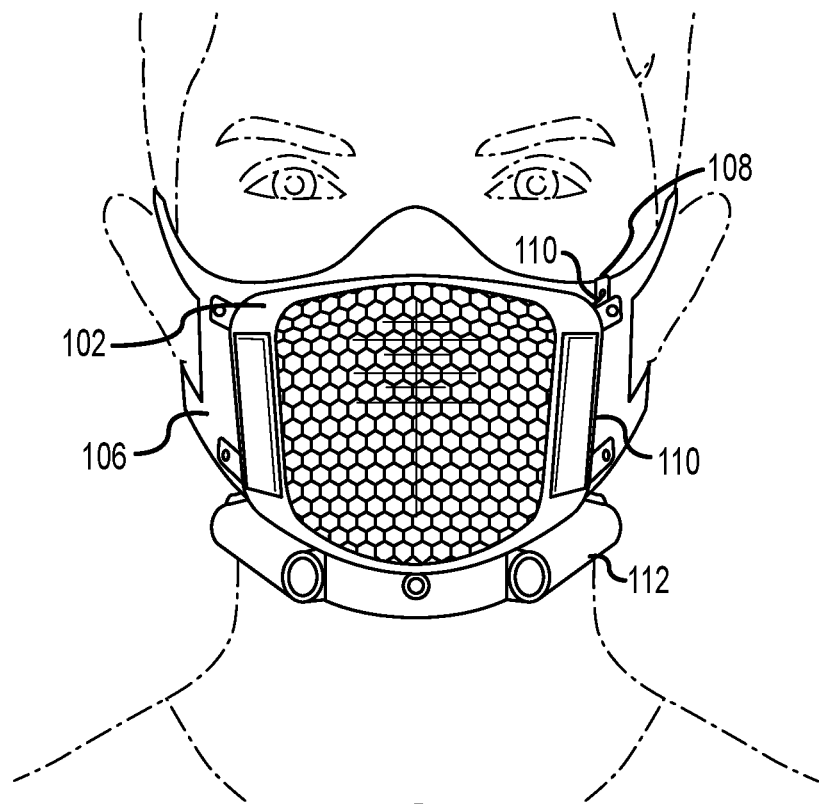
FIG. 5 is a front view the electro-ionic device from FIG. 1.

A portable and wearable electro-ionic device (e.g., electrostatic precipitator) is disclosed herein in a variety of embodiments and versions thereof. The portable and wearable electro-ionic device removes airborne particles from the air stream. For example, the electro-ionic device is configured to remove pathogens, toxins and other hazardous particles from an inspired air stream by virtue of electrostatic precipitation. Thus, in the age of COVID-19, the portable and wearable electro-ionic device and its electrostatic precipitation can remove from an inspired air stream droplets of saliva containing virus or virus particles that are airborne.

In some embodiments of the electro-ionic device described below, it will be understood that inspiration and/or expiration airflows within the electro-ionic device are substantially, if not completely, perpendicular to a strong electric field between an emitter and collector. Ideally, the emitter has sharp points to facilitate the rejection of electrons that in turn impart a charge onto airborne particles. As these charged airborne particles continue along their path within the electro-ionic device, the charged airborne particles are subjected to a strong electric field and thereby attracted to, and deposited on, the surface of the collector. The electric field between the emitter and the collector is generated from a battery supply and a step-up voltage module. Subjecting the airflow to this strong electric field is the underlying modality that removes the particles in real time from the air stream.

The electro-ionic devices disclosed herein have sufficient electrical power storage and performance set points so that each charge can maintain performance efficacy for at least 8 to 12 hours. The electro-ionic devices are configured to be sufficiently lightweight such that they can be worn for extended periods of time attached to the face without creating irritation or fatigue.

The electro-ionic devices employ servo control of the power utilization to maintain both a proper performance window in terms of particle removal as well as assures proper current utilization and duration of wearable power supply. The servo control adjusts the voltage and current use in real time on a continuous basis during operation to achieve these aims. In other words, a servo mechanism is used to control the power that flows between the emitter and collector of the ionization filter.

In the various embodiments, the circuitry of the electro-ionic device monitors the supply current and auto-adjusts the voltage to maintain a fixed parameter such that the voltage across the emitter will be at an optimal level to filter without excessive ozone levels. In some embodiments, the same effect can be obtained by setting the voltage as a function of elevation pressure.

The distance and geometry of the air path is a balance for at least some of the embodiments of the electro-ionic device disclosed herein. For example, as a consideration, as the airflow passage geometry is increasingly extended to result in a longer and more effective airflow path, the resulting greater surface of the collector would require lower power usage but increase the weight and size of the ionizer filter, plus increase the snorkel effect and dead space that would contribute to carbon dioxide retention.

As another consideration, increasingly reducing the gap between emitter and collector and creating a narrower airflow path could lower the necessary operational voltage, but increase airflow resistance, increase the weight of the material of the device, increase the potential for ion flow tunneling and sparking, and create manufacturing difficulties. By balancing these concerns, in some versions of the embodiments disclosed herein, the operational voltage for the ionizer filter will be between approximately 5 kV and approximately 15 kV, and preferably 6 kV to 11.5 kV for a distance between the tip of the emitter and collector of 15 mm, at sea level. For other embodiments, with a distance between the tip of the emitter and collector between approximately 10 mm and approximately 20 mm, the operational voltage for the ionizer filter will be between approximately 4 kV and approximately 20 kV, at sea level.

The embodiments of the electro-ionic disclosed herein are efficient high-performance protective devices that are portable, comfortable, and light enough for extended periods of time and capable of remaining operational for at least 8 to 12 hours on a single charge. Further, these embodiments offer an acceptable appearance plus a hydration port. Additionally, the configuration and visual transparency of the electro-ionic devices facilitate communication and even enhance communication by virtue of placement and amplification via Bluetooth microphone, which may be located within the mask of the electro-ionic device and, in some versions, in a plug of the hydration port. The numerous embodiments of the electro-ionic device illustrated in the above listed Figures make clear the features and capabilities of the electro-ionic device can come in a variety of configurations to facilitate wear ability, comfort, and mitigate restrictions to movement or work performance. Finally, the electro-ionic device works, having been tested at the Tulane BSLIII lab to demonstrate a 99.8% viral penetration reduction in the context of a COVID-19 aerosol study with COVID-19 aerosol concentrations at much higher levels than would ever be encountered in real life.

For a detailed discussion of the various embodiments disclosed herein, reference will now be made to the exemplary embodiments, which are illustrated in the accompanying drawings. Wherever possible, the same reference numbers will be used throughout the drawings to refer to the same or like parts.

An exemplary embodiment of an electro-ionic device 100 is shown in FIGS. 1-5. The device 100 may include a base layer or a filtrate layer 106 at an innermost position toward a user. The filtrate layer 106 may be comprised of a fibrous or porous medium such as cotton, polypropylene, nylon, polyester, wool, rayon, or combinations thereof. The filtrate layer 106 may include attachments such as strings or loops to fasten to a user's ears or to tie behind the user's head.

A finely-meshed negative grid 120 may be positioned outward from the filtrate layer 106 and, as will be discussed in more detail below, may function to help repel negatively charged particles. The negative grid 120 may be comprised of an electrical conductor such as stainless steel, or alloys or oxides containing nickel, chromium, manganese, cobalt, iron, copper, platinum, silver, rhodium, cerium or combinations thereof. The aforementioned non-exhaustive list of metals may assist in the decomposition of ozone. In addition, the negative grid 120 may be comprised of various metal foils and/or coated with one of the previously mentioned alloys. The negative grid 120 may be attached to the filtrate layer 106 with one or more tabs 114, such as four tabs 114. The tabs 114 may be comprised of the same material as the filtrate layer 106 and may hold the negative grid 120 closely thereto or the tabs 114 may function as standoffs having a rigid or semi-rigid construction providing a space between these layers. The negative grid 120 may be in electrical communication with a user contacting conductor 108 positioned on the filtrate layer 106 through a conductive wire 110. The user contacting conductor 108 may have a conductive surface on the inside of the filtrate layer 106 for contacting the user's skin and may include an adhesive for better adhesion thereto. As shown, the user contacting conductor 108 is an annular surface surrounding an outer reinforced portion of a loop of the filtrate layer 106. However, in other embodiments not shown, the contacting conductor 108 may be positioned around the ear loops or nose bridge or in several portions along the filtrate layer 106 or entirely along an outer perimeter of the filtrate layer 106. The filtrate layer 106 itself may be infused with electrically conductive materials including conductive wires comprising alloys or oxides containing nickel, chromium, manganese, cobalt, iron, copper, platinum, silver, rhodium, cerium, or combinations thereof.

A component layer 132 may be positioned outward from the negative grid 120. The component layer 132 includes a frame 128 which may be comprised of an insulating material and directly mounted to the negative grid 120 or spaced slightly apart using separate or built-in standoffs. The frame 128 may have a continuous outer surface defining an opening radially inward and may be configured to surround a respiration pathway such that all or most of the inspired and expired air in the respiration pathway flows through the opening. The frame 128 may house one or more electronics compartments 122, such as two electronics compartments positioned diametrically across from each other outside of a mouth-covering portion of the electro-ionic device 100, one or more battery compartments 112 positioned below the mouth-covering portion, and an emitter 124 positioned directly in front of the mouth-covering portion directly in a respiration pathway of a user. The tabs 114, frame 128, and other standoffs may keep the emitter 124 at least 0.5 mm, 1.0 mm, or 2.0 mm from the user's face. Each electronics compartment 122 may include one or more circuits and may further include a processor or controller. Each of the electronics compartments 122 may have a metallic housing with a collector plate 116 such as an outwardly facing conductive side which faces toward the emitter 124. In other embodiments the collector plate 116 may be separate from the electronics compartment 122. The collector plate 116 may be placed outside of the opening in the frame.

The emitter 124 may comprise a plurality of electrodes 126 that are oriented perpendicular to the respiration pathway. Each of the electrodes 126 may be oriented parallel with respect to one another. The electrodes 126 may be machined or laser cut and form multiple sharp stainless steel or other oxidation resistant conductive materials oriented toward the collector plates 116. In some embodiments, the emitter 124 may comprise steel wool having multiple sharp thin pointed endings. In some embodiments, the emitter 124 may comprise carbon nanotubes. A process of nanotube deposition upon a conductive steel grid or wire in presence of high voltage gradient may orient them in a substantially vertical fashion with suitable separations or spacing therebetween. Once the nanotubes have bonded to the surface of the underlying conducting wire or a wire grid, the emitter 124 may have improved performance at significant manufacturing savings as compared to building sharp points via machining or laser cutting production. Further, the tips of the electrodes 126 may have a metal coating to help decrease the electron workforce and improve the efficiency of electro-ionic device 100. Such coatings may include manganese, iridium, tantalum, and zinc, among others. Reducing the electron workforce may permit a reduction in the emitter voltage and thereby improve the viability of the underlying power source as well as the underlying components.

The battery compartments 112 may include one or more batteries 118. As shown, the electro-ionic device 100 includes two battery compartments 112 each housing a battery 118. The batteries 118 may include, for example, AA alkaline batteries, AAA alkaline batteries, or other alkaline batteries of various sizes. The batteries 118 may also include, for example, rechargeable batteries including NiCd, NiMH, or lithium ion, such as a set of 18650 lithium batteries. It may also be possible to replace the batteries 118 without need for removing the electro-ionic device 100 from the face of a user. The electro-ionic device 100 may be worn for extended period of time during workday and travel. As such, it may include batteries 118 having a functional capacity of at least 8 hours. The batteries may be operatively connected to the electronics compartment 122 to provide electrical power to various circuits. During use, these circuits may consume less than 1 watt at 24 volts, preferably they may consume 0.2 watt at 24 volts. One such circuit may include a battery monitoring circuit which may alert a user with either an audio, a visual, or a tactile alert when the batteries 118 become low.

The electronics compartment 122 may be operatively connected to a switch (not shown) for turning on and off the electro-ionic device 100. The electronics compartment 122 may also be connected to the emitter 124 via a conductive wire 130 routed under behind the frame 128, the negative grid 120, an acceleration grid 102, and one or more collector plates 116 which are operatively described in more detail below. The acceleration grid 102 and the collector plates 116 may be located in an outer layer farther outward with respect to the component layer 132. The acceleration grid 102 has substantially the same outer shape as the negative grid 120 and the frame 128, and similarly is positioned within the respiration pathway of a user. However, in other embodiments the outer shapes of the three respective layers may vary and need not be identical. The acceleration grid 102 includes a mesh of electrical conductors forming pores or holes each having a diameter greater than the pores or holes of the negative grid 120. However, in other embodiments, the pores of the acceleration grid 102 are the same as or smaller than the pores of the negative grid 120. The collector plates 116 may be positioned around the edges of the frame, such as the sides of the frame so as to not interfere with the breathing. As shown, the collector plates 116 are positioned in front of the electronics compartment 122 to optimize the cross-sectional surface area of the porous layers in front of the respiration pathway while minimizing the overall size of the electro-ionic device 100. The collector plates 116 may include a hydrogel 104 having virucidal oxidizing agents such as, sodium hypochlorite, hydrogen peroxide, sodium percarbonate, sodium perborate, or benzalkonium chloride, embedded therein to help ensure that any virus or bacteria collected is killed. In the embodiment shown, the emitter 124 is positioned behind the collector plates 116, but in other embodiments, the emitter 124 may be positioned in front of the collector plates 116 or both in front of and behind the collector plates 116.

The electronics compartment 122 may include a high voltage circuit, such as a Cockcroft-Walton generator, for generating a high voltage output. During operation, the high voltage circuit in the electronics compartment 122 can apply a voltage potential between the emitter 124 and the collector plates 116 greater than 100 V, preferably between 500 V and 20 kV with the emitter 124 being negatively charged and the collector plates 116 being positively charged and creating an electrostatic precipitator. In some embodiments, the voltage applied may be between 1 kV and 14 kV and preferably between 2 kV and 12 kV. When the emitter 124 is charged with respect to the collector plates 116, electrons build up on the electrodes 126 at their respective tips. Depending on a number of factors, some electrons are transmitted across the gap between the emitter 124 and the collector plates 116. Preferentially, electrons attach to small airborne particles in the gap imparting a negative charge thereto. These charged particles can be precipitated out and/or attracted to the nearby positively charged collector plates 116 creating an inertial diversion. In addition, the acceleration grid 102 may also be positively charged with respect to the emitter 124. Due to this charge, negatively charged particles may be attracted to the acceleration grid 102 and it may assist in creating an ionic movement away from the user's face. The charge of the acceleration grid 102 may be the same as the collector plates 116 or the charge may be less positive so as to continue to attract the particles away from the face and toward the collector plates 116 after contacting the acceleration grid 102.

In addition to the emitter 124, the negative grid 120 may also be negatively charged. The negative grid 120 may have the same charge as the emitter 124 or its charge may be lower. The negative grid 120 may serve to repel negative charges from entering the airway. The user contacting conductor 108 may also impart a negative charge onto the user's body, in particular, onto tissue near the mask, such as openings to the mouth and nostrils, to further repel the negatively charged particles from settling onto the surface of the user's body. The negative grid 120 may attract and neutralize positively charged particles generated by the emitter 124 as a byproduct of ionization of the air, such as ozone.

As mentioned above, ozone may be produced as a byproduct of the ionization of the air. Ozone itself is an oxidizing agent and is effective in killing viruses and bacteria. However, at some concentrations, ozone is also an irritant to the lungs. Therefore, circuitry in the electronics compartment 122 may control the amount of ozone generated. For example, the voltage potential between the emitter 124 and collector plates 116 may be optimized to generate safe levels of ozone to assist in killing viruses. For example, the emitter 124 may generate less than 0.1 ppm of inhaled air. The emitter 124 may preferably generate less than 0.05 ppm. The electro-ionic device 100 may incorporate sensors (not shown) for detecting and measuring inspiration and expiration. For example, the electro-ionic device 100 may incorporate a thermistor and/or pressure sensor or strain gage. These sensors may communicate with a controlling circuit for controlling the voltage potential between the emitter 124 and the collector plates 116 to generate high levels of ozone during expiration and lower levels of ozone during inspiration. High levels of ozone during expiration may help kill any stored viruses attached to components of the electro-ionic device 100. The controlling circuit may oscillate the voltage between the emitter 124 and collector plates 116 between 1.2 kV and 12 kV, during inspiration and expiration respectively. More preferably, the controlling circuit may oscillate the voltage between the emitter 124 and collector plates 116 between 2.4 kV and 12 kV, during inspiration and expiration respectively. The voltage gradient may fundamentally be a DC bias voltage, but for improved function, an AC voltage component with a frequency between 50 Hz and 100 kHz may be superimposed onto the DC voltage. Returning to the negative grid 120, since it may be comprised of nickel, chromium, manganese, or alloys comprised of these metals such as a stainless steel alloy, the surface may oxidize and assist in the degradation of ozone to diatomic oxygen thus further reducing the concentration of breathable ozone.

The electro-ionic device 100 may also include a gasket (not shown) around the filtrate layer 106 to improve the fit and seal of the device to the skin. The gasket may be comprised of a silicone gel, hydrogel, or polyvinyl polymers among other polymeric or elastomeric materials. The thickness of the gasket may be between 0.5-6.0 mm, preferably 1-4 mm and applied to both sides of the filtrate layer 106 or folded over onto both sides of the filtrate layer 106. In addition, the gasket may include tabs or protrusions to assist the user in removing from the face.

In one embodiment of the electro-ionic device 100, or any of the following embodiments discussed below, the electro-ionic device 100 may also have a self-sealing port (not shown) for receiving a straw from a beverage to maintain hydration levels all day without removing the electro-ionic device 100 from the user's face. In another embodiment, the self-sealing port may instead be a plug port having a plug portion attached via a tether to a port portion such that the plug portion can be withdrawn from the port portion to allow a drinking straw to be passed through the port portion. Once the straw is withdrawn from the port portion, the plug portion can again be inserted into the port portion to seal the port portion. In some instances, the plug portion may be a Bluetooth-equipped microphone, which when placed in the port portion, can receive and broadcast the voice of the person wearing the electro-ionic device 100.

Although ozone may irritate the lungs at some concentrations, it may also be therapeutic. Indeed, it has been found that ozone introduced into the respiratory tract may help treat a Covid-19 infection. For therapy, in some cases the concentration of ozone may be below 0.1 ppm, but in other cases it may exceed this level. For example, the concentration may be between 0.1 and 0.15 ppm, between 0.15 and 0.2 ppm, or above 0.2 ppm. The electro-ionic device 100 may be configured to deliver ozone in a therapeutic mode or in a therapeutic setting. Moreover, any of the subsequently described electro-ionic devices may also be configured to deliver therapeutic ozone.

Figure 6:
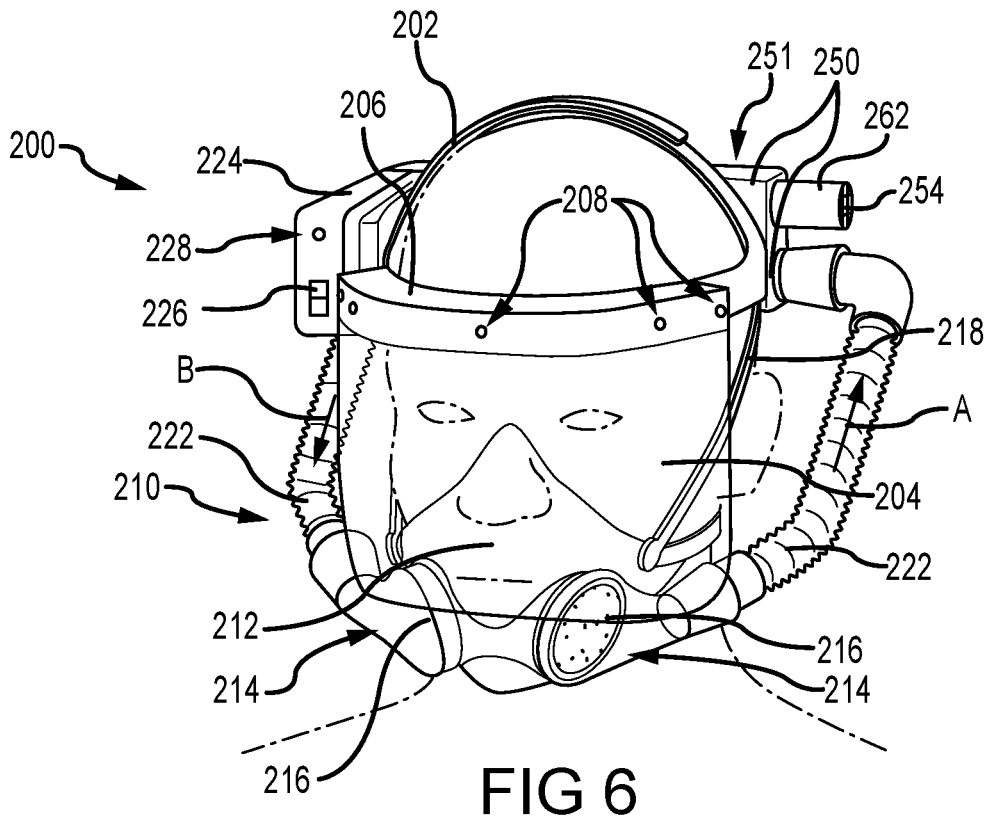
FIG. 6 is a perspective view of an electro-ionic device according to an exemplary embodiment of the present disclosure.

Another exemplary embodiment of an electro-ionic device 200 is shown in FIG. 6. The electro-ionic device 200 may include similar or the same components as the electro-ionic device 100. Wherever possible, the same reference numbers will be used for brevity.

The electro-ionic device 200 may include an adjustable headband 202 for attaching itself to the head and supporting various components of the electro-ionic device 200. A transparent face shield 204 may be mounted onto a face shield spacer 206 positioned at the front of the headband 202 to position the face shield 204 substantially concentrically outward from the headband 202 and outward from the face to at least provide clearance for a mask subassembly 210. The face shield spacer 206 may be comprised of a semi-rigid material, such as a closed cell foam or an elastomer, to allow it to conform to the shape of a user's forehead. The face shield spacer 206 may include a number of mounting tabs 208 for reversibly mounting the face shield 204 thereto. The face shield 204 may be comprised of a plastic, such as polycarbonate and may be configured to be replaced via the mounting tabs 208.

Figure 27:
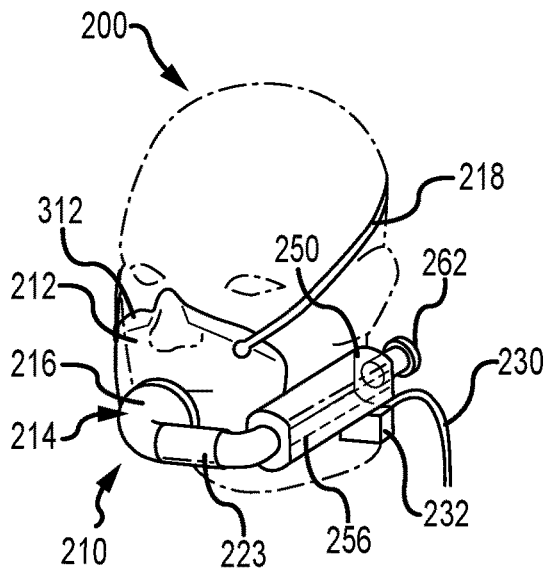
FIG. 27 is a perspective view of an electro-ionic device according to an exemplary embodiment of the present disclosure.
Figure 28:
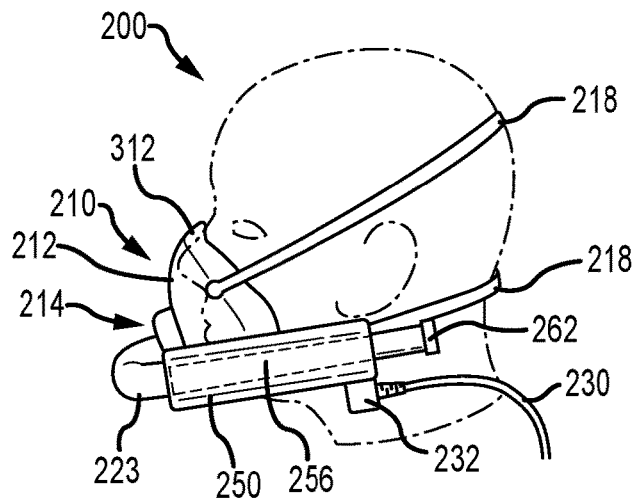
FIG. 28 is a side view of the electro-ionic device of FIG. 27.
Figure 29:
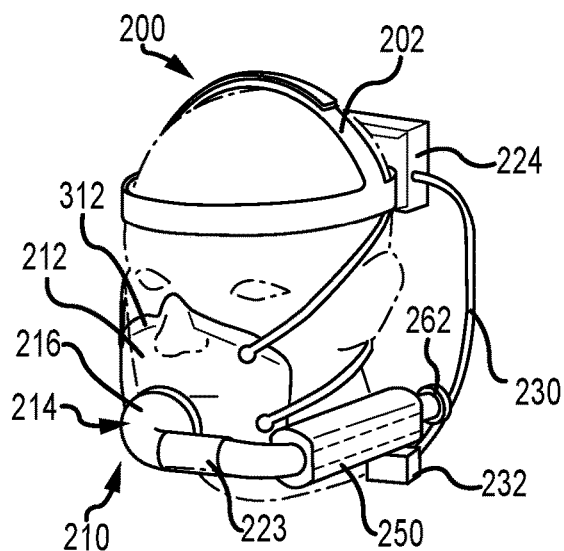
FIG. 29 is a perspective view of an electro-ionic device according to an exemplary embodiment of the present disclosure.
Figure 30:
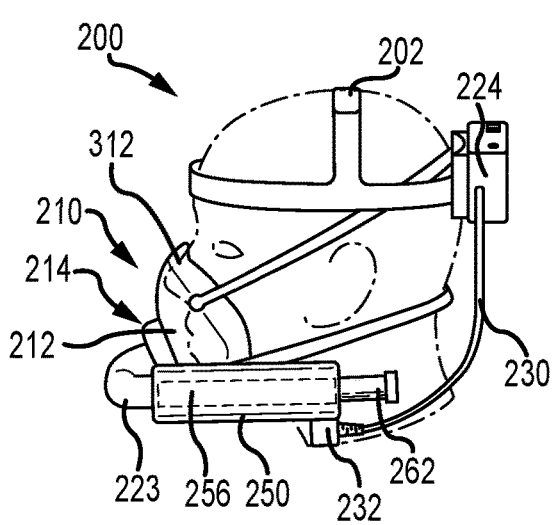
FIG. 30 is a side view of the electro-ionic device of FIG. 27.

The mask subassembly 210 may include a mask 212 comprised of a transparent soft plastic, such as a silicone or polyvinyl. The mask 212 may have one or more openings 214 for inspiration and/or expiration. In the embodiment shown in FIG. 6, the mask 212 includes two openings 214 away from the face when worn properly as shown in FIG. 6, but in other embodiments (shown and described below, e.g., with respect to FIGS. 26-30), the mask 212 may include a single opening. Each of the openings 214 may be separately dedicated for only inspiration or expiration or they may both be configured for both inspiration and expiration. Each of the openings 214 may have a filtrate layer 216 substantially the same as filtrate layer 106 discussed above, other than its size. The mask subassembly 210 may include straps 218 for attaching the mask subassembly 210 to a user's head. The straps 218 may be elastic and flexible. In some embodiments, such as the electro-ionic device 200 shown in FIG. 6, the straps 218 may connect to or be integrated with the headband 202. In other embodiments, such as embodiments without a headband 202 (shown and described below, e.g., FIGS. 27 and 28), the straps 218 may engage directly with the user's head.

The electro-ionic device 200 may also include a gasket (not shown in FIG. 6, but see gasket 312 in FIGS. 27-30, for example) around the mask 212 to improve the fit and seal of the device to the skin. The gasket 312 may be comprised of a silicone gel, hydrogel, or polyvinyl polymers among other polymeric or elastomeric materials. The thickness of the gasket may be between 0.5-6.0 mm, preferably 1-4 mm and extend along the face-contacting border of the mask 212, as can be understood from FIGS. 27-30. The gasket may include tabs or protrusions to assist the user in removing from the face. As already discussed above, the electro-ionic device 200 may also have a self-sealing port or other type of port for receiving a straw from a beverage to maintain hydration levels all day without removing the electro-ionic device 200.

Figure 10:
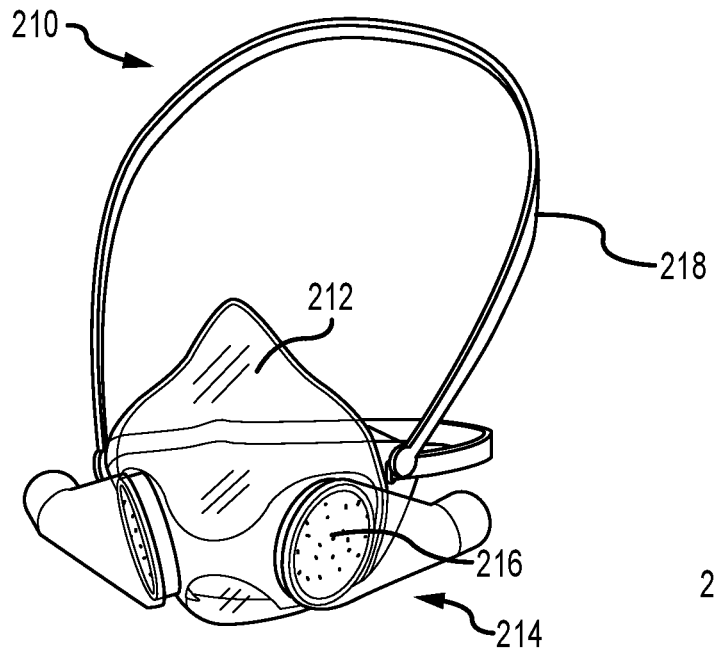
FIG. 10 is a perspective view of a mask filter according to an exemplary embodiment of the present disclosure.
Figure 11:
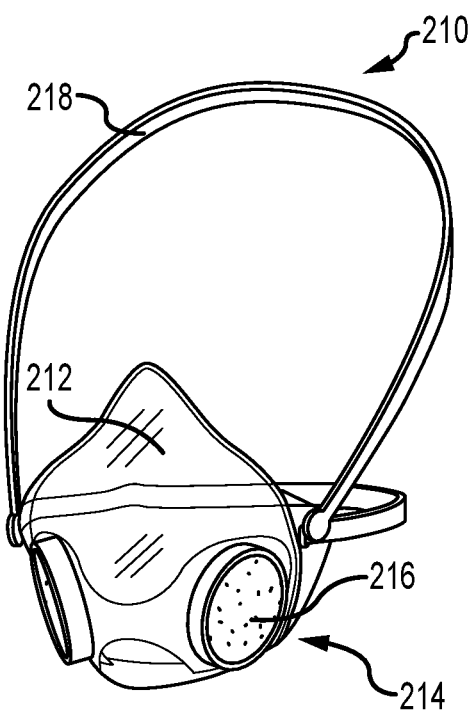
FIG. 11 is a perspective view of the mask filter from FIG. 10 showing some of the components thereof.
Figure 12:
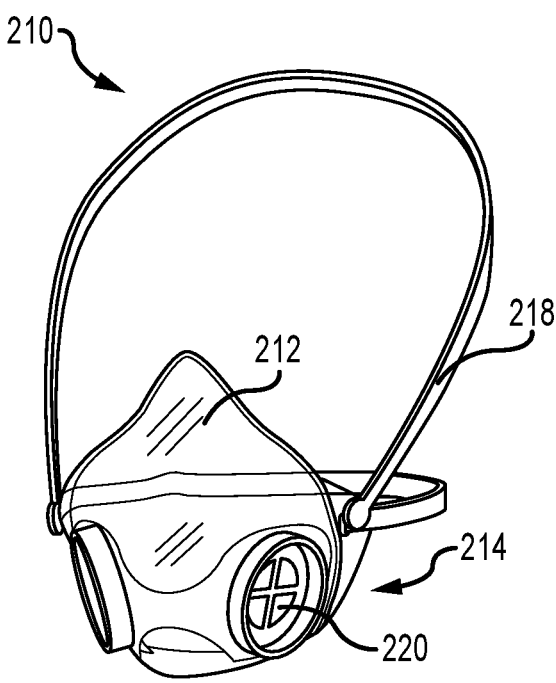
FIG. 12 is a perspective view of the mask filter from FIG. 10 showing some of the components thereof.

FIGS. 10-12 show the mask 212 with bidirectional valve-controlled airflow that mitigates snorkel dead space. More specifically, and as shown in FIG. 12, the openings 214 may also include a one-way valve 220 such as rubber diaphragm or a check-valve. The valves 220 may be configured to permit one of the openings 214 to be used for inspiration only and the other opening 214 for expiration only.

Referring again to FIG. 6, each of the openings 214 may have flexible tubing 222 connected thereto and extend to an ionization filter 250 defining a fluid passageway or conduit therebetween. The flexible tubing 222 may include various adapters and tubing segments, in addition, the tubing 222 may have corrugations 223 to provide improved flexibility and may have an interior diameter of 12-25 mm, preferably 15 mm.

In some embodiments, as shown in FIGS. 26-30, in addition to employing flexible tubing, which may be smooth 222 or corrugated 223, the fluid passageway or conduit may be modular such that segments of the tubing may be arranged male-female to allow for adjustment of length of a section of tubing between the openings 214 and the ionization filter 250 or other components of the electro-ionic device 200. Such an adjustable modular arrangement allows for adjustment to accommodate differently sized user heads.

In some embodiments where the device 200 employs a single airflow conduit for both inhalation and exhalation, or where multiple airflow conduits are employed for both inhalation and exhalation, the adjustable modular arrangement of the device 200 allows the volume of the electro-ionic device 200 to have its total volume adjusted (i.e., the combined volume of the mask 212, volume of tubing(s) 222, 223, and volume of ionizer chamber(s) 250) to an optimal volume for the user so as to avoid snorkel effect issues (e.g., rebreathing and failure of air adequate air exchange). In one embodiment, the device 200 will have an adjustable total volume ranging between approximately 80 ml and approximately 100 ml. In some embodiments, the device 200 will not be adjustable with respect to its total volume and will simply be available at different incremental sizes such as extra-small, small, medium, large and extra-large for different user size user heads and offering different total volumes ranging between 80 ml and 100 ml (for example, 80 ml, 85 ml, 90 ml, 95 ml and 100 ml for sizes extra-small, small, medium, large and extra-large, respectively).

The headband 202 may also support an electronics unit 224 and the ionization filter 250. The electronics unit 224 may include a power supply and electronic circuitry the same as or similar to the batteries 118 and the circuitry within the electronics compartment 122 as discussed above with regard to the electro-ionic device 100. In addition, the electronics unit 224 may include a power switch 226 and indicator light 228.

Figure 7:
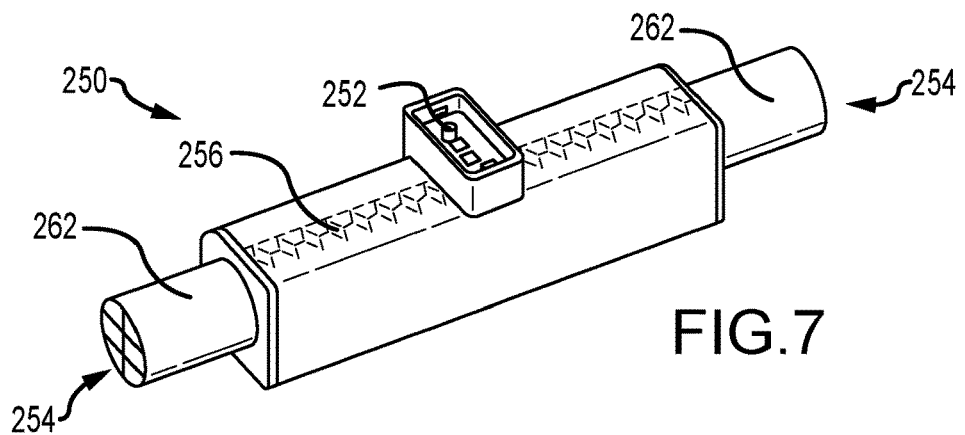
FIG. 7 is a perspective view of an ionization filter according to an exemplary embodiment of the present disclosure.
Figure 8:
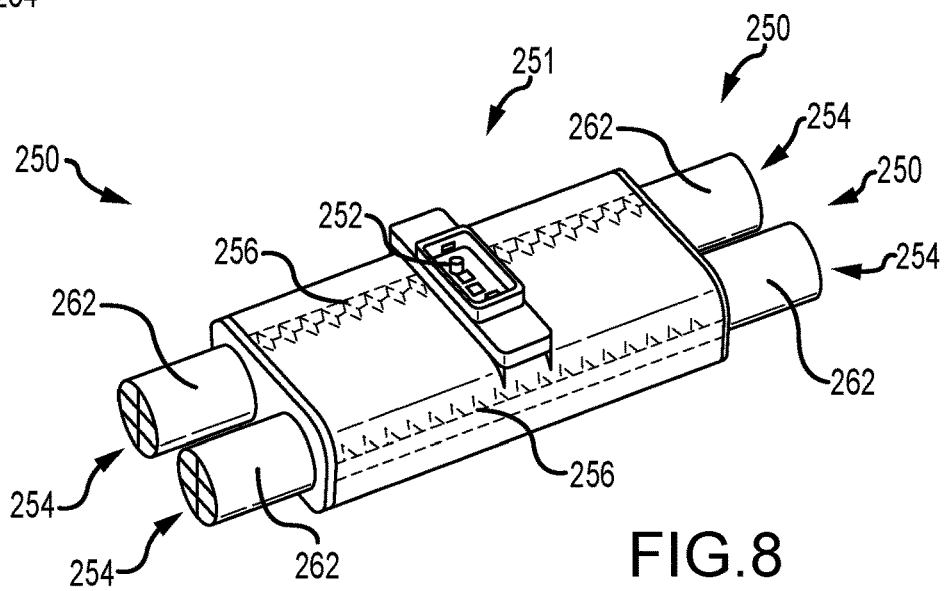
FIG. 8 is a perspective view of an ionization filter from FIG. 6.
Figure 14:
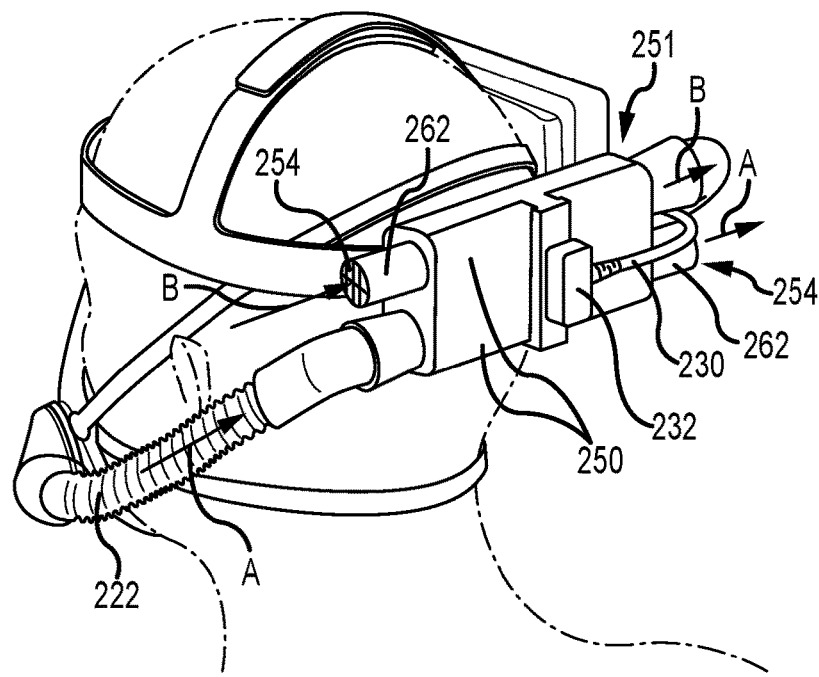
FIG. 14 is a back perspective view of the electro-ionic device from FIG. 13.

As shown in FIGS. 7, 8, and 14, the electronics unit 224 may be connected to the ionization filter 250 via a cable 230. In particular, an end of the cable 230 may contain a male connector 232 which interfaces with a female connector 252 formed in the ionization filter 250. The cable 230 may include two conductors (not shown) to provide low voltage power to the male connector 232. The male connector 232 may include high voltage circuitry, such as a Cockroft-Walton generator to convert the low voltage power to a high voltage supply to the ionization filter 250. In other embodiments, the ionization filter 250 may include the high voltage circuitry to convert the low voltage power inside the ionization filter 250. In yet other embodiments, the electronics unit 224 may include the high voltage circuitry and the cable 230 may provide the high voltage power to the ionization filter 250. The male connector 232 may also include a spring loaded resistor (not shown), such as between 100 ohms and 10,000 ohms, configured to intermittently contact conductor pads on the female connector 252 during disengagement with or unplugging of the male connector 232 to safely dissipate any residual high voltage in the ionization filter 250 and to limit current flow to the ionization filter 250 during an initial charging when the male connector 232 is initially plugged into the female connector 252. The cable 230 may also include a pin loop connector (not shown) for removing the voltage supplied by the electronics unit 224 upon disconnection of male connector 232 from the ionizer filter 250.

Figure 9A:
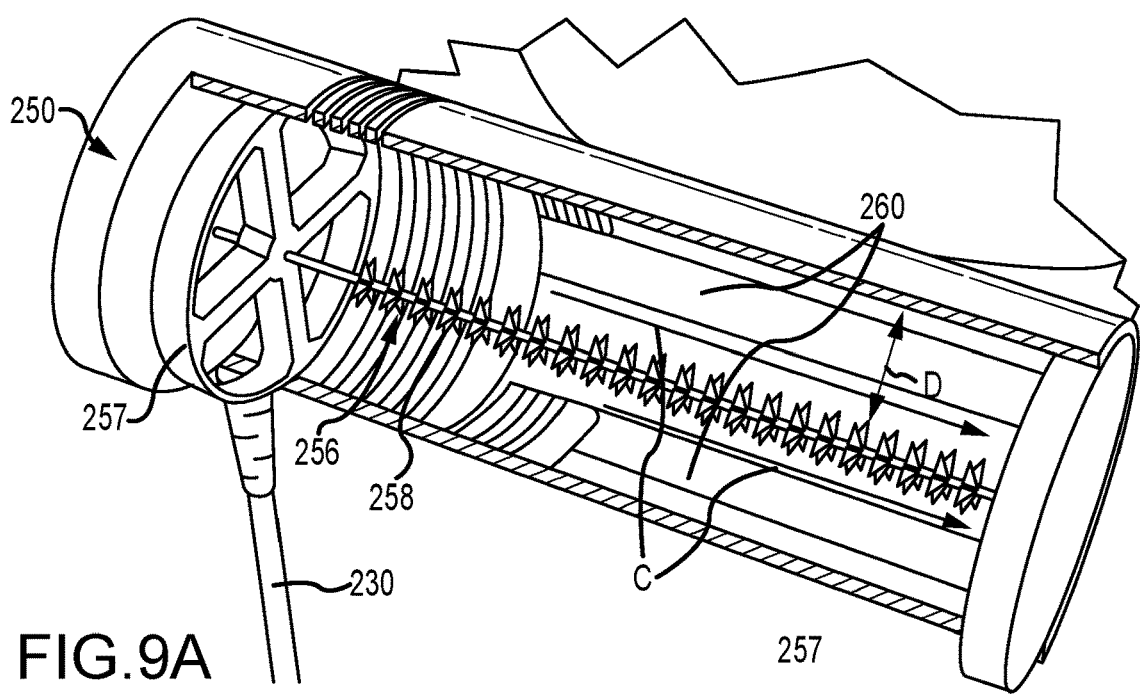
FIG. 9A is a perspective view of an ionization filter according to an exemplary embodiment of the present disclosure.

FIGS. 7, 9A, and 9B illustrate a single ionization filter 250 and FIG. 8 illustrates two ionization filters 250 joined together in the same housing to form a dual ionization filter assembly 251. The ionization filters 250 shown in FIGS. 7, 9A and 9B have slightly different geometry, but include substantially the same elements and function in the substantially same way. The ionization filter 250 may have a tube-shaped housing with openings 254 at opposed ends. Either one of the openings 254 can operate solely as an inlet, while the other opening 254 operates as an outlet, such as when the ionization filter 250 is configured for only one of inspiration or expiration. In some embodiments, both inspiration and expiration take place though a single ionization filter 250 and both openings can be both inlets and outlets. The housing may have a cylindrical or frustoconical extension 262 immediately adjacent the openings to allow the flexible tubing 222 to attach thereto.

As best shown in FIGS. 9A and 9B, an emitter 256 extends longitudinally along a central axis through an inside of the cavity of the ionization filter 250 and is held centered therein by spacers 257. In other embodiments not shown, the emitter 256 extends longitudinally along a wall of the housing. In addition, the emitter may be protected with a ceramic material or other shielding material having a high emissivity. The emitter 256 may function in substantially the same manner as emitter 124 discussed above. The emitter 256 may include a plurality of electrodes 258 extending radially outward from the emitter 256, comprising similar materials as discussed above with respect to the electro-ionic device 100. The electrodes 258 may be axially spaced apart from one another and have one or more of radially extending points at any particular axial position.

As shown in FIGS. 9A and 9B, the chamber of the ionization filter 250 may also include one or more collector plates 260. The collector plate(s) 260 may surround the emitter 256 along the inside of the housing and may have a substantially circular or rectangular cross-section along the axial length of the emitter 256. The collector plate 260 may be comprised of similar materials as the collector plates 116 as discussed above with respect to the electro-ionic device 100. The ionization filter 250 may be removed from the electro-ionic device 200 for cleaning. Cleaning the ionization filter may include washing with water or other solutions including detergents, solvents, and/or oxidizing agents.

Still referring to FIGS. 9A and 9B, as can be understood from the Arrows C, which represent the general direction of airflow through the cavity of the ionization filter 250, the airflow direction is substantially, if not completely, parallel to the surface of the collector 260 and longitudinal axis of the emitter 256. Also, the general direction of airflow through the cavity of the ionization filter 250 is substantially, if not completely, perpendicular to the radially outwardly projecting tips of the electrodes 258.

As indicated by Arrow D in FIGS. 9A and 9B, in some versions of the embodiments disclosed herein, the operational voltage for the ionizer filter will be between approximately 5 kV and approximately 15 kV, and preferably 6 kV to 11.5 kV for a distance (Arrow D) between the tip of the emitter and collector of 15 mm, at sea level. For other embodiments, with a distance (Arrow D) between the tip of the emitter and collector between approximately 10 mm and approximately 20 mm, the operational voltage for the ionizer filter will be between approximately 4 kV and approximately 20 kV, at sea level.

In some embodiments, the voltage and current are adjustable to fine tune the filtration of the ionization filter to the elevation and circumstances. Additionally, in some embodiments, the collector is mechanically and selectively positionable relative to the emitter such that a distance (Arrow D) between the collector and tip of the emitter can be set to accommodate the settings of the current and voltage to optimize filtration. Such an embodiment may be accomplished via a mechanical arrangement that causes the collector to radially increase or decrease its offset from the emitter it surrounds. Alternatively, the housing of the ionization filter may be configured to allow different collectors to be swapped out, the different collectors having different radii and therefore different offset distances (Arrow D) from the surrounded emitter.

As shown in FIG. 9A, the spacers 257 may have straight or non-spiral vanes or spokes such that they do not spiral the airflow along the chamber path between the emitter 256 and collector 260. However, as can be understood from FIGS. 9B, 9C and 9D, to help extend the effective length of the airflow within the chamber to achieve greater dwell time of the airflow and its particles within the chamber of the ionization chamber 250 to afford an increased chance that the particles will be pulled from the airflow and attached to the collector 260, the spacers 257 may have spiral vanes 259 that spiral the airflow, or at least cause turbulence of the airflow. Such a spiral airflow facilitating arrangement allows the chamber of the ionization filter 250 to have a shorter longitudinal length, size and weight than would otherwise be possible. As can be seen in FIG. 9B, the spiral vanes 259 may extend into chamber of the ionization chamber 250 in a series of stacked layers arrangements to increase the likelihood the airflow with spiral within the chamber.

As indicated in FIG. 9B, and as is the case with all the other embodiments of the ionization filter 250 disclosed herein, a conductor 261 will extend from the power source and electronics of the electronics unit 224 to the emitter, and another conductor 263 will extend from the battery and electronics of the electronics unit 224 to the emitter 256. These conductors are routed from the electronics unit 224 to the ionization filter 250 via the cable 230, as can be seen in FIG. 9A.

In some embodiments, the electro-ionic device 200 may have a preferred orientation such as one of the openings 254 to be oriented closer to the mask subassembly 210 than the other opening 254. In such embodiments, the extension 262 nearer to the mask assembly 210 may include a negative grid substantially similar in material and function as the negative grid 120 and the extension 262 farther to the mask assembly 210 may include an acceleration grid substantially similar in material and function as the acceleration grid 102.

Figure 13:
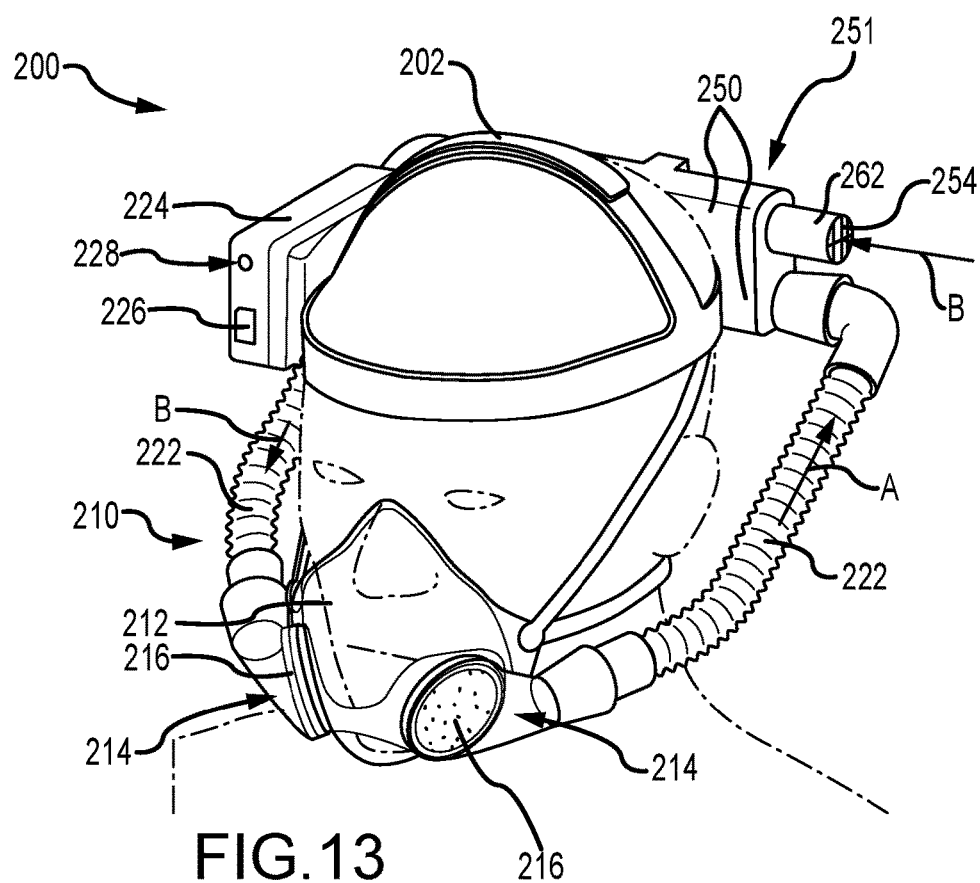
FIG. 13 is a front perspective view of an electro-ionic device according to an exemplary embodiment of the present disclosure.

In the embodiments shown in FIGS. 6, 13 and 14, which employ a dual ionization filter assembly 251, an exhalation pathway is called out via Arrow A and exists as a first pathway from mask 212, through a first one of the openings 214, through a first one of the flexible tubing 222, through a first one of the ionization filters 250, and then out a first one of the openings 254, this one-way airflow being facilitated via a first valve 220 (e.g., as shown in FIG. 12) for one-way air flow located in the first opening 214 underneath a first filtrate layer 216.

Still referring to FIGS. 6, 13, and 14, an inhalation pathway is called out via Arrow B and exists as a second pathway from a second one of the openings 254, through a second one of the ionization filters 250, through a second one of the flexible tubing 222, through a second one of the openings 214, and then into the mask 212, this one-way airflow being facilitated via a second valve 220 (e.g. as shown in FIG. 12) for one-way air flow located in the second opening underneath a second filtrate layer 216. In such a configuration air entering the second pathway may be filtered before it is inhaled and filtered after it is exhaled and passes through the first pathway. Because the air passing through the second pathway is configured to be inhaled, the amount of ozone generated in the second ionization filter 250 may be kept at safe level, such as 0.1 ppm or lower. On the other hand, because the air exiting the first ionization filter 250 is not configured to be directly inhaled, the amount of ozone generated may be higher than that of the second ionization filter 250.

In another configuration of the embodiments shown in FIGS. 6, 13 and 14, both of the openings 214 may be free of a valve 220, such that inspiration and expiration may take place in both the first and second pathways to reduce the total resistance to breathing through the electro-ionic device 200.

Figure 15:
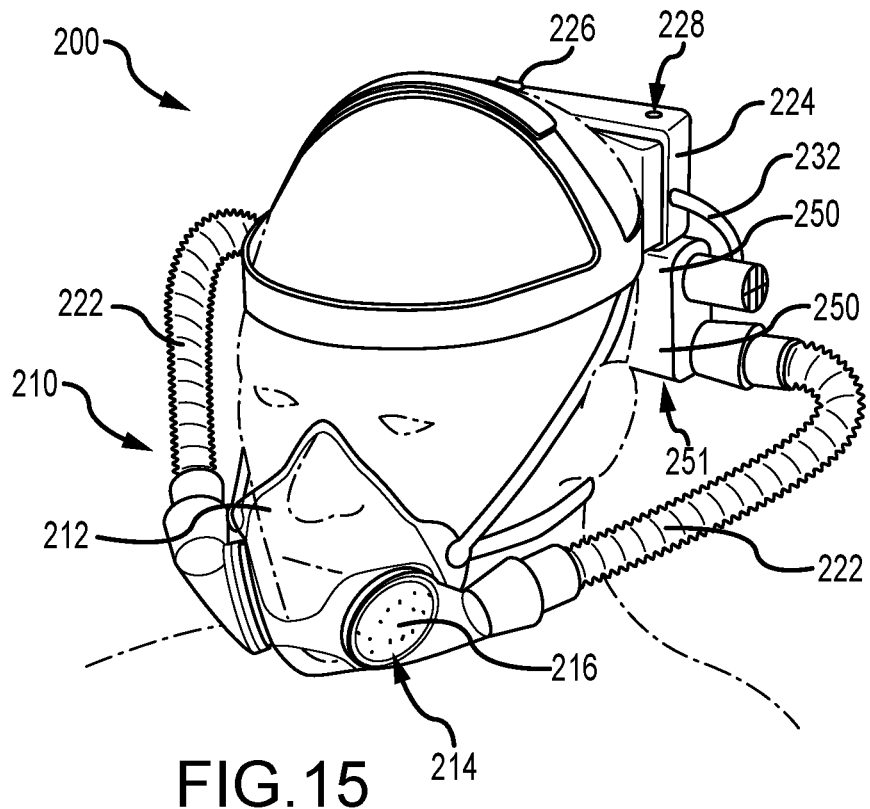
FIG. 15 is a front perspective view of an electro-ionic device according to an exemplary embodiment of the present disclosure.
Figure 16:
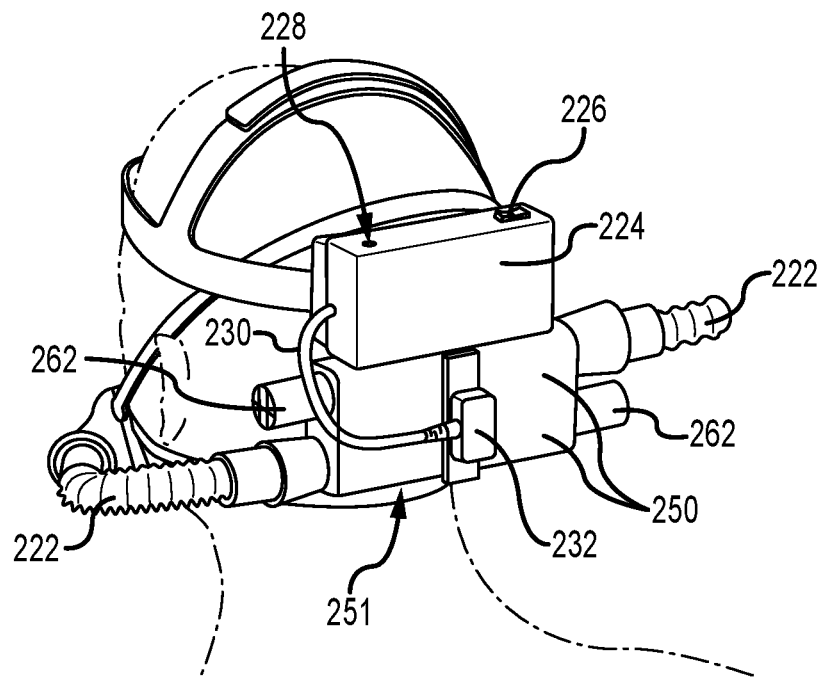
FIG. 16 is a back perspective view of the electro-ionic device from FIG. 15.

The electro-ionic device 200 may have modular components such that it may be configured in various ways, including some of the modular embodiments discussed above, without departing from the scope of the invention. For example, FIGS. 13 and 14 show the electro-ionic device 200 similar to the embodiment shown in FIG. 6 but without the face shield 204. FIGS. 15 and 16 show the electro-ionic device 200 similar to the embodiment shown in FIG. 13 but with the electronics unit 224 mounted above and on top of the ionization filter 250.

Figure 17:
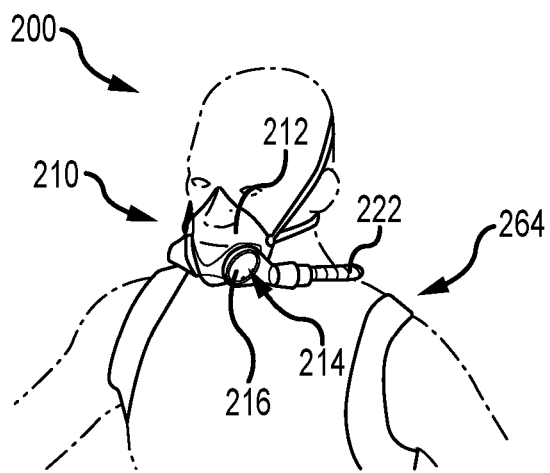
FIG. 17 is a front perspective view of an electro-ionic device according to an exemplary embodiment of the present disclosure.
Figure 18:
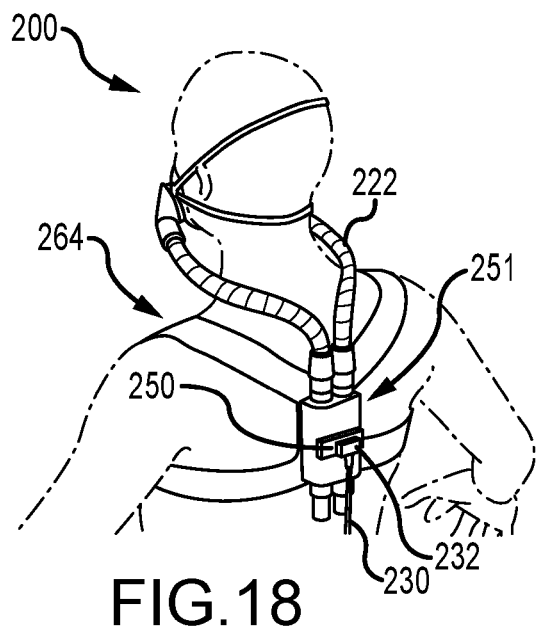
FIG. 18 is a back perspective view of the electro-ionic device from FIG. 17.
Figure 19:
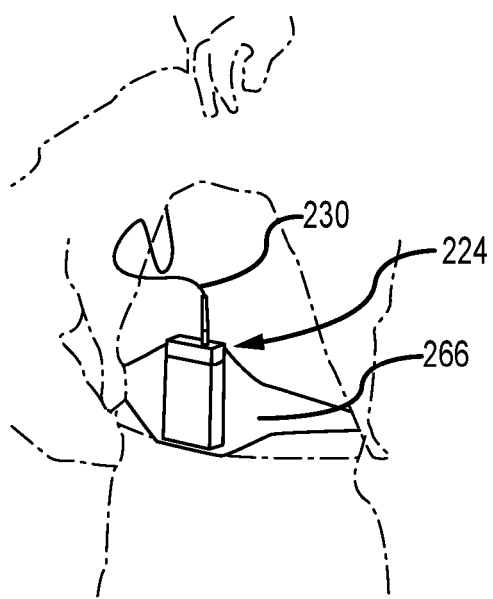
FIG. 19 is a perspective view of a power supply according to an exemplary embodiment of the present disclosure.

FIGS. 17 and 18 shows another embodiment of the electro-ionic device 200 similar to the embodiment shown in FIG. 6, having a shoulder strap 264 for supporting the dual ionization filter assembly 251 on the shoulder straps 264 on the user's back. The embodiment may also include a back strap 266 or another device such as a belt clip for securing the electronics unit 224, such as the back strap 266 shown in FIG. 19.

Figure 20:
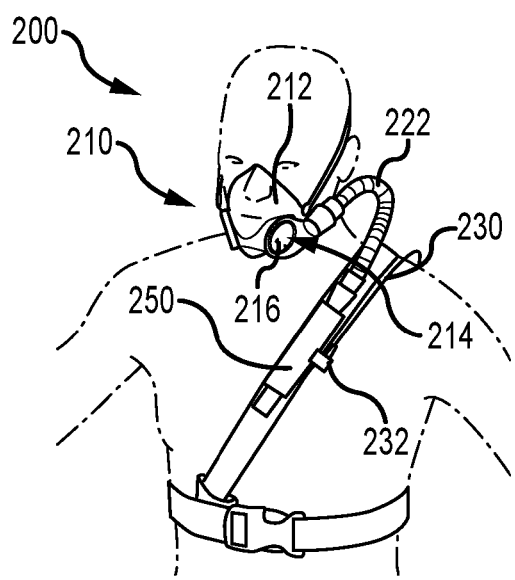
FIG. 20 is a perspective view of an electro-ionic device according to an exemplary embodiment of the present disclosure.
Figure 21:
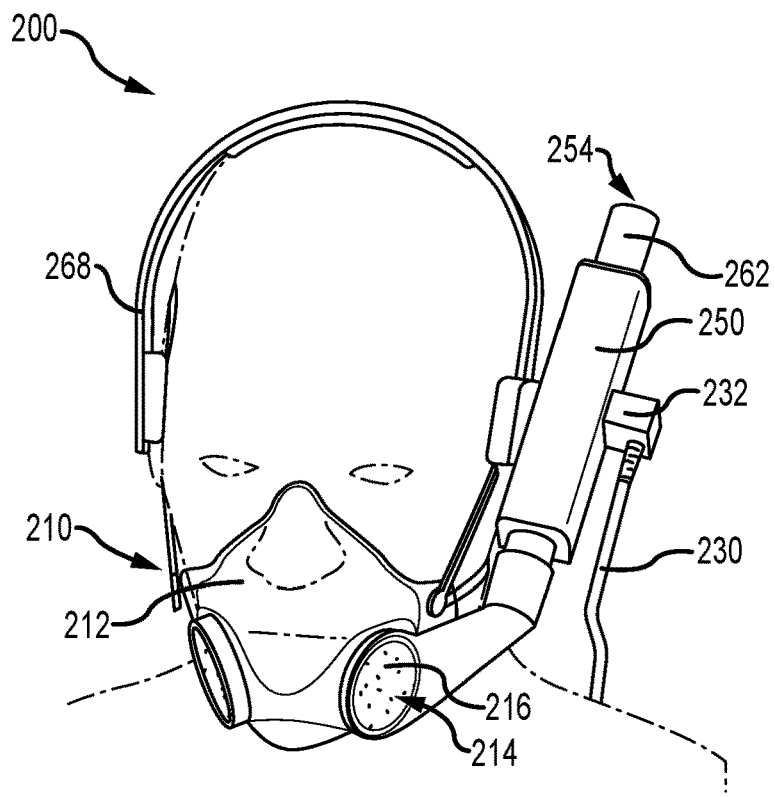
FIG. 21 is a perspective view of an electro-ionic device according to an exemplary embodiment of the present disclosure.

FIG. 20 shows a configuration of the electro-ionic device 200 where only a single ionization filter 250 may be attached to a shoulder strap 264 on the chest and an electronics unit 224 may be attached to a back strap on the back. With electro-ionic device 200 having a single ionization filter 250, the mask subassembly 210 may be configured with a valve 220 in a first opening 214 to permit inspiration through the ionization filter 250 and a valve 220 in the second opening 214 to permit direct expiration through the filtrate layer 216 directly to the environment.

In an alternate version of the embodiment of FIG. 20, the opening 214 may be free of a valve 220, such that inspiration and expiration may take place the pathway leading through the single ionization filter 250 such that exhaled air is treated via the single ionization filter 250.

As can be understood via a review and comparison of the embodiments depicted in FIGS. 13-20, these embodiments illustrate various body fitting arrangements addressing user comfort and wear ability. Also, the embodiments shown in FIGS. 13-20 are modular arrangements of the electro-ionic device 200 where the electronics unit 224 is separated from the ionization chamber(s) 250.

FIGS. 21-25 illustrate embodiments of the electro-ionic device 200 with a single opening 214 that is not occluded and available for both inspiration and expiration, the other opening 214 either being completely occluded or used as a filtered exhaust port. In reference to the embodiment of FIG. 21, it can be understood that this embodiment is also similar to the embodiment of FIG. 20, but instead of the single ionization filter 250 being supported by a shoulder strap, it is supported by a head set 268.

Figure 22:
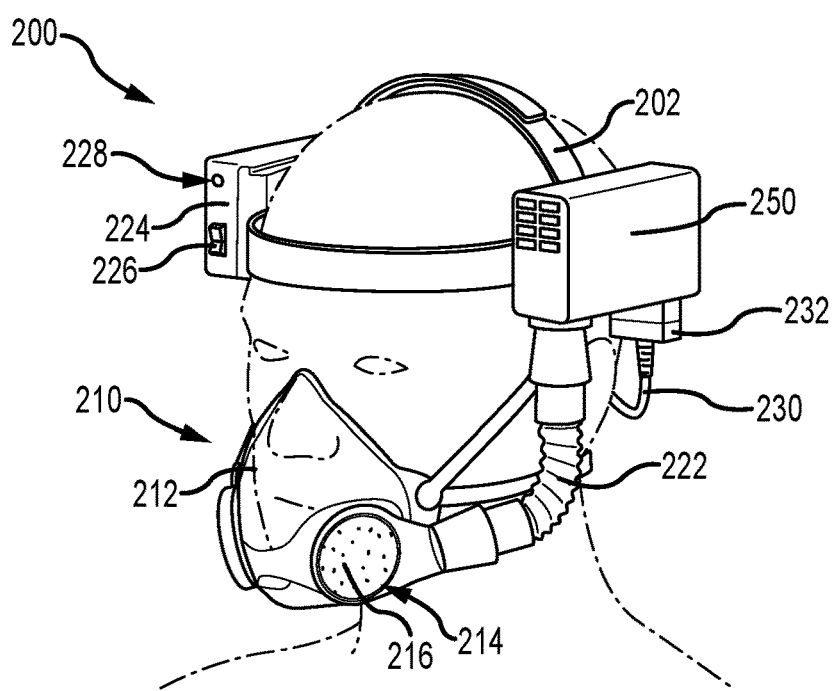
FIG. 22 is a perspective view of an electro-ionic device according to an exemplary embodiment of the present disclosure.
Figure 23:
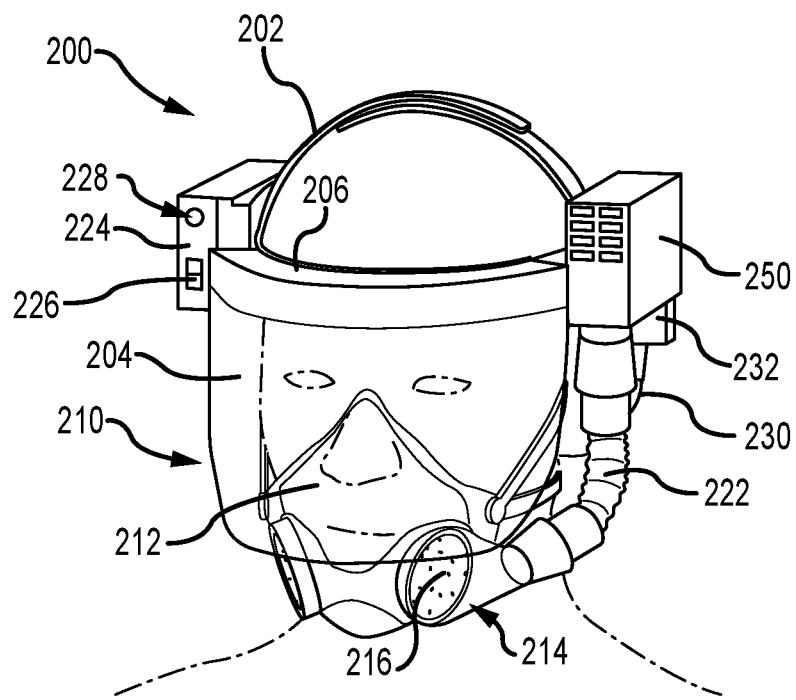
FIG. 23 is a perspective view of an electro-ionic device according to an exemplary embodiment of the present disclosure.

FIGS. 22 and 23 show another configuration of the electro-ionic device 220 in which a single ionization filter 250 is supported by the head band 202. In these embodiments, the ionization filter 250 may be shaped to have a similar size and/or weight as the electronics unit 224.

Figure 24:
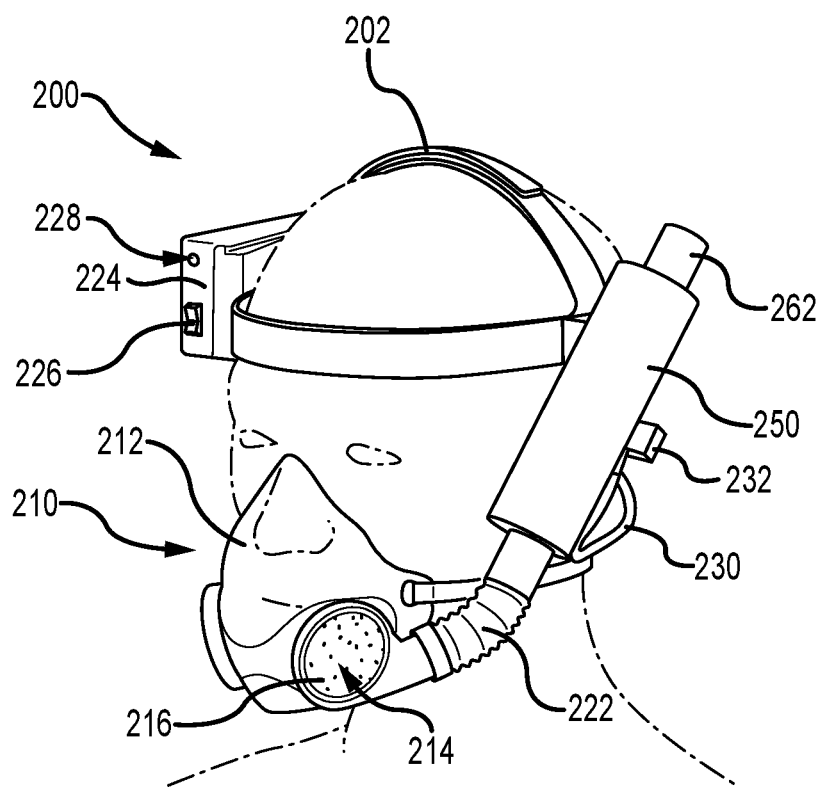
FIG. 24 is a perspective view of an electro-ionic device according to an exemplary embodiment of the present disclosure.
Figure 25:
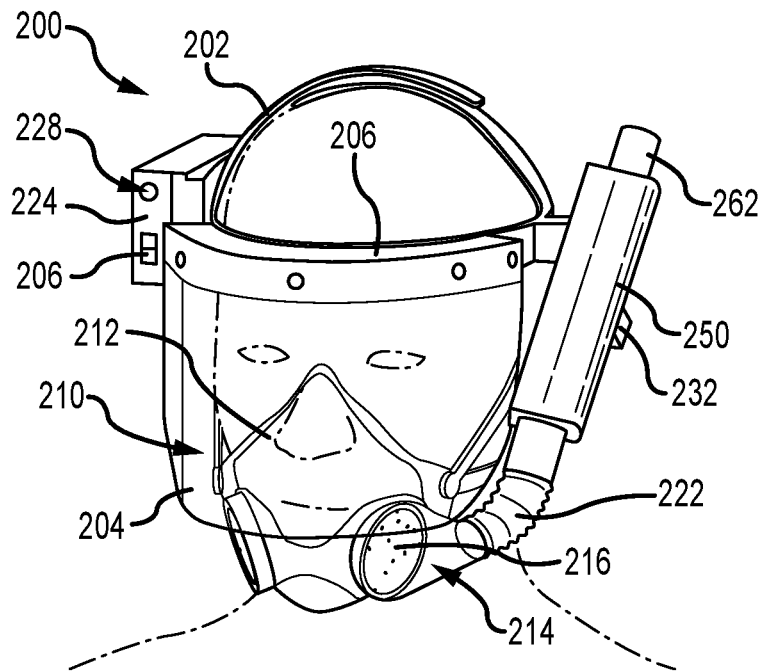
FIG. 25 is a perspective view of an electro-ionic device according to an exemplary embodiment of the present disclosure.
Figure 26:
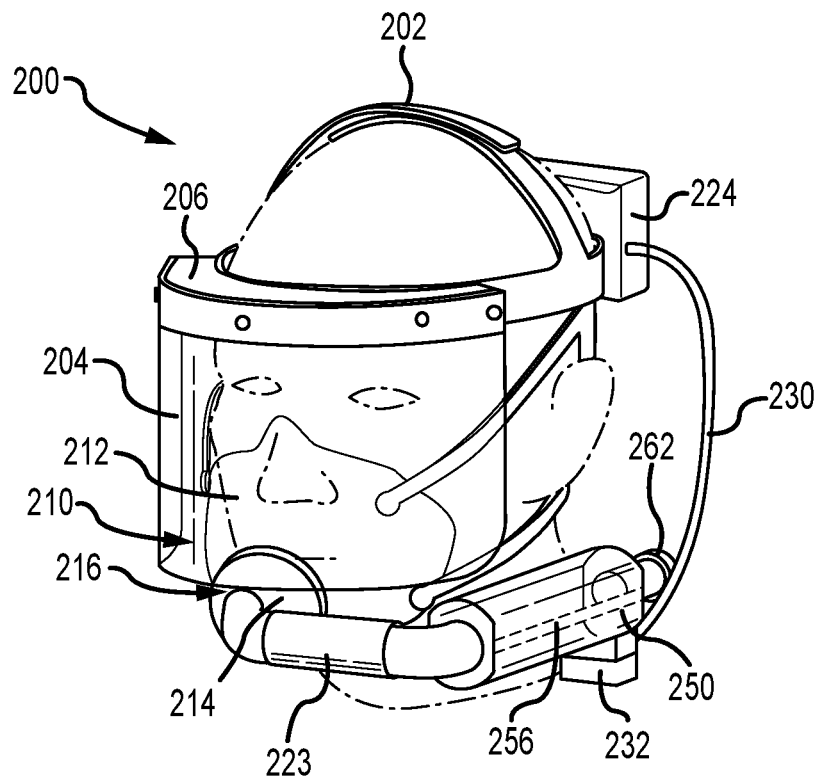
FIG. 26 is a perspective view of an electro-ionic device according to an exemplary embodiment of the present disclosure.

FIGS. 24 and 25 show other embodiments of an electro-ionic device 200 with the single ionization filter 250 supported by a head band 202 at an angle between 10 and 80 degrees, more preferably 20 and 70 degrees with respect to a transverse plane or the head band. Having the ionization filter 250 aligned at an angle may permit the opening 214 to be positioned closer to the mask 212 and reduce breathing resistance and reduce snorkel effect.

FIGS. 26-30 show various configurations of an electro-ionic device 200 with a mask subassembly 210 having a single opening 214 and a single filtrate layer 216. Further, these embodiments show various modular configurations with interchangeable masks 212, ionizing chamber(s) 250, and various mounting of the electronics unit 224.

Figure 31:
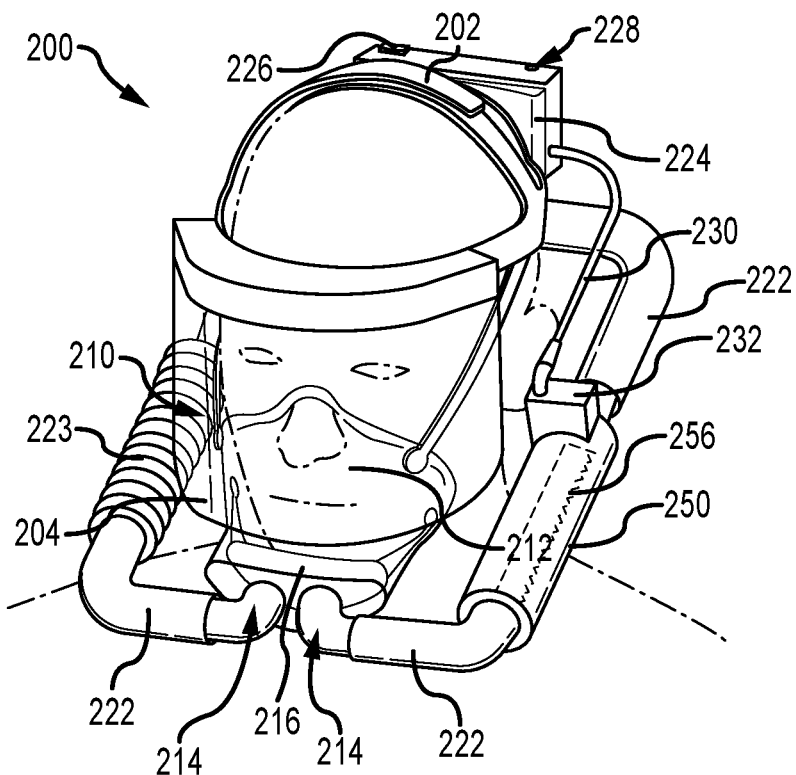
FIG. 31 is a perspective view of an electro-ionic device according to an exemplary embodiment of the present disclosure.
Figure 32:
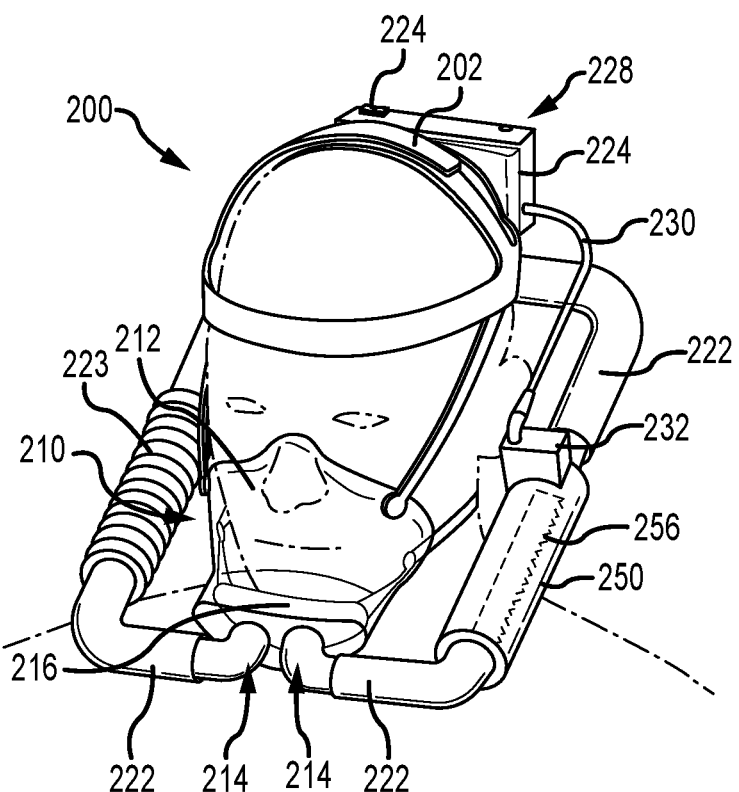
FIG. 32 is a perspective view of an electro-ionic device according to an exemplary embodiment of the present disclosure.
Figure 33:
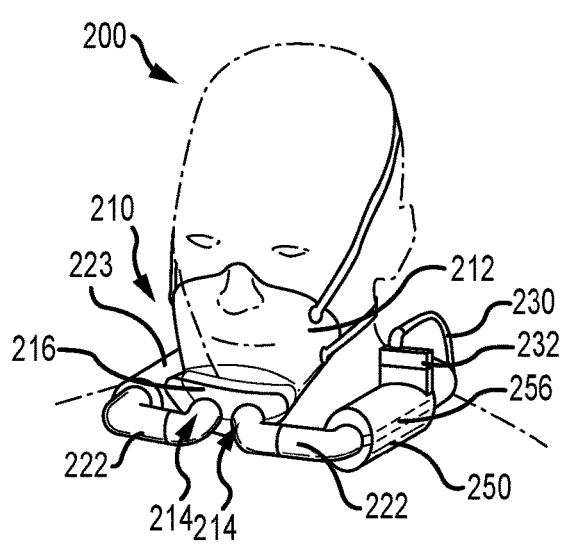
FIG. 33 is a perspective view of an electro-ionic device according to an exemplary embodiment of the present disclosure.

FIGS. 31-33 show another configuration of an electro-ionic device 200 with a mask subassembly 210 with two openings and a single filtrate layer 216. For the embodiments of FIGS. 26-33, the sectioned tubes 222, 223 and their male/female connections facilitate adjustment of the device 200 to fit a variety of user head sizes and adapt the device 200 to minimize snorkel effect. In the context of FIG. 33, the weight of the electro-ionic 200 is configured to rest on the shoulders in contrast to the embodiments of FIGS. 31 and 32, where the weight is supported substantially, if not completely, off the head.

Figure 34:
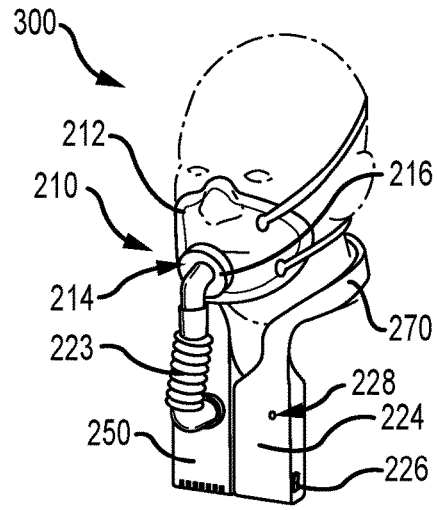
FIG. 34 is a perspective view of an electro-ionic device according to an exemplary embodiment of the present disclosure.
Figure 35:
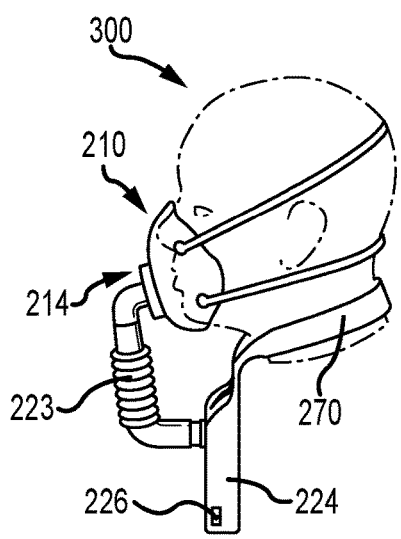
FIG. 35 is a side view of the electro-ionic device from FIG. 34.
Figure 36:
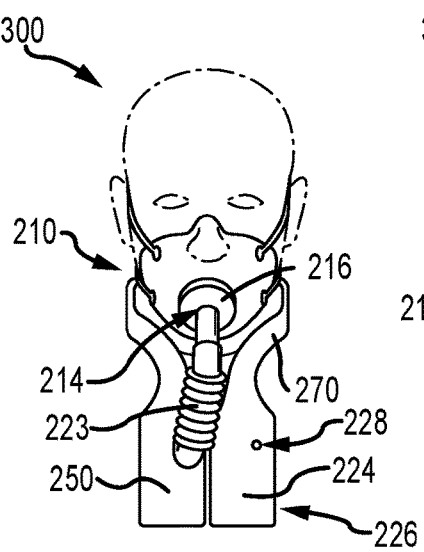
FIG. 36 is a front view of the electro-ionic device from FIG. 34.

FIGS. 34-36 shows another embodiment of an electro-ionic device 300 having similar components as the electro-ionic devices 100 and 200 discussed above. In particular, the electro-ionic device 300 may have the ionization filter 250 and the electronics unit 224 housed in the same housing or housing units that are integrally connected to each other. The housing may include a neck strap 270 configured to support the electro-ionic device 300 on the back of a user's neck and house conductive wires extending between the ionization filter 250 and the electronics unit 224. Thus, the weight of the electro-ionic device 200 for the embodiments of FIGS. 34-36 is supported off the user's neck.

In addition, for the embodiments of FIGS. 34-36, the mask assembly 210 may include a single opening 214 and may be modular allowing for varied arrangements and adjustment of its components. Similar to the electro-ionic device 100, the electronics unit 224 may have sensors configured to detect inspiration and expiration and alter a voltage between the emitter 256 and the collector plates 260 based on whether inspiration or expiration is detected. In doing so, the emitter may be configured to emit a higher level of ozone during expiration than during inspiration. Such an ozone modulation control sequence may also be employed with any of the embodiments discussed herein wherein a single airflow conduit handles both inspiration and expiration.

Figure 37:
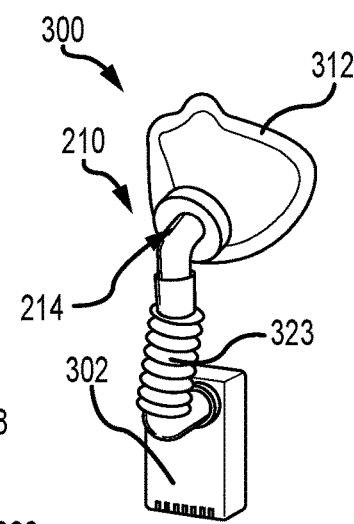
FIG. 37 is a perspective view of an electro-ionic device according to an exemplary embodiment of the present disclosure.

FIG. 37 shows another configuration of an electro-ionic device 300 having a combined housing 302, which houses both the ionization filter 250 and the electronics unit 224.

Figure 38:
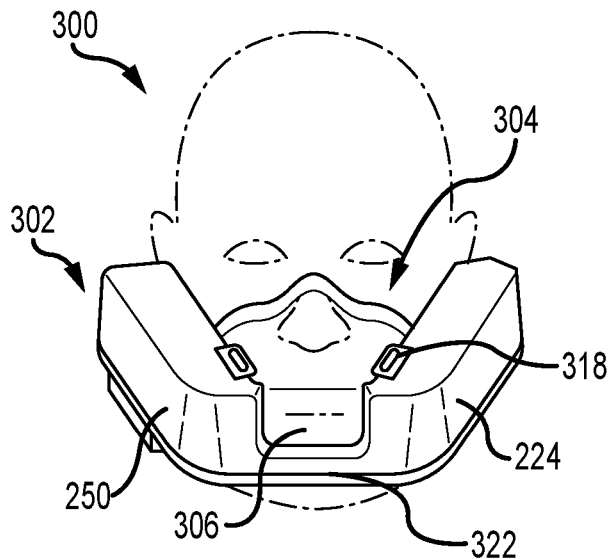
FIG. 38 is a perspective view of an electro-ionic device according to an exemplary embodiment of the present disclosure.

FIGS. 38-39H and 42 show another embodiment of an electro-ionic device 300, FIGS. 40A-40H show different views of a mask 212 of the electro-ionic device 300 from FIG. 38, and FIGS. 41A-41H show different views of a housing 302 of the electro-ionic device 300 from FIG. 38. As can be understood from FIG. 38, the housing 302 may be categorized into two general sections, one side including the ionization filter 250 and an opposite side including the electronics unit 224. The housing 302 may form a bridge portion 322 between the ionization filter 250 with the electronics unit 224 and may house electrical conductors connecting these two units to each other.

Figure 40A:
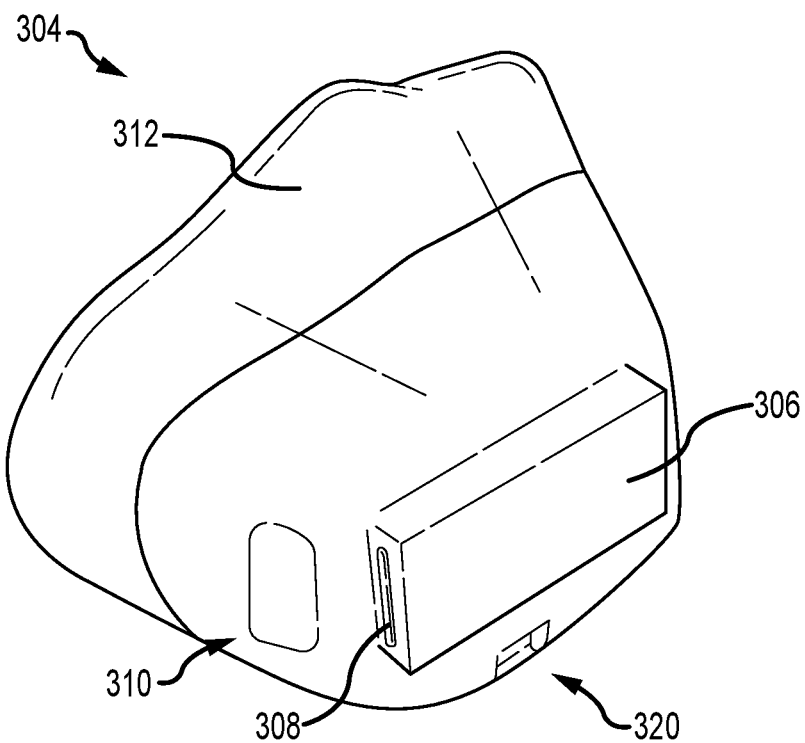
FIG. 40A is a top, front, right-side perspective view of a mask from FIG. 39A.
Figure 40B:
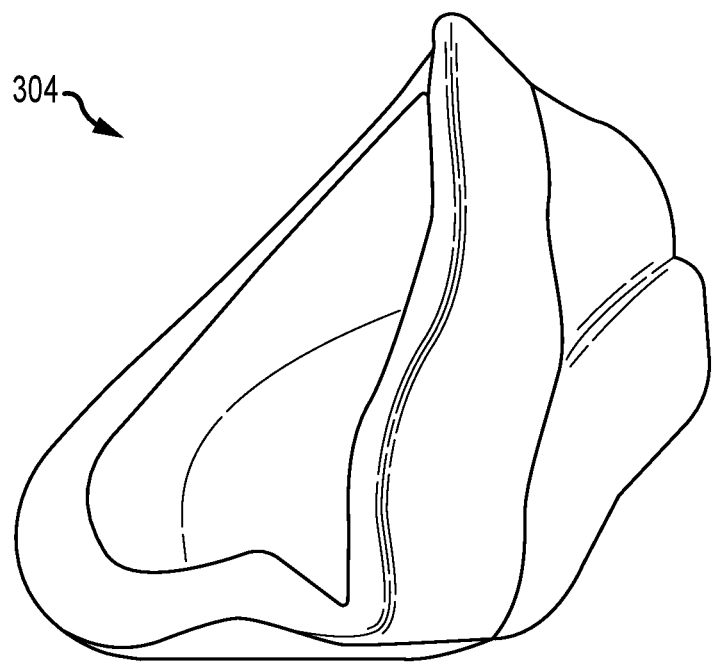
FIG. 40B is a bottom, back, left-side perspective view of the mask from FIG. 40A.
Figure 40C:
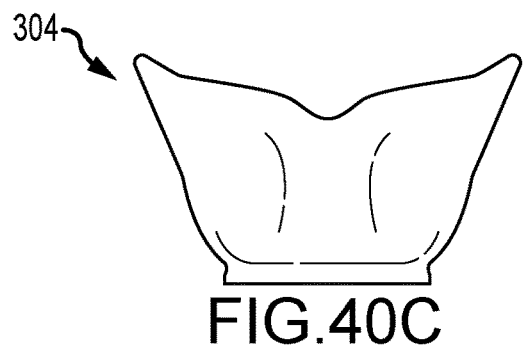
FIG. 40C is a top view of the mask from FIG. 40A.
Figure 40D:
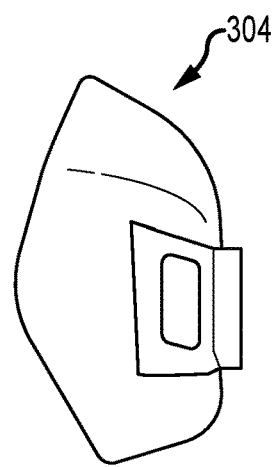
FIG. 40D is a left-side view of the mask from FIG. 40A.
Figure 40E:
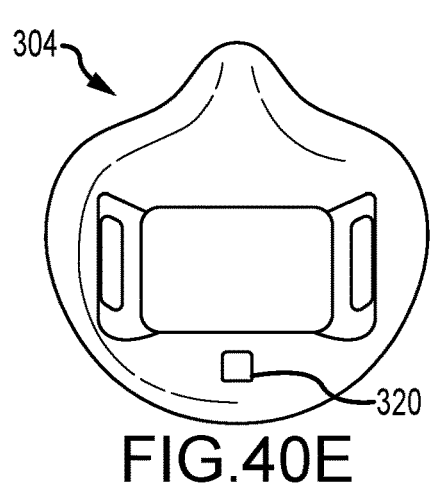
FIG. 40E is a front view of the mask from FIG. 40A.
Figure 40F:
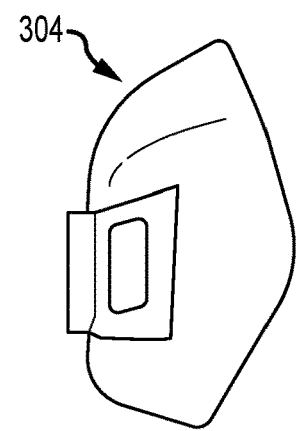
FIG. 40F is a right-side view of the mask from FIG. 40A.
Figure 40G:
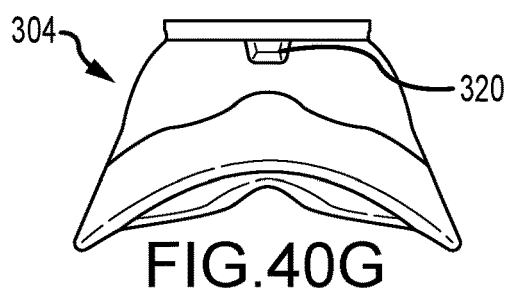
FIG. 40G is a bottom view of the mask from FIG. 40A.
Figure 40H:
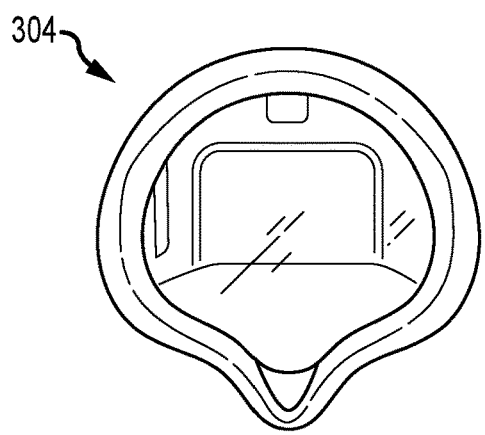
FIG. 40H is a back view of the mask from FIG. 40A.

As illustrated in FIGS. 38 and 40A, the electro-ionic device 300 may include a mask 304 similar to mask 212 in material and function. The mask 304 may have a flat window 306 in the front to enable a clear unobstructed and undistorted view of the user's mouth to minimize the impact of electro-ionic device 300 on nonverbal communication. In addition, the window 306 may include vertically aligned ribs 308 configured to slide in corresponding vertical grooves 314 (shown in FIGS. 41A and 41B) of the housing 302 for attachment thereto.

As shown in FIG. 40A, the mask 304 may have an opening 310 that opens into a corresponding opening of the ionization filter 250. The electro-ionic device 300 may also include a gasket 312 around the mask 304 to improve the fit and seal of the device to the skin. The gasket 312 may be comprised of a silicone gel, hydrogel, or polyvinyl polymers among other polymeric or elastomeric materials. The thickness of the gasket 312 may be between 0.5-6.0 mm, preferably 1-4 mm and applied to both sides of the mask 304 or folded over onto both sides of the mask 304. The gasket 312 may include tabs or protrusions to assist the user in removing it from the face. As described above in reference to the devices 100 and 200, the electro-ionic device 300 may also have a port (not shown) for receiving a straw from a beverage to maintain hydration levels all day without removing the electro-ionic device 300.

Figure 41A:
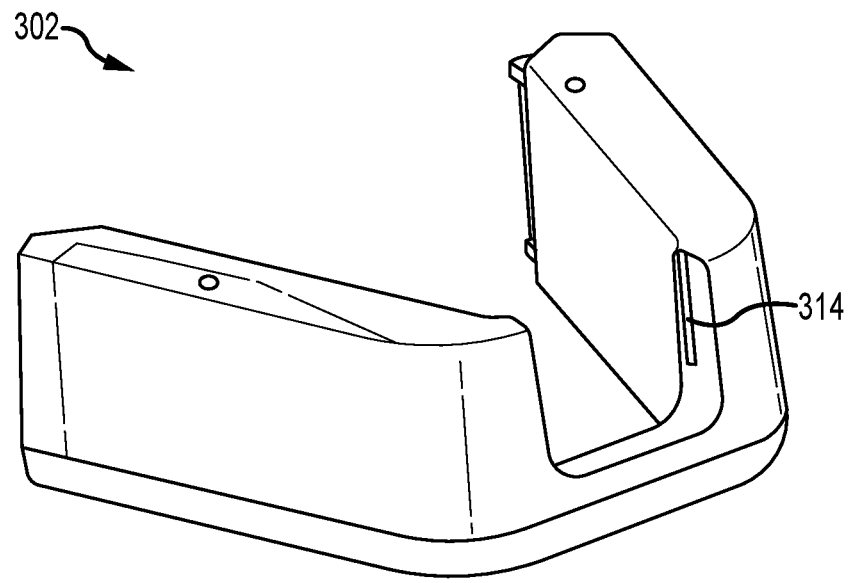
FIG. 41A is a top, front, right-side perspective view of a housing from FIG. 39A.
Figure 41B:
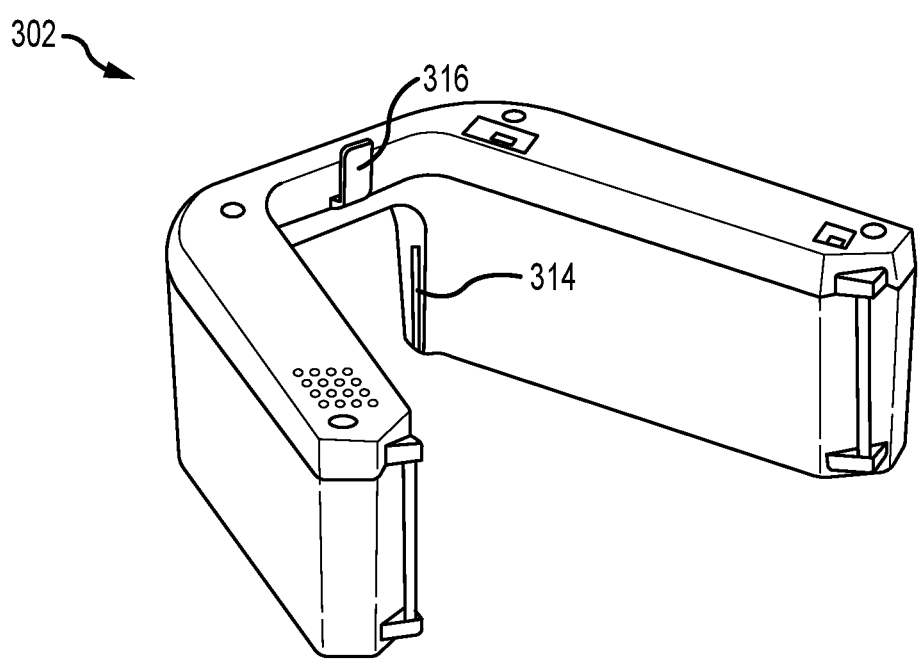
FIG. 41B is a bottom, back, left-side perspective view of the housing from FIG. 41A.
Figure 41C:
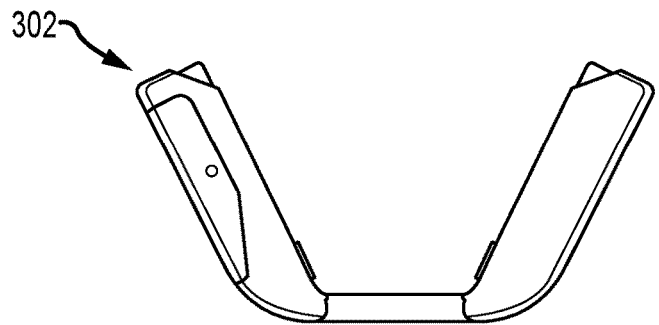
FIG. 41C is a top view of the housing from FIG. 41A.
Figure 41D:
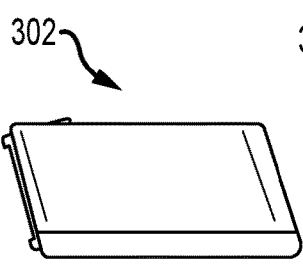
FIG. 41D is a left-side view of the housing from FIG. 41A.
Figure 41E:
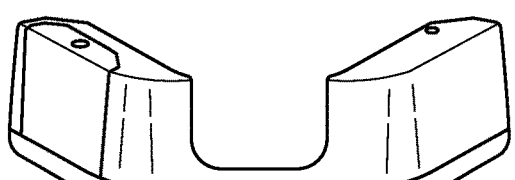
FIG. 41E is a top, front perspective view of the housing from FIG. 41A.
Figure 41F:
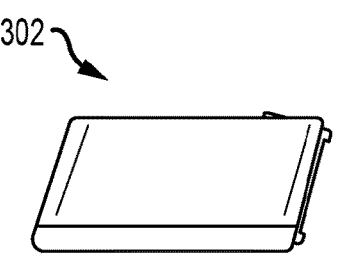
FIG. 41F is a right-side view of the housing from FIG. 41A.
Figure 41G:
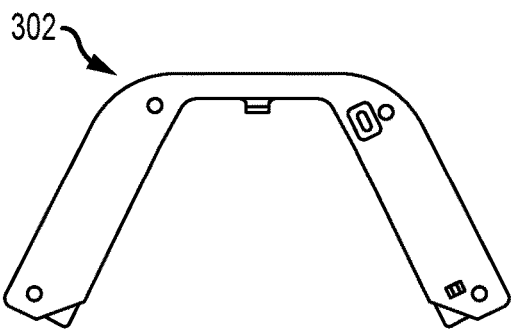
FIG. 41G is a bottom view of the housing from FIG. 41A.
Figure 41H:
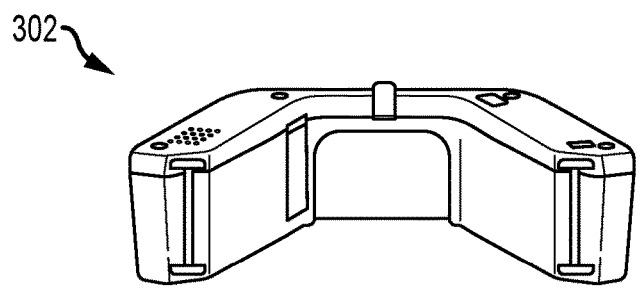
FIG. 41H is a bottom, back, perspective view of the housing from FIG. 41A.

In addition to the mask window ribs 308 and the housing grooves 314, as illustrated in FIGS. 40A and 41B, a lower mask hook 316 of the housing 302 may engage a corresponding slot 320 to help align and secure the mask 304 to the housing 302. After the ribs 308 of the mask window 306 and the grooves 314 of the housing 302 are aligned, removable upper mask clips 318 are configured to secure the mask 304 to the housing 302, as depicted in FIGS. 38 and 43A.

Figure 39A:
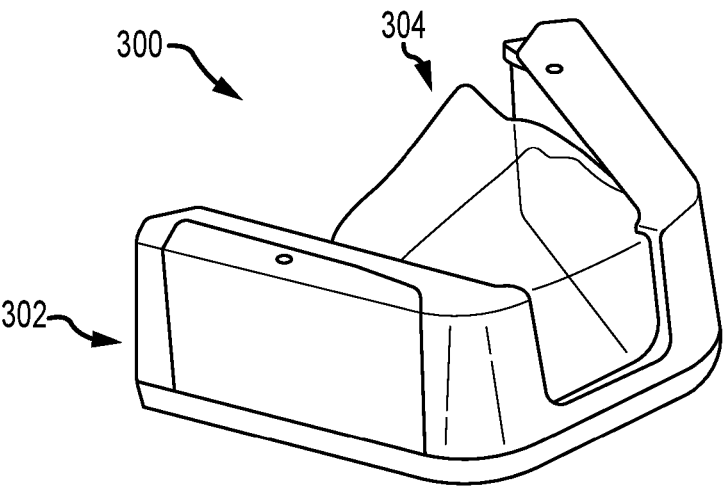
FIG. 39A is a top, front, right-side perspective view of an electro-ionic device according to an exemplary embodiment of the present disclosure.
Figure 39B:
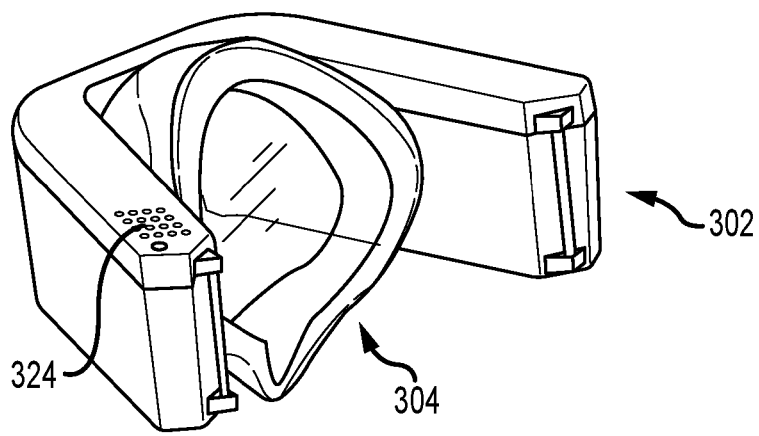
FIG. 39B is a bottom, back, left-side perspective view of the electro-ionic device from FIG. 39A.

As illustrated in FIG. 39B, the housing 302 of electro-ionic device 300 may include an opening 324 which may function as an inlet and outlet to the ionization filter 250. The ionization filter 250 and the electronics unit 224 include the same components and operate in the same or similar manner as discussed above with regard to electro-ionic devices 200 and 300.

As shown in FIG. 42, the ionization filter 250 includes collector plates 260 spaced apart from the emitter 256, and the electronics unit 224 is located on the opposite side. In other embodiments, the electro-ionic device 300 may include two ionization filters 250, one housed on each side of the device.

FIGS. 43A-43C show another embodiment of the electro-ionic device 300 similar to the embodiment shown in FIGS. 38-42 with a smaller sized housing 302 that offers a reduction in view obstruction. However, this embodiment may also include dual ionization filters 250 inside the housing 302 and an external electronics unit 224, similar to some of the embodiments discussed above, the external electronics unit 224 being tethered to the rest of the device 300 via a cable 230.

Figure 44A:
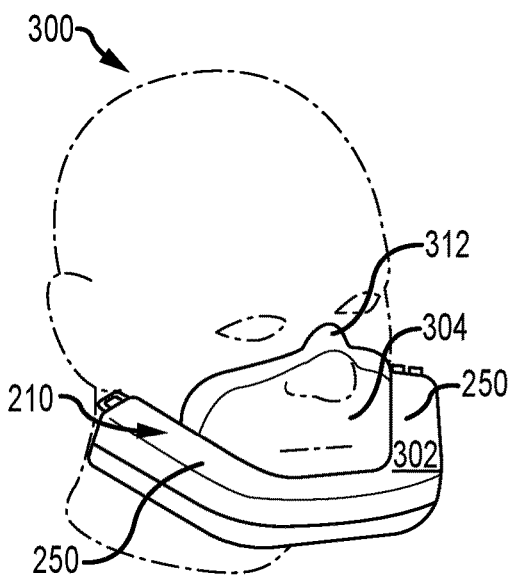
FIG. 44A is a top, front, left-side perspective view of an electro-ionic device according to an exemplary embodiment of the present disclosure.
Figure 44B:
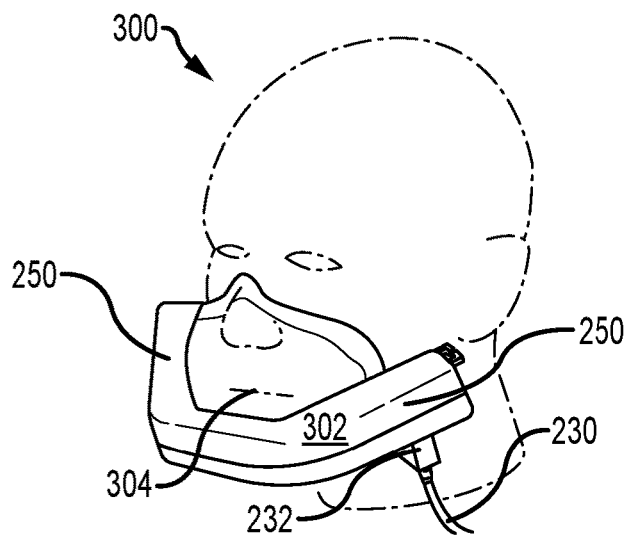
FIG. 44B is a top, front, right-side perspective view of the electro-ionic device from FIG. 44A.

FIGS. 44A and 44B show another embodiment the electro-ionic device 300 similar to the embodiment shown in FIGS. 43A-43C with a different housing 302 that is yet smaller and offers further reduced view obstruction. This embodiment may also include dual ionization filters 250 inside the housing 302 and an external electronics unit 224, similar to some of the embodiments discussed above, the external electronics unit 224 being tethered to the rest of the device 300 via a cable 230.

Figure 45A:
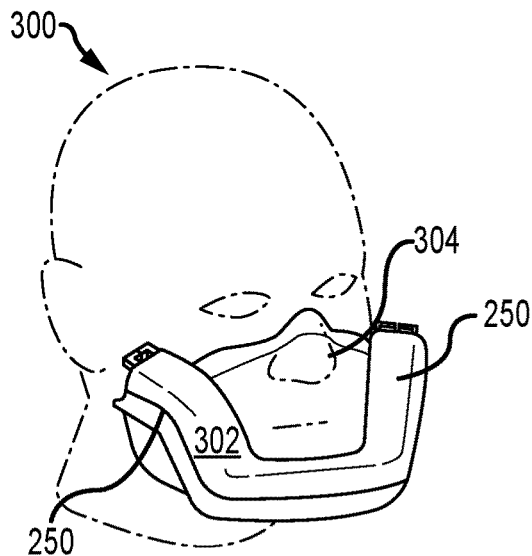
FIG. 45A is a top, front, left-side perspective view of an electro-ionic device according to an exemplary embodiment of the present disclosure.
Figure 45B:
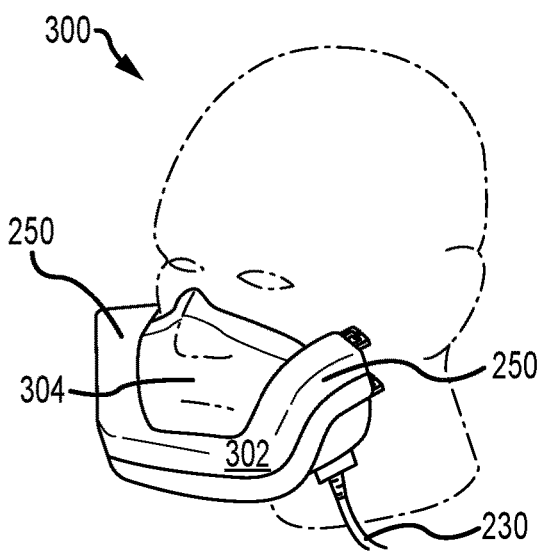
FIG. 45B is a top, front, right-side perspective view of the electro-ionic device from FIG. 45A.
Figure 46A:
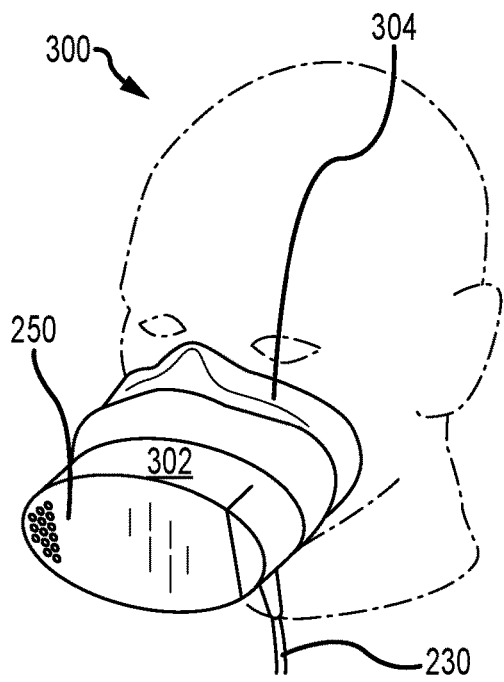
FIG. 46A is a perspective view of an electro-ionic device according to an exemplary embodiment of the present disclosure.
Figure 46B:
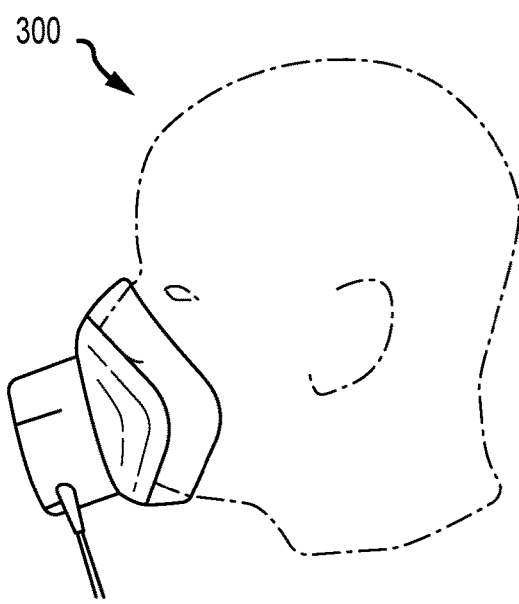
FIG. 46B is a side view of the electro-ionic device from FIG. 46A.
Figure 46C:
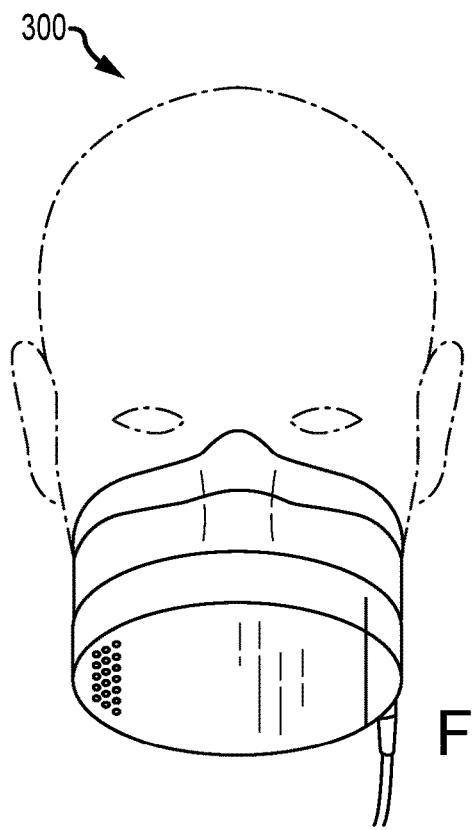
FIG. 46C is a front view of the electro-ionic device from FIG. 46A.
Figure 47A:
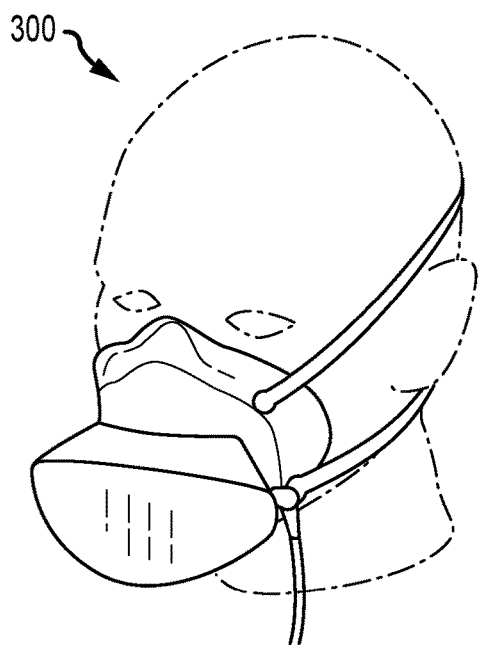
FIG. 47A is a perspective view of an electro-ionic device according to an exemplary embodiment of the present disclosure.
Figure 47B:
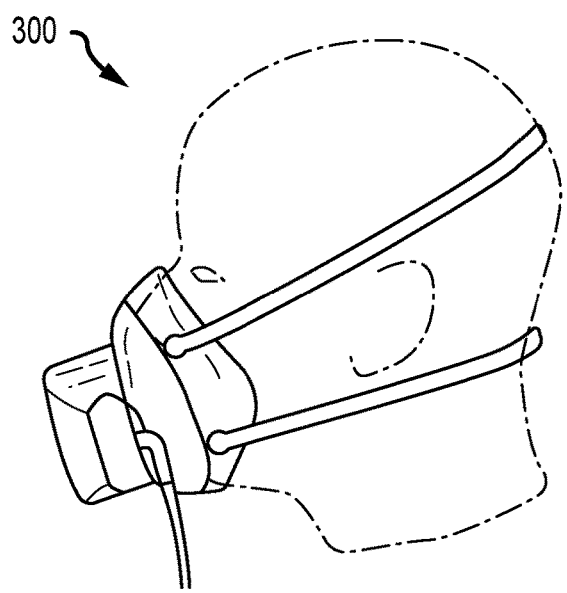
FIG. 47B is a side view of the electro-ionic device from FIG. 47A.
Figure 47C:
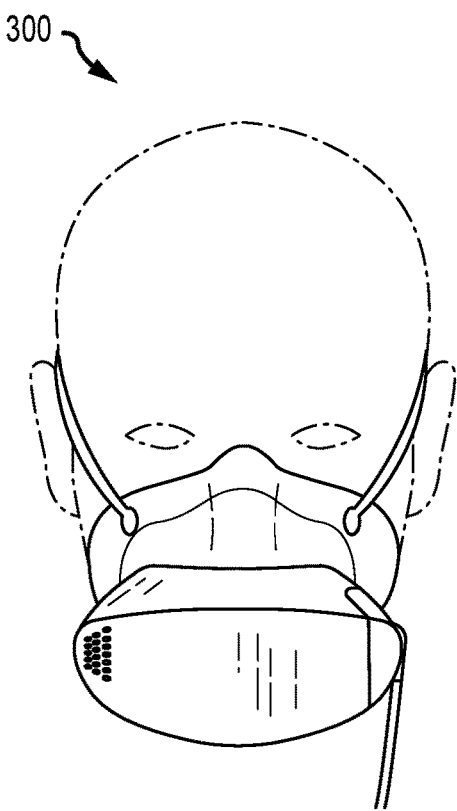
FIG. 47C is a front view of the electro-ionic device from FIG. 47A.
Figure 48A:
FIG. 48A is a perspective view of an electro-ionic device according to an exemplary embodiment of the present disclosure.
Figure 48B:
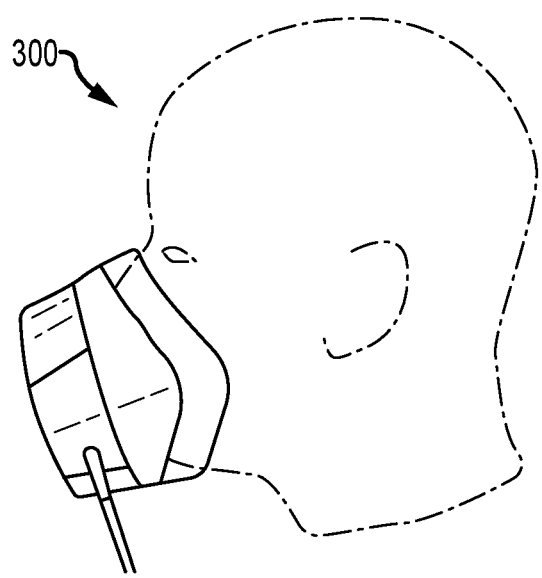
FIG. 48B is a side view of the electro-ionic device from FIG. 48A.
Figure 48C:
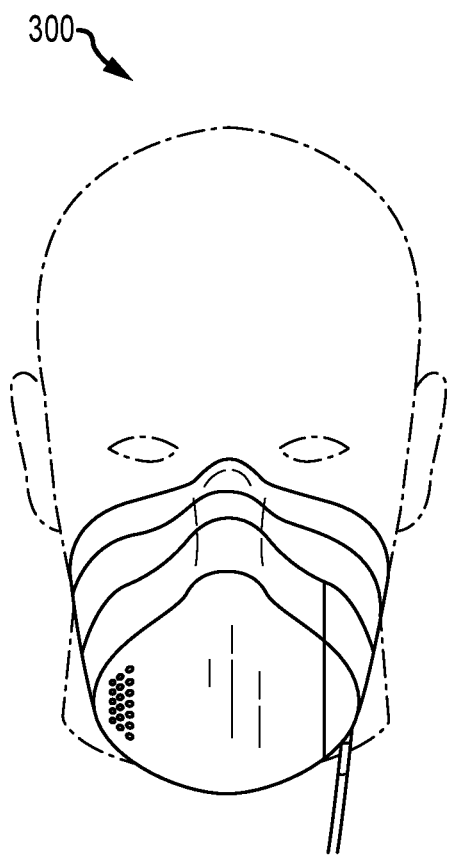
FIG. 48C is a front view of the electro-ionic device from FIG. 48A.
Figure 49A:
FIG. 49A is a perspective view of an electro-ionic device according to an exemplary embodiment of the present disclosure.
Figure 49B:
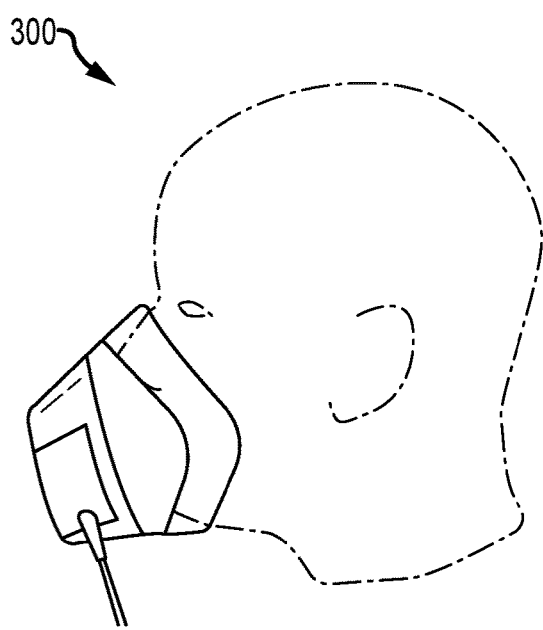
FIG. 49B is a side view of the electro-ionic device from FIG. 49A.
Figure 49C:
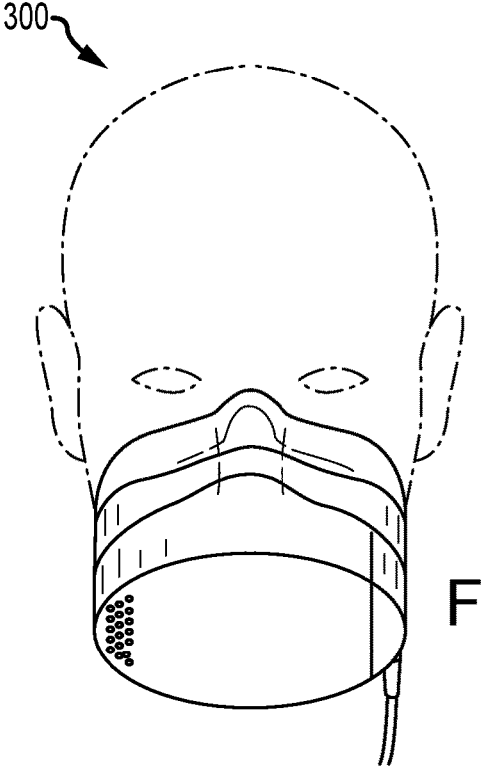
FIG. 49C is a front view of the electro-ionic device from FIG. 49A.
Figure 50A:
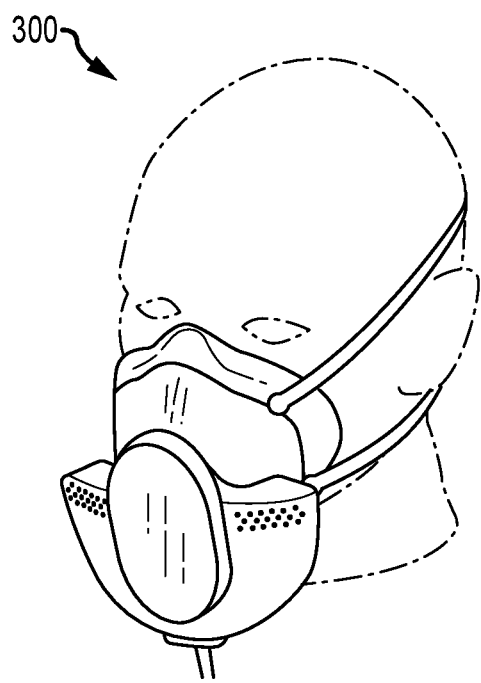
FIG. 50A is a perspective view of an electro-ionic device according to an exemplary embodiment of the present disclosure.
Figure 50B:
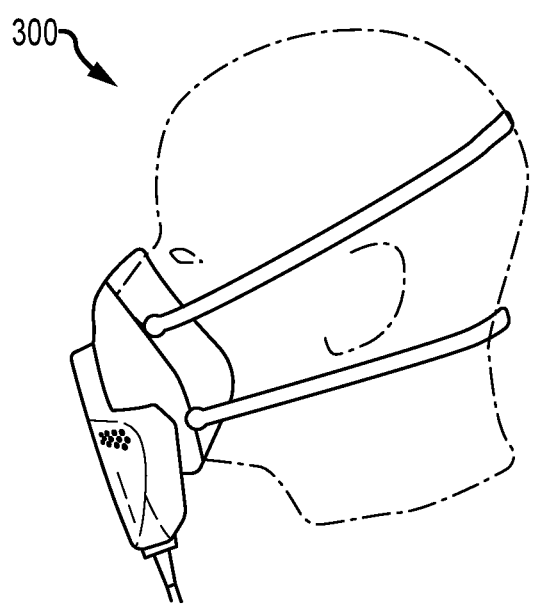
FIG. 50B is a side view of the electro-ionic device from FIG. 50A.
Figure 50C:
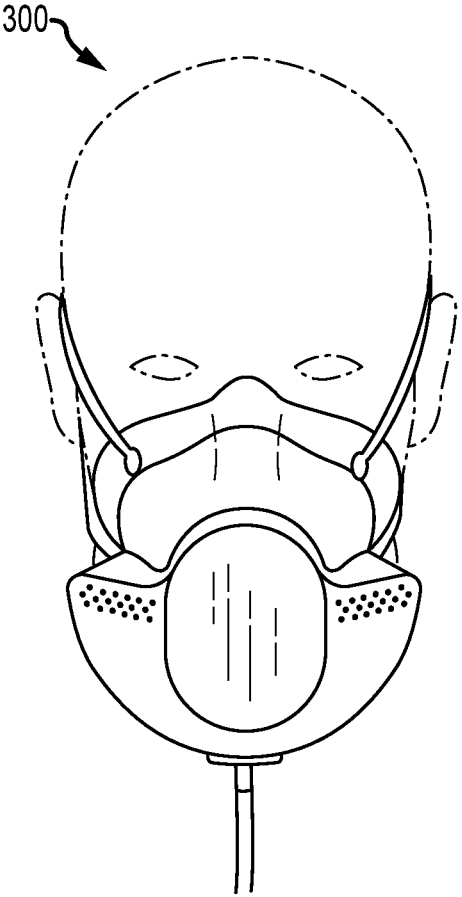
FIG. 50C is a front view of the electro-ionic device from FIG. 50A.
Figure 51A:
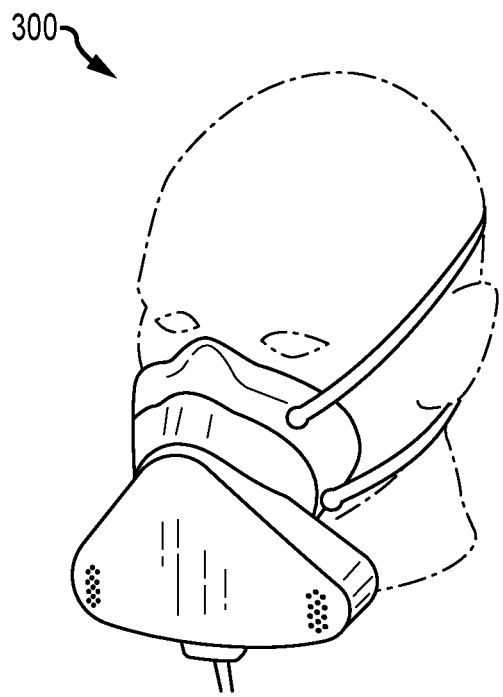
FIG. 51A is a perspective view of an electro-ionic device according to an exemplary embodiment of the present disclosure.
Figure 51B:
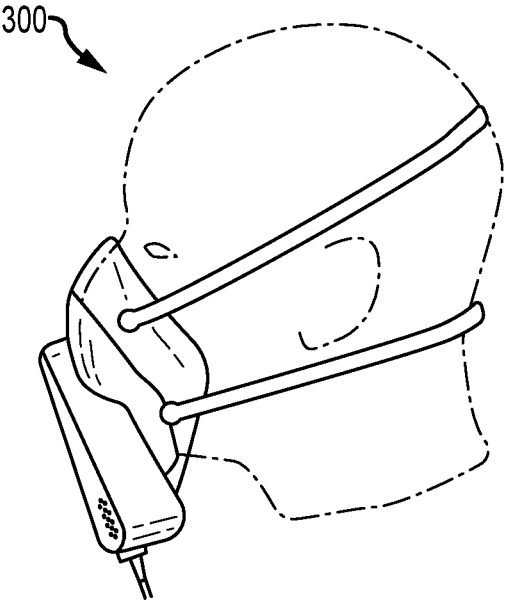
FIG. 51B is a side view of the electro-ionic device from FIG. 51A.
Figure 51C:
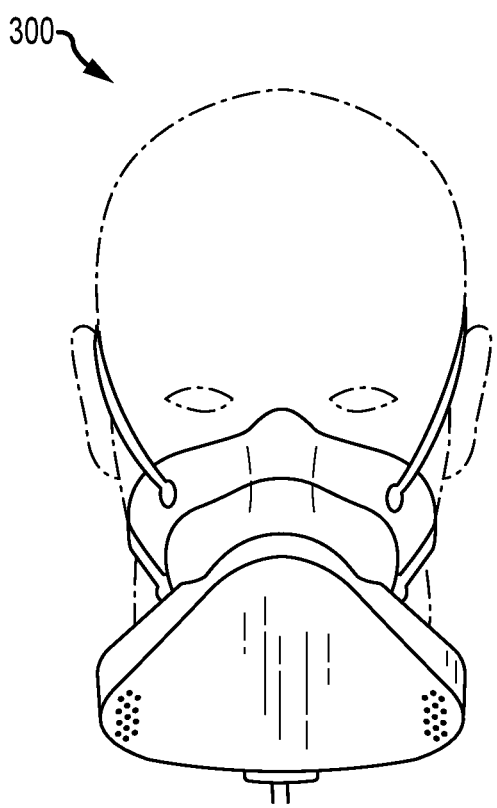
FIG. 51C is a front view of the electro-ionic device from FIG. 51A.
Figure 52A:
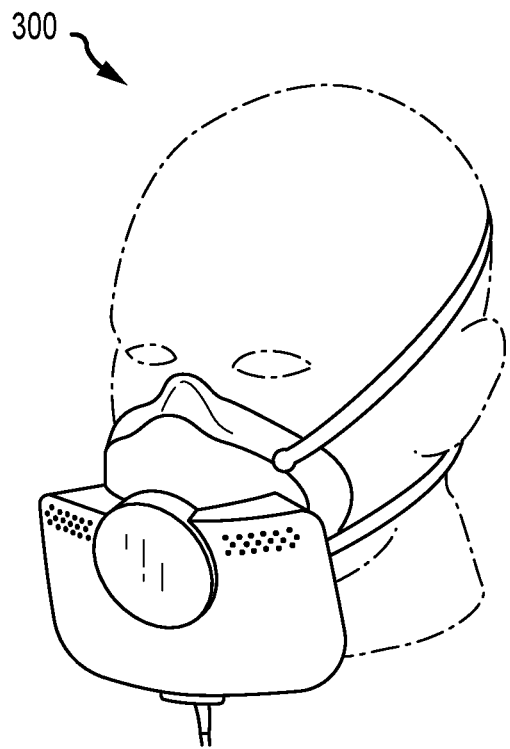
FIG. 52A is a perspective view of an electro-ionic device according to an exemplary embodiment of the present disclosure.
Figure 52B:
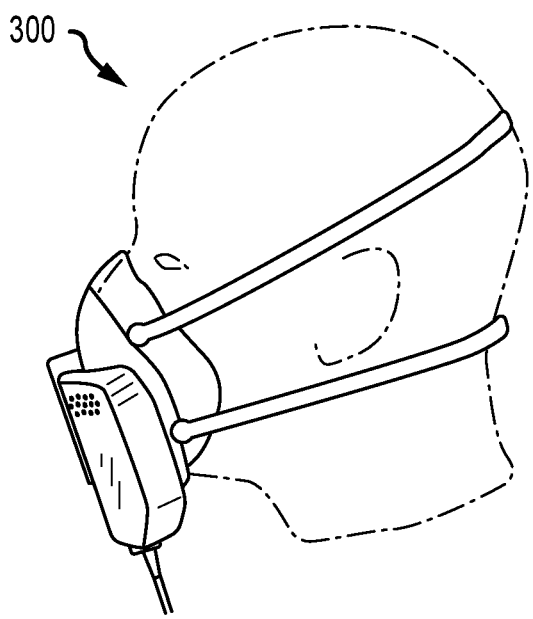
FIG. 52B is a side view of the electro-ionic device from FIG. 52A.
Figure 52C:
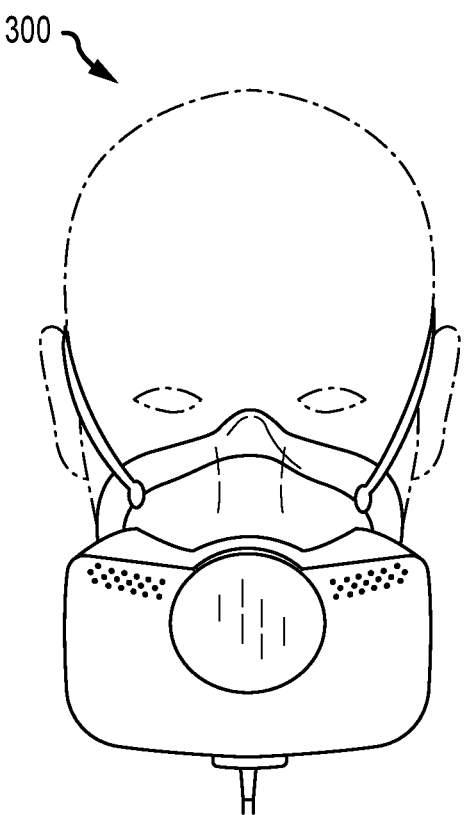
FIG. 52C is a front view of the electro-ionic device from FIG. 52A.

FIGS. 45A and 45B also show another embodiment the electro-ionic device 300 similar to the embodiment shown in FIGS. 43A-43C with a different housing 302 and offering similar benefits and features.

Embodiments of the electro-ionic device 300 shown in FIGS. 46A-46C, 47A-47C, 48A-48C, 49A-49C, 50A-50C, 51A-51C, and 52A-52C are similar to the embodiment shown in FIGS. 43A-43C with differently sized and shaped housings 302.

Figure 53:
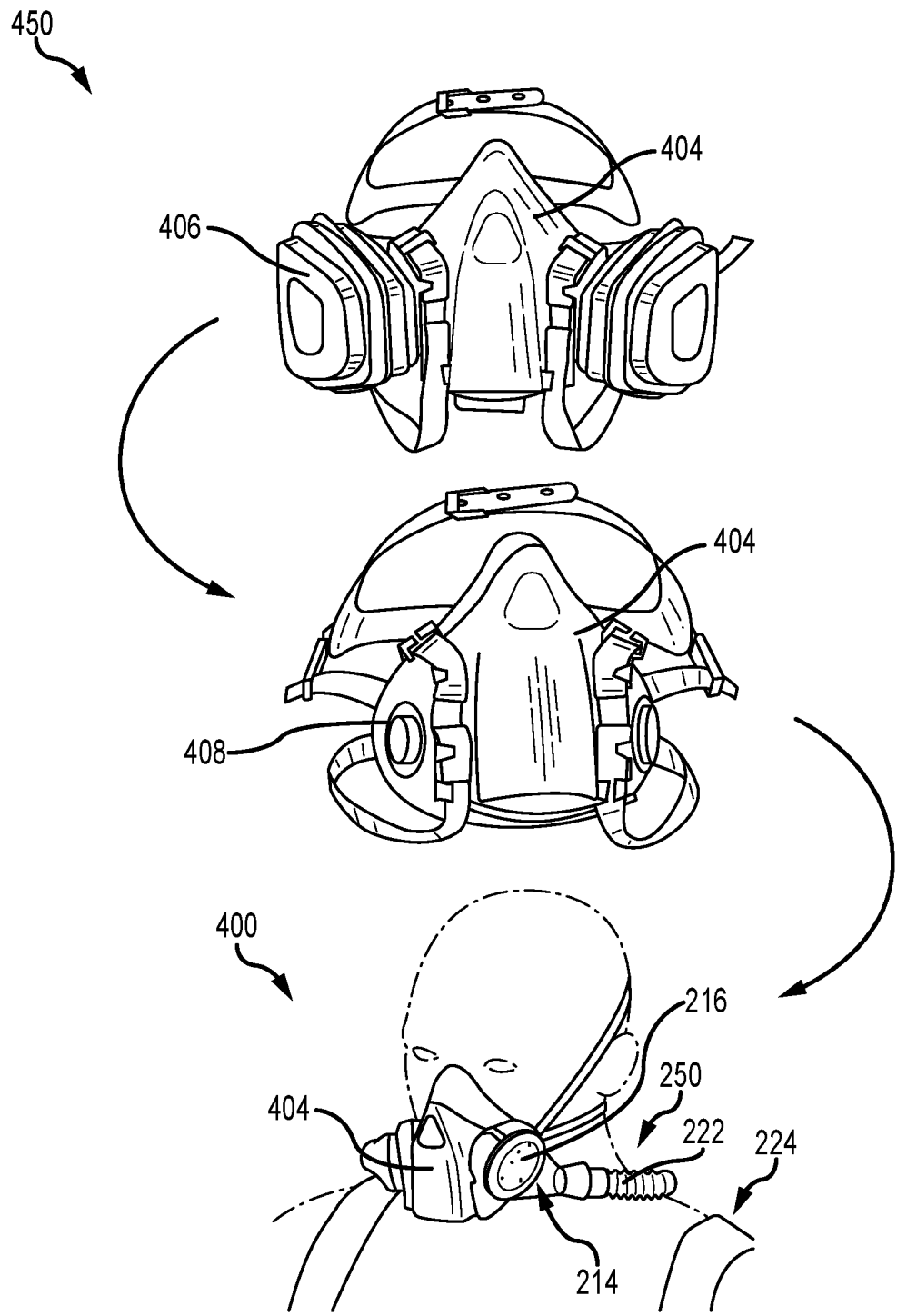
FIG. 53 is perspective diagram showing an electro-ionic device in various states.

FIG. 53 shows an exemplary embodiment of an electro-ionic device 400 and system 450. The system 450 may comprise a mask 404 having filter cartridges 406 that are interchangeable with the ionization filter 250 and associated tubing 222, electronics unit 224, etc. similar to the embodiment shown in FIG. 17. In particular, the mask 404 may have openings 408 configured to fit disposable filter cartridges 406 in a first configuration. The cartridges 406 may be removed from the mask and replaced with and the valves 220, filtrate layer 216, opening 214 and tubing 222 which may connect to an ionization filter 250 carried remotely on a user's back, for example. In other words, the ionization filter 250 may be adapted to work with currently marketed masks 404 configured for employing disposable filter cartridges 406.

Figure 54:
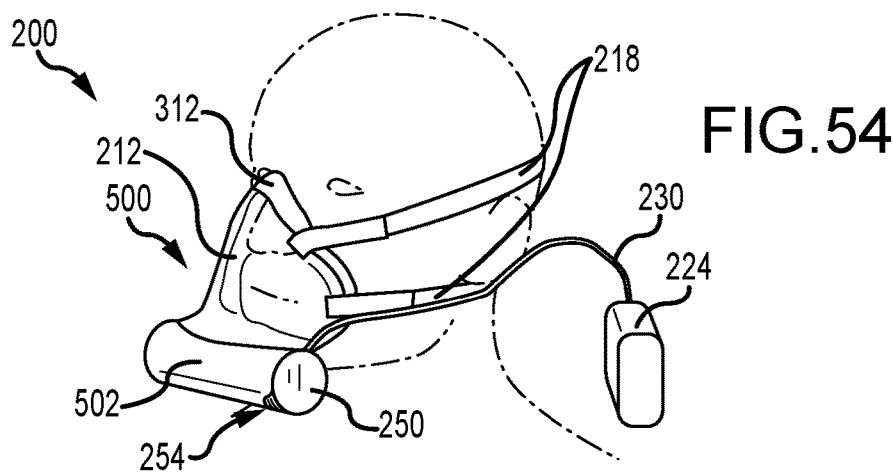
FIG. 54 is a perspective view of an electro-ionic device.
Figure 55:
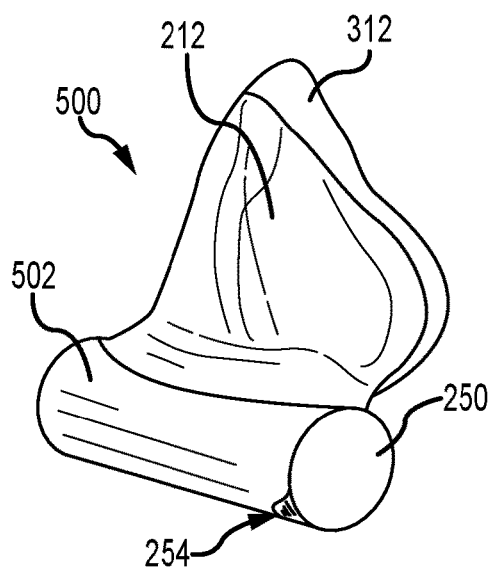
FIG. 55 is a front a top-front perspective view of a mask assembly of the electro-ionic device of FIG. 54.

FIGS. 54-60 illustrate various views of another embodiment of the electro-ionic device 200 and its various components, wherein the embodiment includes a modular ionization filter that is removable from the rest of the electro-ionic device for cleaning/sanitizing purposes. As shown in FIG. 54, the electro-ionic device 200 includes a mask assembly 500 coupled to the user via straps 218. The electronics unit 224 is separate from the mask assembly 500 and coupled to the mask assembly 500 via the cable 230.

Figure 56:
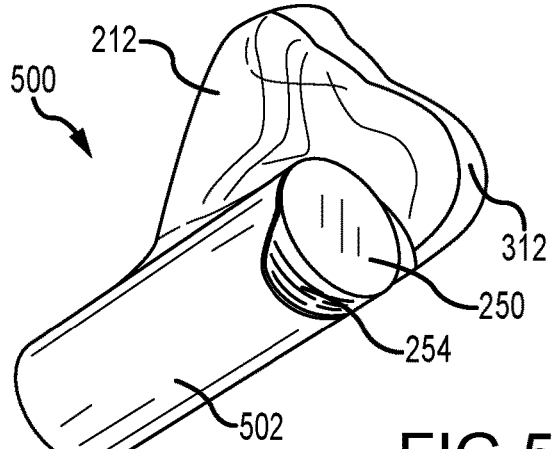
FIG. 56 is a bottom-front perspective view of the mask assembly of FIG. 55.
Figure 57:
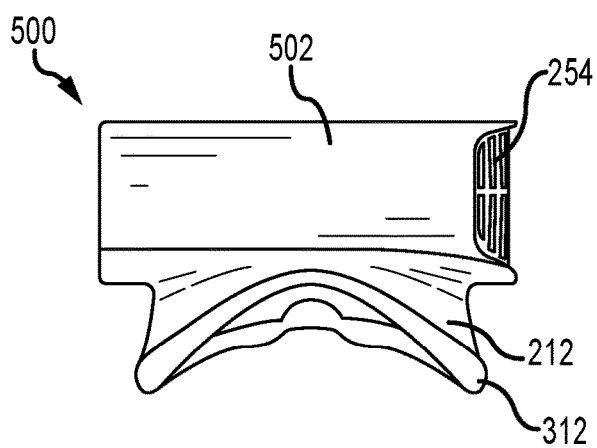
FIG. 57 is a bottom view of the mask assembly of FIG. 55.
Figure 58:
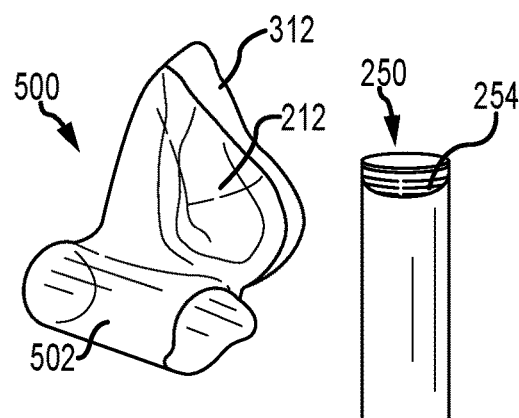
FIG. 58 is a top-front view of the mask assembly of FIG. 55 with the modular ionization filter removed from the mask, thereby allowing the ionization filter to be sanitized separately from the rest of the mask assembly.

As illustrated in FIGS. 56-57, the mask assembly 500 includes the mask 212 with an integrally formed receptacle 502 in which the ionization filter 250 is removably received, as shown in FIG. 58, thereby allowing the ionization filter 250 to be separately washed/cleaned/sanitized from the rest of the mask assembly 500. The mask 212 also includes the gasket 312 as described above in detail with respect to other embodiments.

Figure 59:
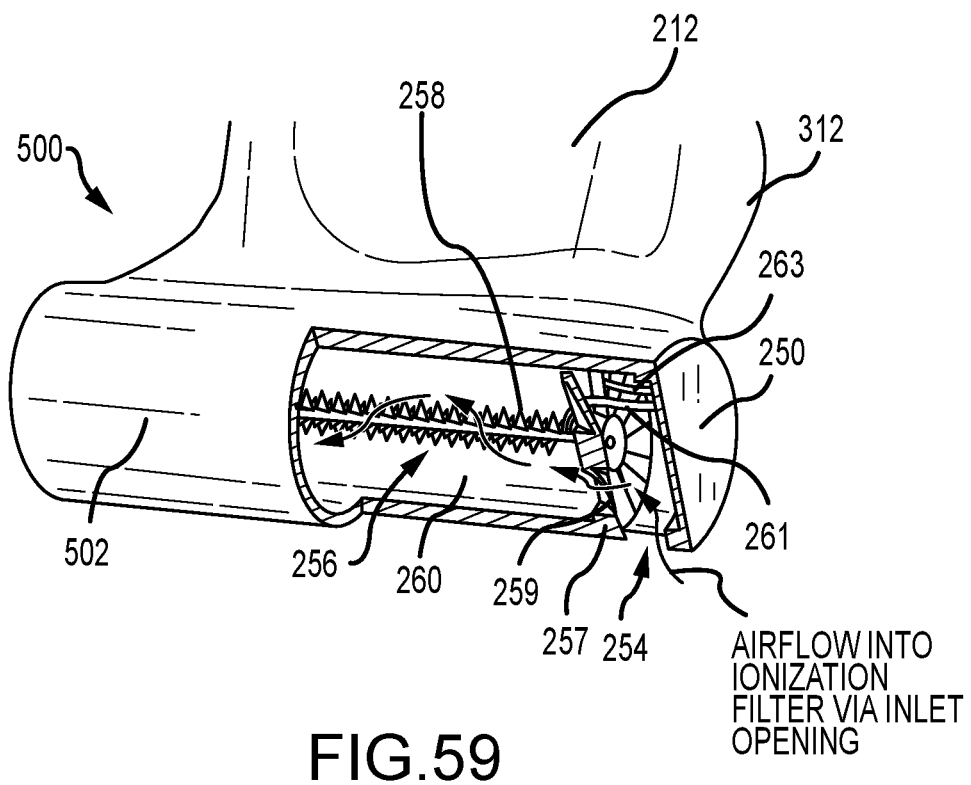
FIG. 59 is an enlarged cutaway view of the ionization filter of the view depicted in FIG. 54.
Figure 60:
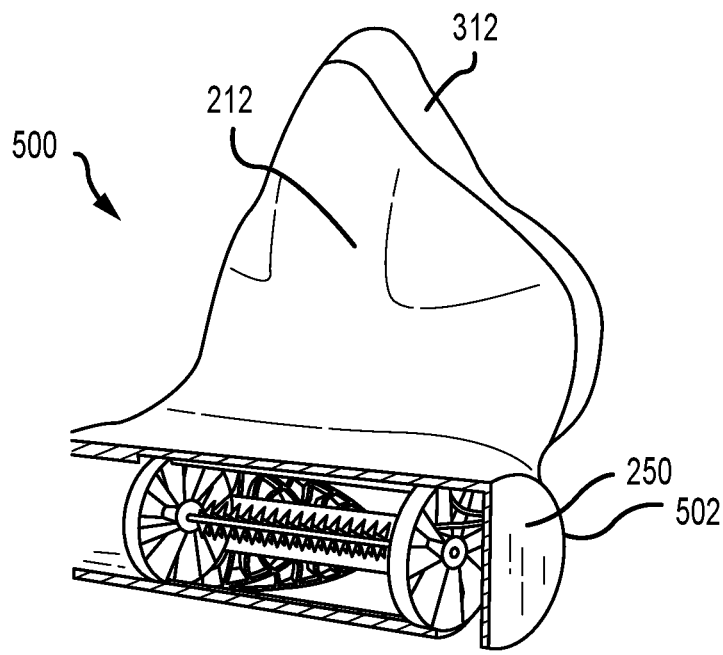
FIG. 60 is the same view as FIG. 59, except the ionization filter is more fully sectioned to show more of its interior, the interior being the same as shown in FIG. 9B.

FIG. 59 is an enlarged cutaway view of the ionization filter of the view depicted in FIG. 54, and FIG. 60 is the same view as FIG. 59, except the ionization filter is more fully sectioned to show more of its interior. A comparison of FIGS. 9B and 60 make it clear that the internal components of the ionization filters depicted in these two figures are identical, including the emitter 256, collector 260, spiral vanes 259 of the spacers 257 and conductors 261, 263 leading to the emitter 256 and collector 260. Therefore, the discussion of these components as discussed above with respect to FIG. 9B is applicable to what is depicted in FIG. 60 and will not be repeated here.

As shown in FIG. 59, upon inhalation by the wearer of the mask 221, contaminated air from the surrounding environment enters the opening 254 and passes through the spiral spacer 257. The vanes 259 of the spiral spacer cause the airflow to spiral through the chamber of the ionization filter 250 as the airflow moves along the length of the emitter 256 between the collector 260 and the emitter 256. This spiraling of the airflow within the chamber increases the dwell time of the airflow in the chamber, allowing increased exposure to the emitter and collector than would otherwise be possible for a chamber of such reduced length. As discussed above, the emitter and collector work together to precipitate contaminates out of the airflow as the airflow spirals along the emitter.

It should be understood, that while the airflow spirals within the chamber on account of the spiral vanes 259 of the spacer 257, or may even be turbulent as opposed to laminar flow within the chamber, all of which serves to increase the dwell time of the airflow within the chamber, the general direction of airflow within the chamber is substantially, if not completely, parallel to the longitudinal axis of the emitter and collector, as can be understood the above discussion regarding Arrows C with respect to FIGS. 9A and 9B. Also, as depicted in FIGS. 9A and 9B, the offset distance (Arrow D) between the tips of the emitter and the collector are the same for the arrangement of the emitter and collector in the embodiments depicted in FIGS. 59 and 60.

As illustrated in FIG. 59, the inhalation spiral airflow eventually reaches an opening into the volume of the mask 212 (i.e., the mask space). At this point, the airflow has been filtered to protect the wearer of the mask 212 from any contaminates that entered the opening 254 of the ionization filter 250 and were precipitated out of the airflow in the chamber of the ionization filter 250. As discussed above, tested filtration rates for this ionization filter 250 have been 99.8% viral penetration reduction in the context of a COVID-19 aerosol study with COVID-19 aerosol concentrations at much higher levels than would ever be encountered in real life.

Still referring to FIG. 59, depending on the embodiment and as can be understood from the above discussions regarding the various embodiments of the elector-ionic device 200, upon exhalation by the wearer of the mask 212, exhaled airflow contaminated by the wearer may be ported from the mask volume directly outside the mask without further ionization filtration, a one-way valve preventing reverse flow back into the inhalation ionization filter 250. Alternately, the exhaled air may be routed through a second or exhalation ionization filter for similar filtration as already described before the exhaled air reaches the surrounding environment, a one-way valve again preventing reverse flow back into the inhalation ionization filter 250.

Finally, in the specific embodiments depicted in FIGS. 54-60, the ionization filter 250 serves to filter both for inhalation and exhalation. In doing so, the exhaled airflow may simply reverse direction back through the ionization filter 250 to be filtered before exiting the opening 254 into the surrounding environment as filtered exhaled air. As discussed above with respect to similar embodiments where a single ionization filter 250 serves double duty for inhalation and exhalation, sensors identify periods of inhalation versus exhalation and modulates the voltage such that ozone levels are lower upon inhalation and higher upon exhalation.

FIGS. 64 and 65 illustrate partially exploded views of another embodiment of the mask assembly 800 and its various components for use in an electro-ionic device 200 in a similar manner as the mask assembly 500 discussed above. The mask assembly 800 is similar to mask assembly 500 except for the differences discussed below.

Referring to FIGS. 64 and 65, the mask assembly 800 includes a porous Faraday cage 802 that encapsulates the emitter 256 and the collector 260. The porous Faraday cage 802 may include a solid shell 804 having a hollow inside and porous filters 810 at each end of the solid shell 804. The solid shell 804 may be formed from one or more conductive materials such as a metallic or carbon fiber tube or foil, conductive paint, and/or conductive plastic, such as, for example, polyacetylene, polypyrrole, polyindole and polyaniline among others. As shown in FIG. 64, the solid shell 804 may form an outer radial portion of the housing of the ionization filter 250 such as being formed from a conductive plastic or resin, whereas an inner portion of the housing may be formed from a non-conductive plastic or resin to space and insulate the solid shell 804 from the collector plate 260. The solid shell 804 may include a cylindrical portion 804 and a radially inwardly protruding edge 808 that connects the cylindrical portion 804 to a cylindrical inner surface of the housing of the ionization filter 250. In other embodiments not shown, the housing of the ionization filter 250 may be formed from multiple segments such as a center section and two end sections, the outer surface and sides of the center section may be covered with a conductive paint or foil and when the housing sections are mechanically coupled together, the conductive paint or foil on the outer surface electrically communicates with an inner surface of the housing.

Each of FIGS. 64 and 65 illustrate porous filters 810 axially exploded from the solid shell 804 along a common longitudinal axis A. The porous filters 810 may be similar to filtrate layer 106 discussed above, such as a non-conductive fibrous mesh infused with electrically conductive materials, including conductive wires. The porous filter 810 may be comprised of mesh of conductive materials without a non-conductive mesh. The conductive material in the porous filter 810 may comprise alloys or oxides containing nickel, chromium, manganese, cobalt, iron, copper, platinum, silver, rhodium, cerium or combinations thereof to assist in the decomposition of ozone. Furthermore, the porous filter 810 may contain any electrically conductive material to form the end caps of the Faraday cage 802 such as copper, aluminum, steel alloys, etc. and an ozone decomposition material, such as the alloys or oxides listed above, to assist in the decomposition of ozone. In some embodiments, the electrically conductive material and the decomposition material are in electrical communication with one another and in other embodiments, they are not. The porous filter 810 may be tightly meshed, but with pore sizes large enough to allow breathing therethrough without significant resistance to airflow. For example, the porous filter 810 may have an electrically conductive mesh having a pore size between 1 μm and 5 mm, preferably between 10 μm and 2.5 mm, more preferably between 100 μm and 2.0 mm, and even more preferably between 1 mm and 2 mm. It has been found that filtrate pore sizes less than 2.5 mm may effectively reduce voltage creep and clearance and thereby improve the safety of the mask assembly 800. In addition, the porous filter 810 may also include conductive foil or a plate 814 at outer axial ends of the porous filter 810 to further improve the efficacy of the Faraday cage 802.

Referring to FIG. 64, the housing of the ionization filter 250 may include cavities 812 in front of and behind the front and back spacers 257, respectively. Each of the cavities 812 includes the cylindrical inner surface from the radially inwardly protruding edge 808 and is configured to house the porous filter 810. When the porous filters 810 are positioned inside the cavities 812, the porous filter 810 makes electrical contact with the inwardly protruding edge 808 along its perimeter to form the Faraday cage 802 and completely surround the emitter 256 and the collector 260. The emitter 256 may be electrically connected to the Faraday cage 802 resulting in a common voltage potential therebetween. The first and last electrode 258 of the emitter 256 may be axially spaced farther apart from respective porous filters 810 than their radial distance to the collector plate 260.

Figure 66:
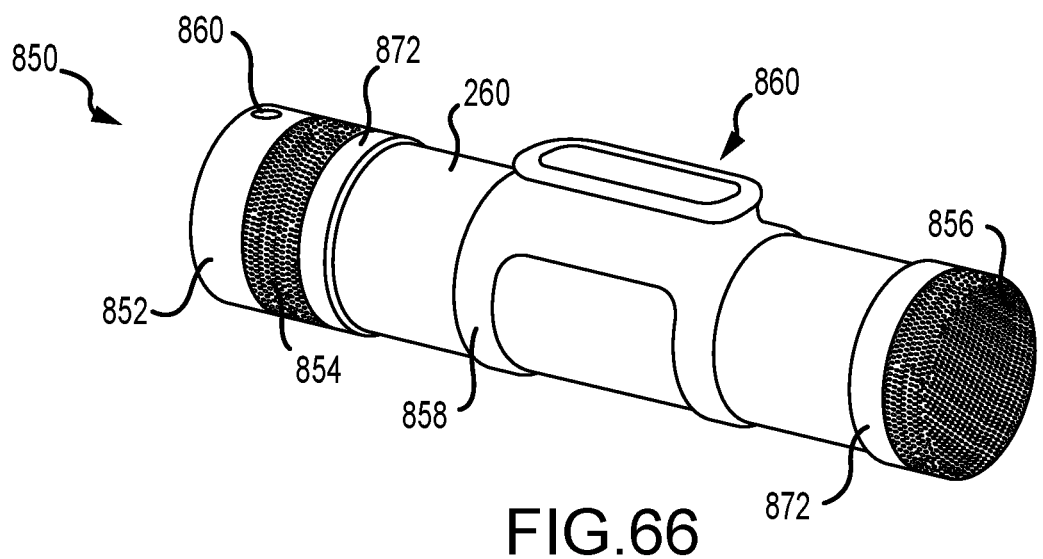
FIG. 66 is a perspective view of an ionization filter configured to be used in an electro-ionic device.
Figure 67:
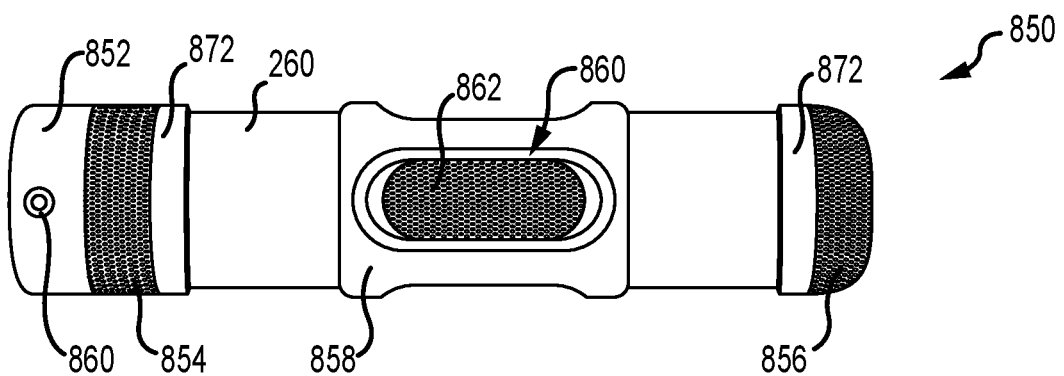
FIG. 67 is a top view of the ionization filter shown in FIG. 66.

FIGS. 66-69 illustrate another embodiment of an ionization filter 850 for use in an electro-ionic device, such as electro-ionic device 200, 300, 400, or 500, but instead of ionization filter 250. With reference to FIGS. 66 and 67, the ionization filter 850 includes the collector plate 260 electrically connected to first and second conductive porous filters 854 and 856 and conductive end cap 852 collectively forming a Faraday cage that encapsulates the emitter 256. The first conductive porous filter 854 may be cylindrically shaped having a first circular edge contiguous with a circular edge of the conductive end 852 and a second circular edge contiguous with a threaded collar 872 having inwardly facing threads. The second conductive porous filter 856 may be dome-shaped or partially spherical and may have a circular edge contiguous with a threaded collar 872, also having inwardly facing threads. The threaded collars 872 of the first and second porous filters are configured to threadedly engage corresponding outwardly threaded portions 870 of the collect plate 260 for assembly and disassembly.

The first and second porous filters 854 and 856 may be comprised of mesh of conductive materials without a non-conductive mesh. The conductive material in the porous filters 854 and 856 may comprise alloys or oxides containing nickel, chromium, manganese, cobalt, iron, copper, platinum, silver, rhodium, cerium, or combinations thereof to assist in the decomposition of ozone. Furthermore, the porous filters 854 and 856 may contain any electrically conductive material such as copper, aluminum, steel alloys, etc. and an ozone decomposition material, such as the alloys or oxides listed above, to assist in the decomposition of ozone. In some embodiments, the electrically conductive material and the decomposition material are in electrical communication with one another and in other embodiments, they are not. The porous filters 854 and 856 may be tightly meshed, but with pore sizes large enough to allow breathing therethrough without significant resistance to airflow. For example, the porous filters 854 and 856 may have an electrically conductive mesh having a pore size between 1 μm and 5 mm, preferably between 10 μm and 2.5 mm, more preferably between 100 μm and 2.0 mm, and even more preferably between 1 mm and 2 mm. It has been found that filtrate pore sizes less than 2.5 mm may effectively reduce voltage creep and clearance and thereby improve the safety of the ionization filter 850.

In addition to airflow through the porous filters 854 and 856, the ionization filter also includes an opening 860 in a mouthpiece portion 858 configured to interface with an opening in the mask 212 (not shown) or a mouthpiece assembly (not shown). The opening 860 may include a mouthpiece filter 862 configured to help reduce the amount of or prevent salivary fluids from entering the ionization filter. The mouthpiece filter 862 may comprise alloys or oxides containing nickel, chromium, manganese, cobalt, iron, copper, platinum, silver, rhodium, cerium, or combinations thereof to assist in the decomposition of ozone.

Figure 71:
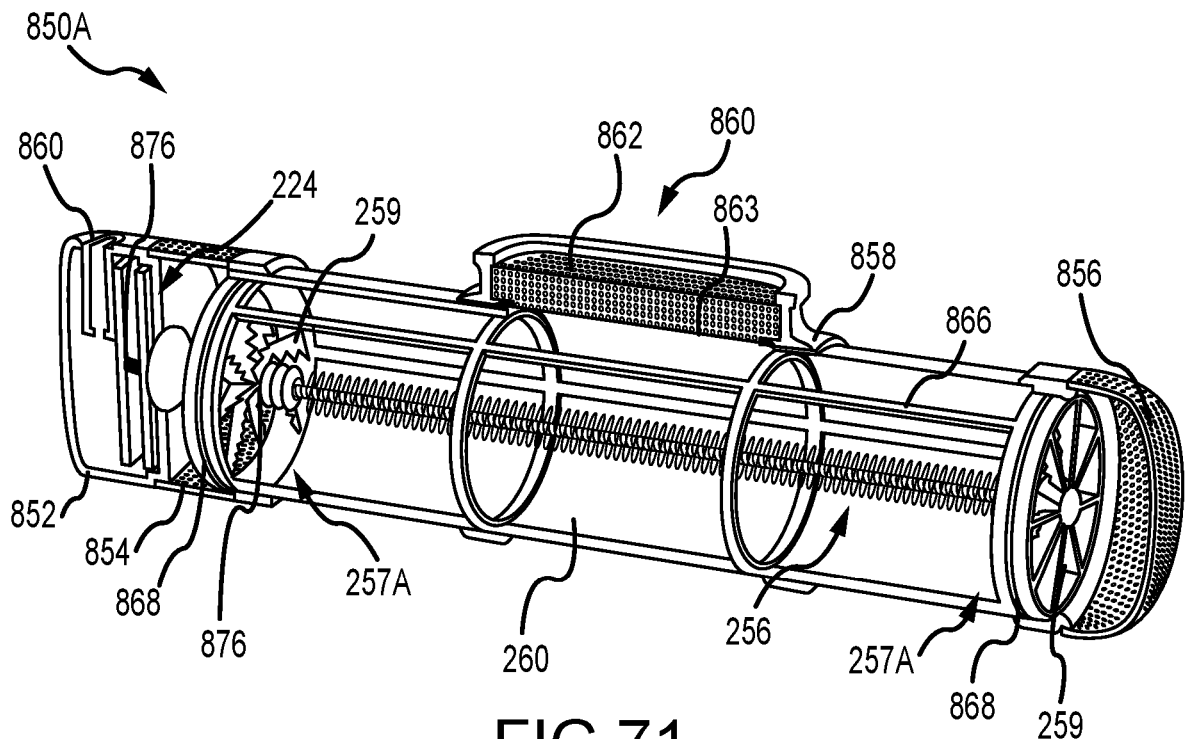
FIG. 71 is a sectional perspective view of an ionization filter configured to be used in an electro-ionic device.
Figure 72:
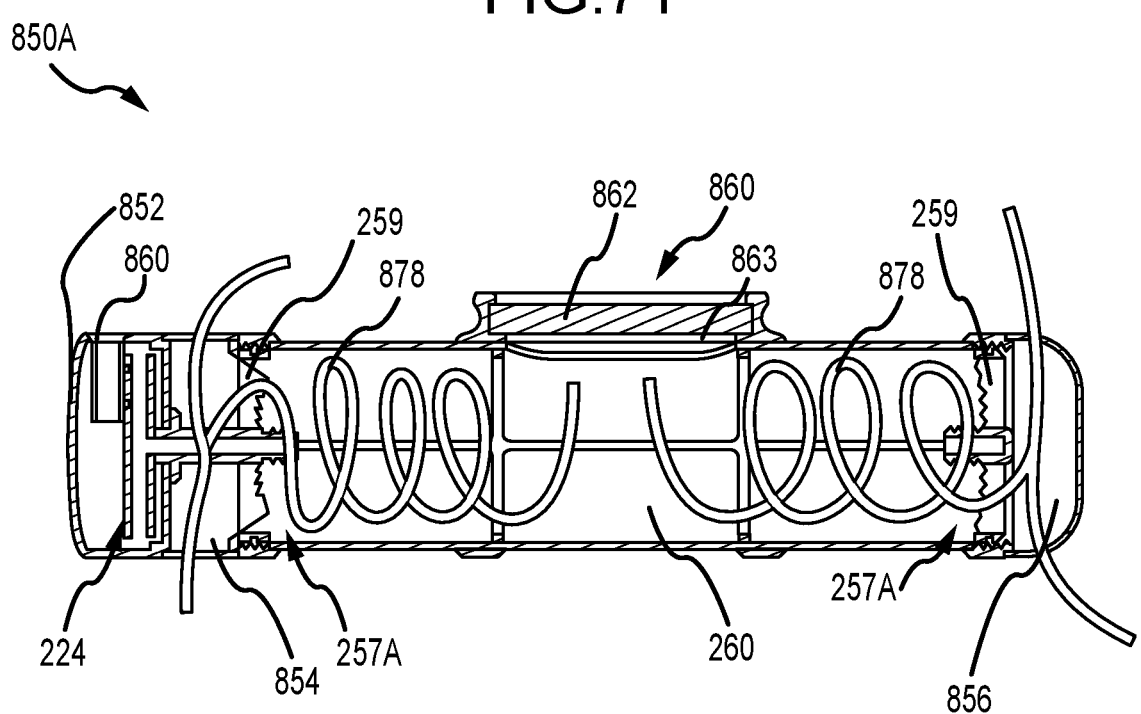
FIG. 72 is a sectional front view of the ionization filter from FIG. 71.

Beneath the mouthpiece filter 862 is a conductive porous filter 863 in electrical communication with the collector plate 260 along the perimeter of the porous filter 863 (FIGS. 71 and 72). In some embodiments the mouthpiece filter 862 may be electrically connected to the collector plate 260.

Figure 68:
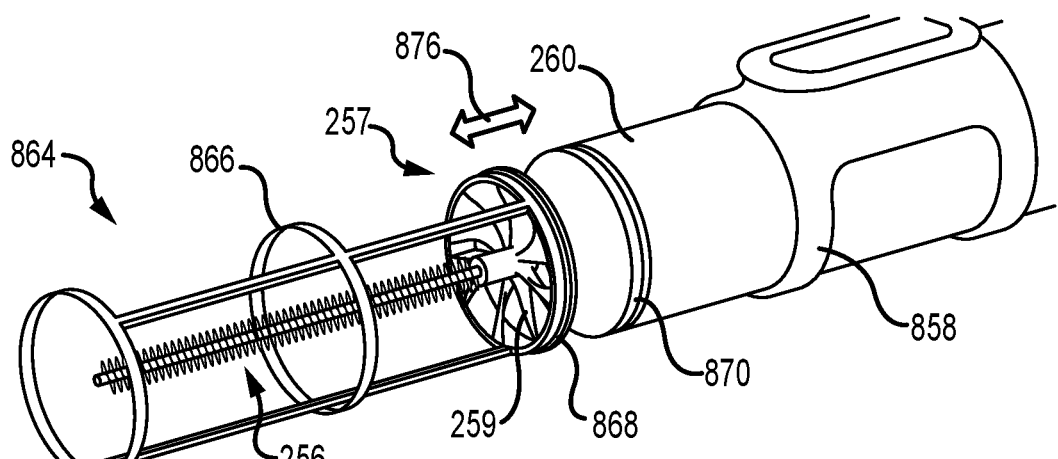
FIG. 68 is a perspective view of a portion of the ionization filter from FIG. 66 shown during removal/insertion of an emitter subassembly.
Figure 69:
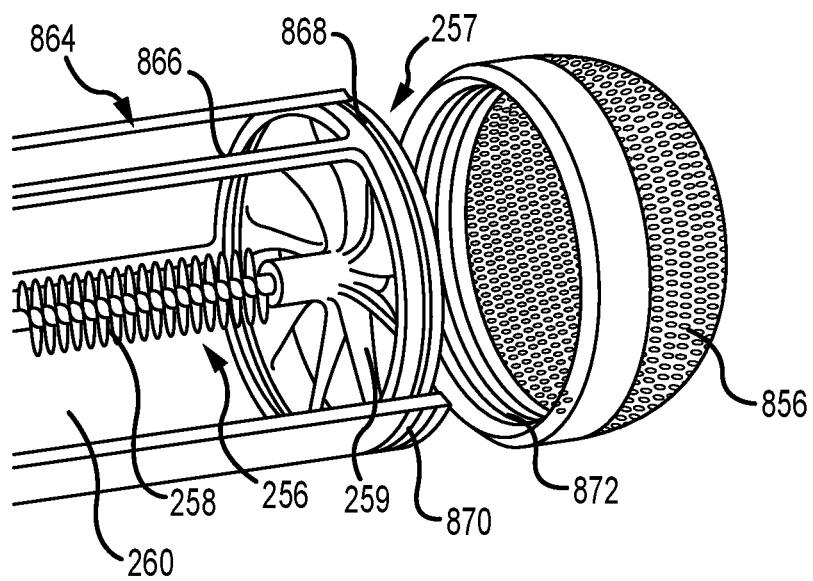
FIG. 69 is a partially-exploded, partially-sectional perspective view of a portion of the ionization filter from FIG. 66.

As shown in FIGS. 68 and 69, the emitter 256 is housed at the axial center of the collector plate 260. The emitter 256 and collector plate 260 operate in substantially the same manner as discussed above in electro-ionic device 200, 300, 400, or 500. The emitter 256 may be held at the axial center by the spacers 257 at first and second axial ends of the ionization filter. The spacers 257 may have spiral vanes 259 that spiral the airflow, or at least cause turbulence of the airflow to help extend the effective length of the airflow within the collector 260 to achieve greater dwell time of the airflow and its particles within the collector to increase the probability that the particles will be pulled from the airflow and attached to the collector 260.

An O-ring 868 may be positioned on an outwardly facing cylindrical surface of the spacer 257 which may function as an insulator to keep the wheel 257 spaced apart from direct contact with collector plate 260. The spacers 257 may be held apart from each other by a frame 866 such that the spacers 257, the frame 866, the emitter 256, and the O-ring 868 may collectively form an emitter assembly 864. As shown in FIG. 68, the emitter assembly 864 may be inserted into or removed from the collector plate 260 along the axial direction 876 for cleaning or replacement.

Figure 70:
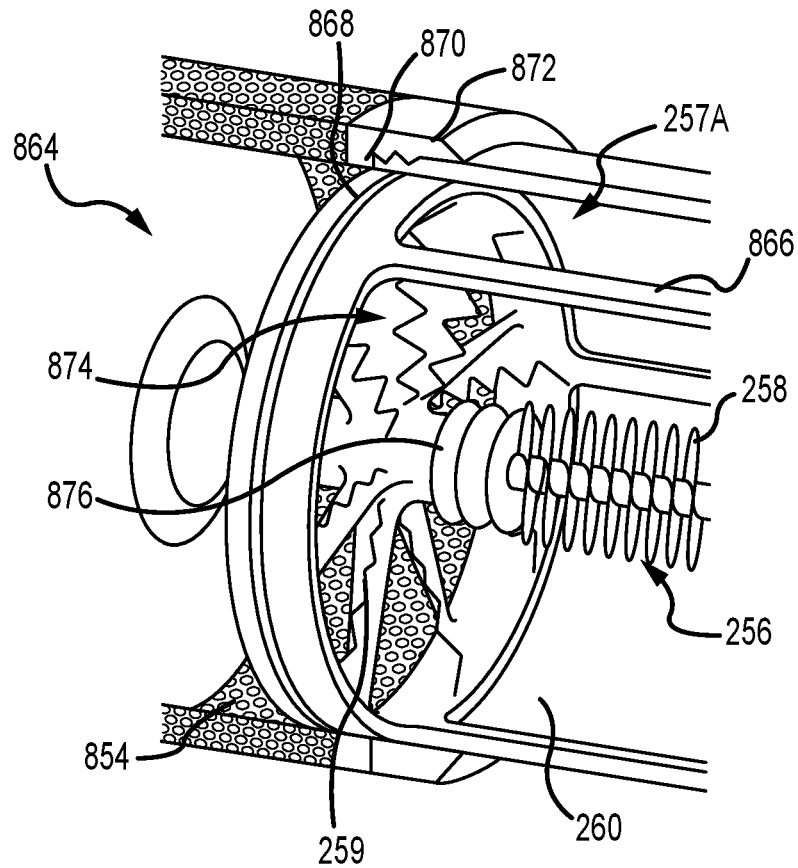
FIG. 70 is a partially-exploded, partially-sectional perspective view of an emitter subassembly.

FIG. 70 depicts another spacer 257A similar to spacer 257, but with the differences as follows. The spacer 257 includes a sawtooth profile 874 on the downwind (during inspiration) edges of the vanes 259. The sawtooth profile 874 may help convert the inhaled airflow into turbulent flow to help further increase the dwell time. The spacer 257A may also include an axial extension 276 extending from the spacer axially inward and having radial protrusions extending radially outward to help further reduce voltage creep from the emitter 258 and consequently, reduce electrical inefficiencies to improve performance and battery life.

FIGS. 71 and 72 show another embodiment of an ionization filter 850A substantially the same as ionization filter 850 but with spacer 257A instead of spacer 257. FIG. 72 shows an airflow pathway 878 through the ionization filter 850A in which, due to the geometry of the spacers, the airflow may spiral from each side of the collector plate 260 and toward the opening 860. The spacers 257A may be oriented as mirror images of each other such that the airflow spirals along the airflow pathway 878 with each half being a mirror image of the other side. The airflow pathway 878 may be the same during inspiration and expiration, such that during inspiration, air flows in through the porous filters 854 and 856 and out through the mouthpiece filter 862, and during expiration, the air flows in through the mouthpiece filter 862 and out through the porous filters 854 and 856.

Figure 73A:
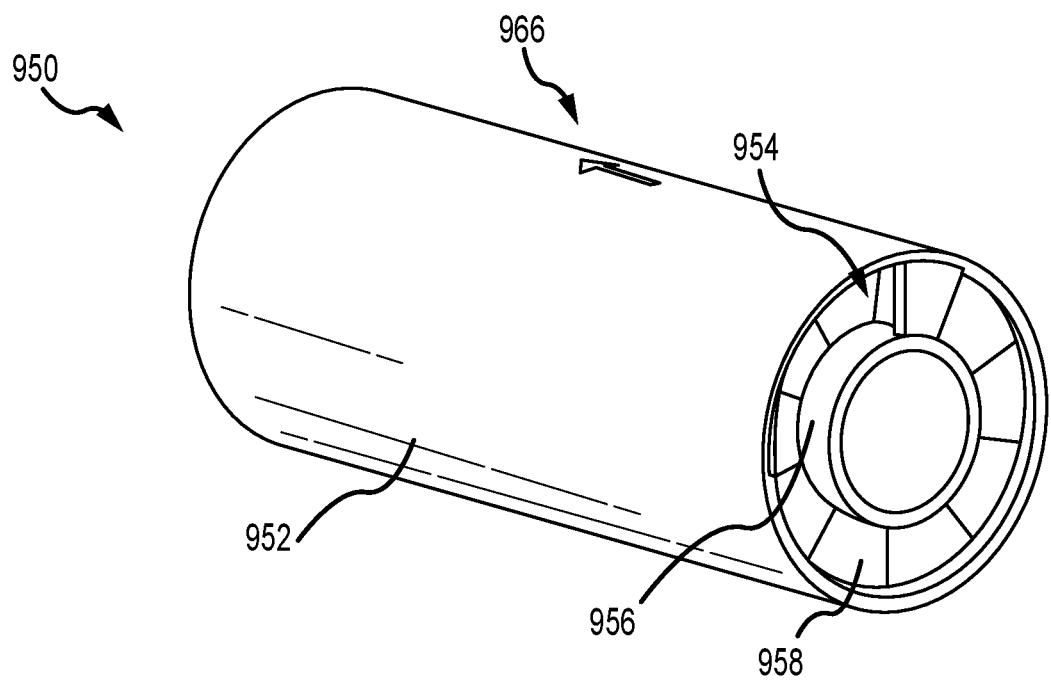
FIG. 73A is a perspective view of an ionization filter configured to be used in an electro-ionic device.
Figure 73B:
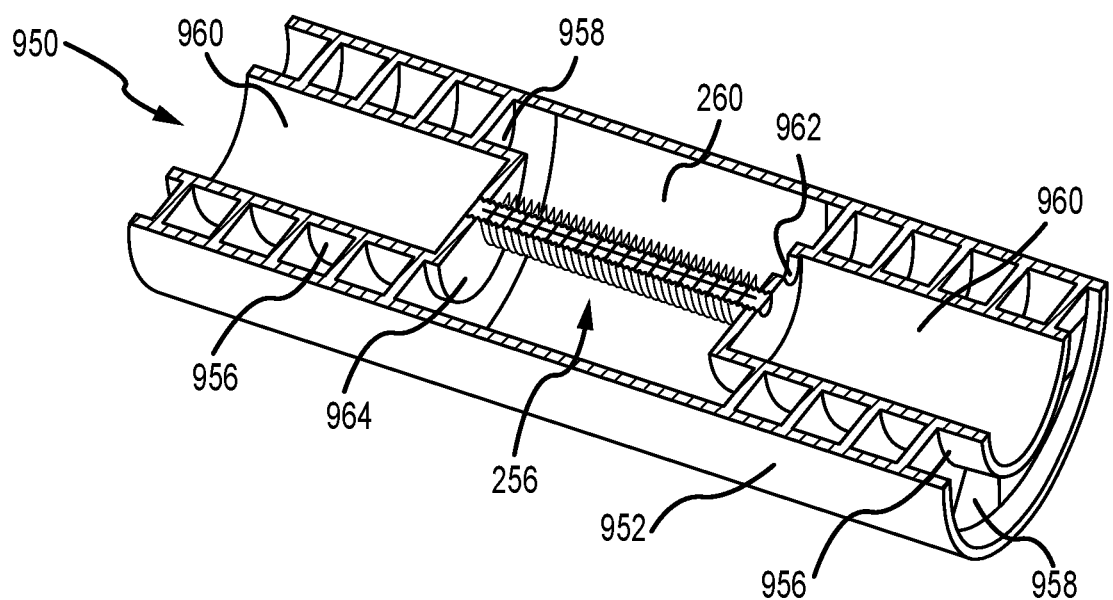
FIG. 73B is a perspective, sectional view of the ionization filter shown in FIG. 73A.
Figure 74A:
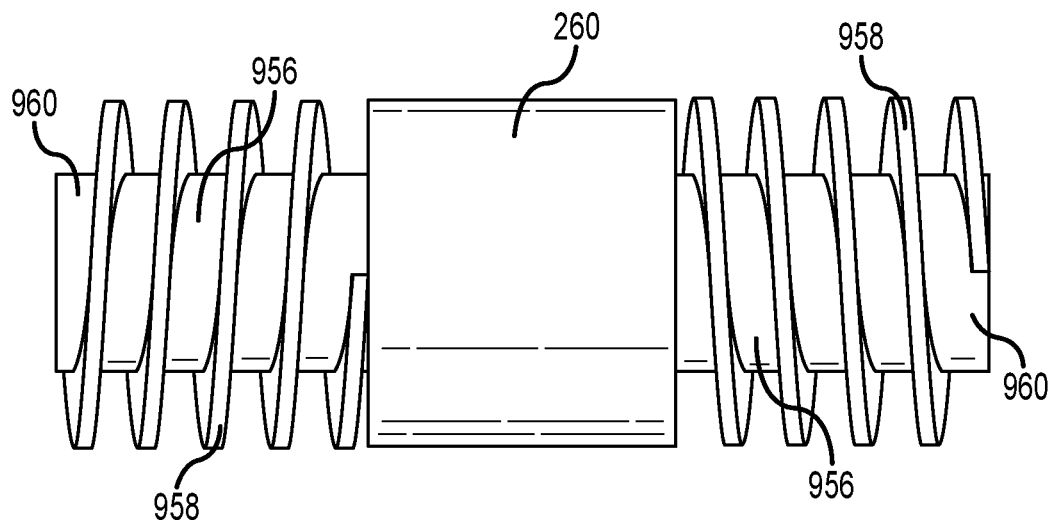
FIG. 74A is a front view of the ionization filter shown in FIG. 73A with an outer housing removed from view.
Figure 74B:
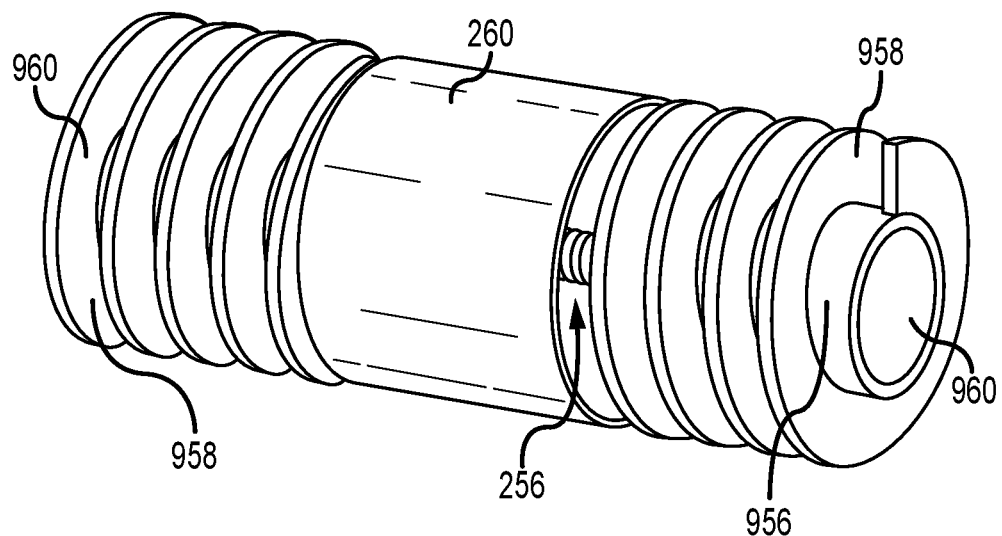
FIG. 74B is a perspective view of the ionization filter shown in FIG. 74A.
Figure 75A:
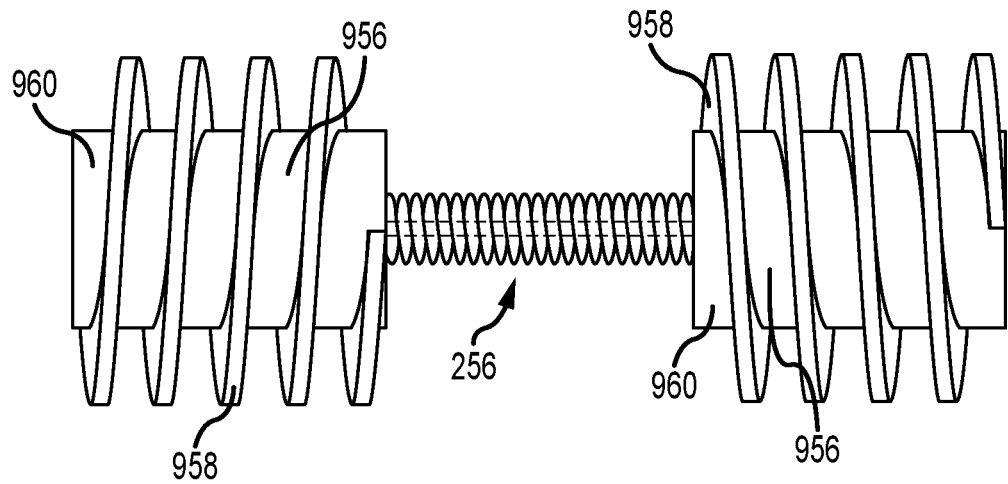
FIG. 75A is a front view of the ionization filter shown in FIG. 74A with a collector plate removed from view.
Figure 75B:
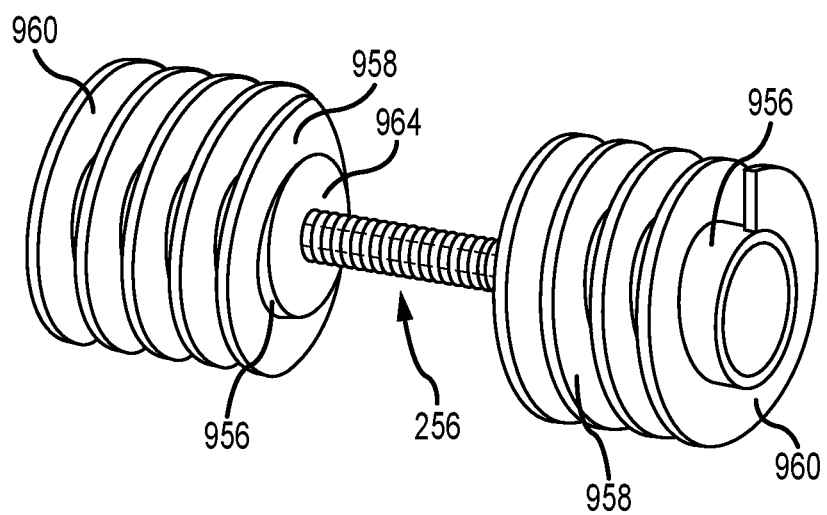
FIG. 75B is a perspective view of the ionization filter shown in FIG. 75A.

FIGS. 73A-73B illustrate another embodiment of an ionization filter 950 for use in an electro-ionic device, such as electro-ionic device 200, 300, 400, or 500, but instead of ionization filter 250. As with the Faraday cage 802 discussed above, the ionization filter 950 includes enhanced safety features. Specifically, the ionization filter 950 may include enhanced safety features to reduce voltage creep and clearance by increasing the minimum total distance an electron may potentially travel along a non-conductive surface or through the air between the emitter 256 to the user's body either upstream or downstream from the emitter 256.

Referring to FIG. 73A, a perspective view of the ionization filter 950 is shown. The ionization filter 950 may include an outer housing 952 that houses the internal components of the ionization filter 950, such as the emitter 256 and the collector plate 260, which are described above in more detail. The outer housing 952 is configured to be removably inserted into a receptacle of an electro-ionic device, such as receptacle 502 of electro-ionic device 500 (FIG. 58). To assist a user in the insertion, the outer housing 952 may include indicia 966 on its outer surface having insertion instructions, such as arrow showing the direction of insertion. The indicia 966 may be formed in the outer housing 952, printed on the outer housing 952, or printed on a sticker positioned on the outer housing 952.

As shown in FIG. 73B, each axial end of the outer housing 952 may include a spiral insert 960, which has a tubular sidewall 956 defining a cylindrical cavity along a longitudinal axis of the spiral insert 960. The spiral insert 960 may include a single thread 958 extending radially from the tubular sidewall 956 and helically wound along the tubular sidewall 956 from the axial outer end to a circular cap 964 which closes the cylindrical cavity at an inner axial position. In other embodiments, the spiral insert may include any number of threads 958, such as two, three, or four threads, for example. The circular cap 964 may include a central bore configured to hold the emitter 256 and allow a conductive wire from cable 230 (see FIG. 54) to connect the emitter 256 to the electronics unit 224 for providing a high voltage signal. The circular cap 964 may also include a bore 962 offset from the longitudinal axis for allowing a conductive wire from cable 230 to connect the collector plate 260 to the electronics unit 224.

In the embodiment shown in FIG. 73B, the thread 958 of the spiral insert 960 is configured to be threaded into a corresponding helical groove or thread formed in an inwardly facing surface of the outer housing 952. However, in other embodiments not shown, the spiral insert 960 may be formed integrally with the outer housing 952. In this embodiment, the outer housing 952 may be injected molded into two radial halves which are later rejoined during assembly. Returning to FIG. 73A, the axial outermost two overlapping portions of the thread 958 form an inlet 954 with the outer housing 952 to allow air to enter the ionization filter 950. The air is then guided by adjacent overlapping portions of the spiral insert 958 along a helical pathway advancing axially toward the emitter 256 and collector plate 260 in the central portion of the ionization filter 950. The helical pathway may cause spiral airflow, increased turbulence, or increased dwell time of airflow between the emitter 256 and the collector plate 260.

As better shown in FIGS. 74A-75B, the spiral inserts 960 may have opposing thread orientations, such as a clockwise thread from the inlet 954 to the central portion and a counter-clockwise thread from the central portion to an outlet (not shown). Thus, the airflow through the central portion is configured to reverse angular direction causing further turbulence, mixing, and increased dwell time between the emitter 256 and the collector plate 260. The spiral insert 960 between the user and the emitter 256 may comprise alloys or oxides containing nickel, chromium, manganese, cobalt, iron, copper, platinum, silver, rhodium, cerium, or combinations thereof to assist in the decomposition of ozone before the air enters the lungs of the user. In some embodiments, both spiral inserts 960 may comprise the aforementioned materials.

Figure 76:
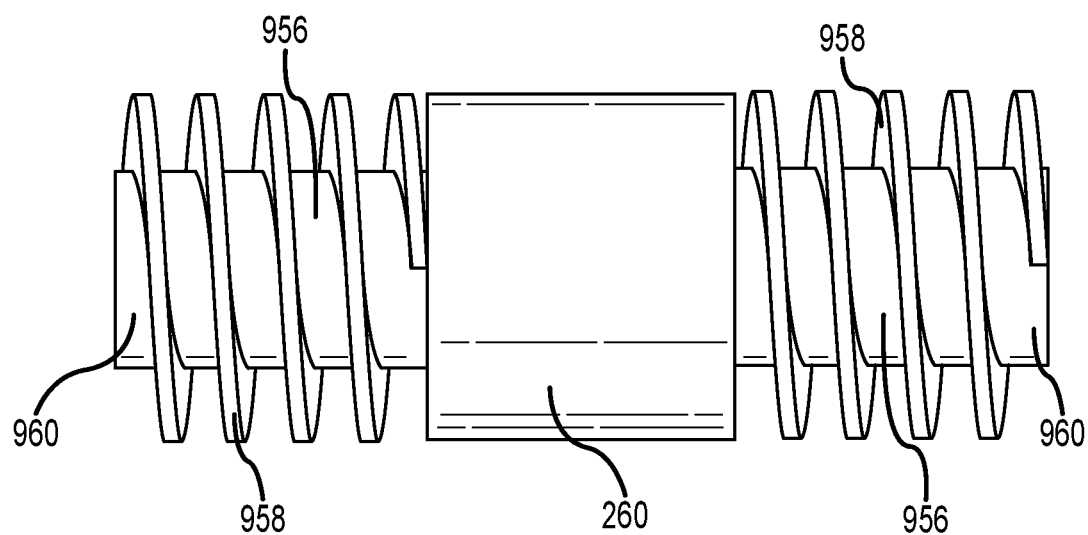
FIG. 76 is a front view of another ionization filter with an outer housing removed from view.
Figure 77:
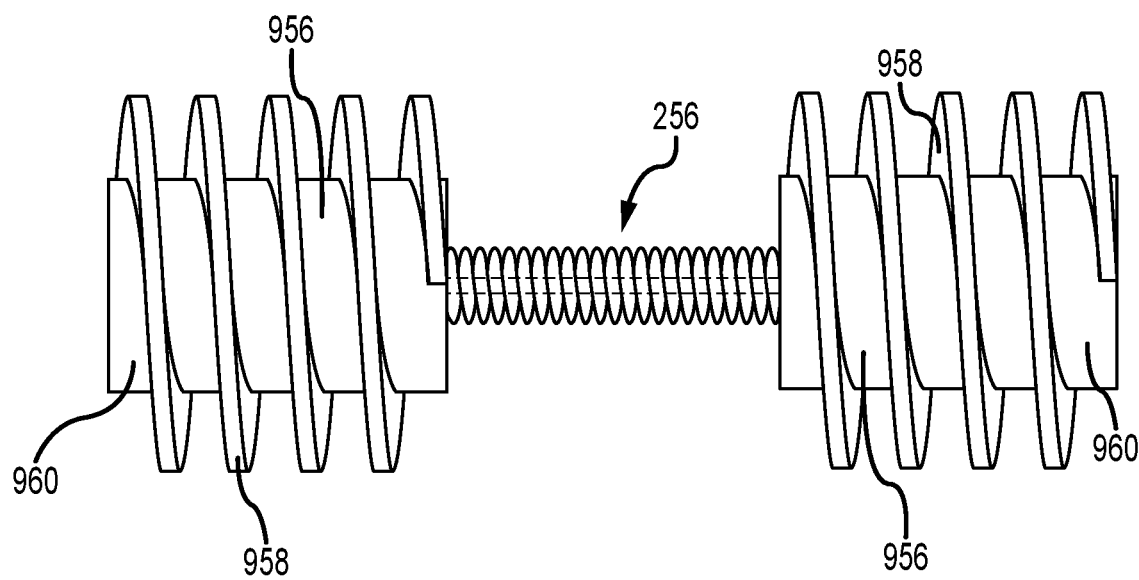
FIG. 77 is a front view of the ionization filter from FIG. 76 with a conductor plate removed from view.

FIGS. 76 and 77 show an alternate embodiment of the ionization filter 950 similar to the embodiment shown in views 74A and 75A, but in which the spiral inserts 960 have the same thread orientations, such as a clockwise thread 958 from the inlet 954 to the central portion and continuing with a clockwise thread 958 from the central portion to the outlet (not shown). Such orientation may help keep the airflow spiral between the emitter 256 and the collector plates 260 for reducing the airflow resistance during breathing.

In both embodiments shown in FIGS. 73A-77, the spiral inserts 960 increase the total minimum distance an electron may potentially travel along a non-conductive surface or through the air between the emitter 256 to the user's body either upstream or downstream from the emitter 256. For example, the minimum distance or shortest distance along one or more surfaces from the central portion to the inlet is along the interface of the inwardly facing surface of the thread 958 and the tubular sidewall 956. Accordingly, the minimal distance is a function of the radius of the tubular sidewall 956, the thread pitch, and number of revolutions. In some embodiments, the total minimum distance is greater than or equal to about 5 cm, greater than or equal to about 10 cm, greater than or equal to about 15 cm, or greater than or equal to about 20 cm. In a preferred embodiment, the minimum distance is greater than or equal to about 22 cm.

Figure 78:
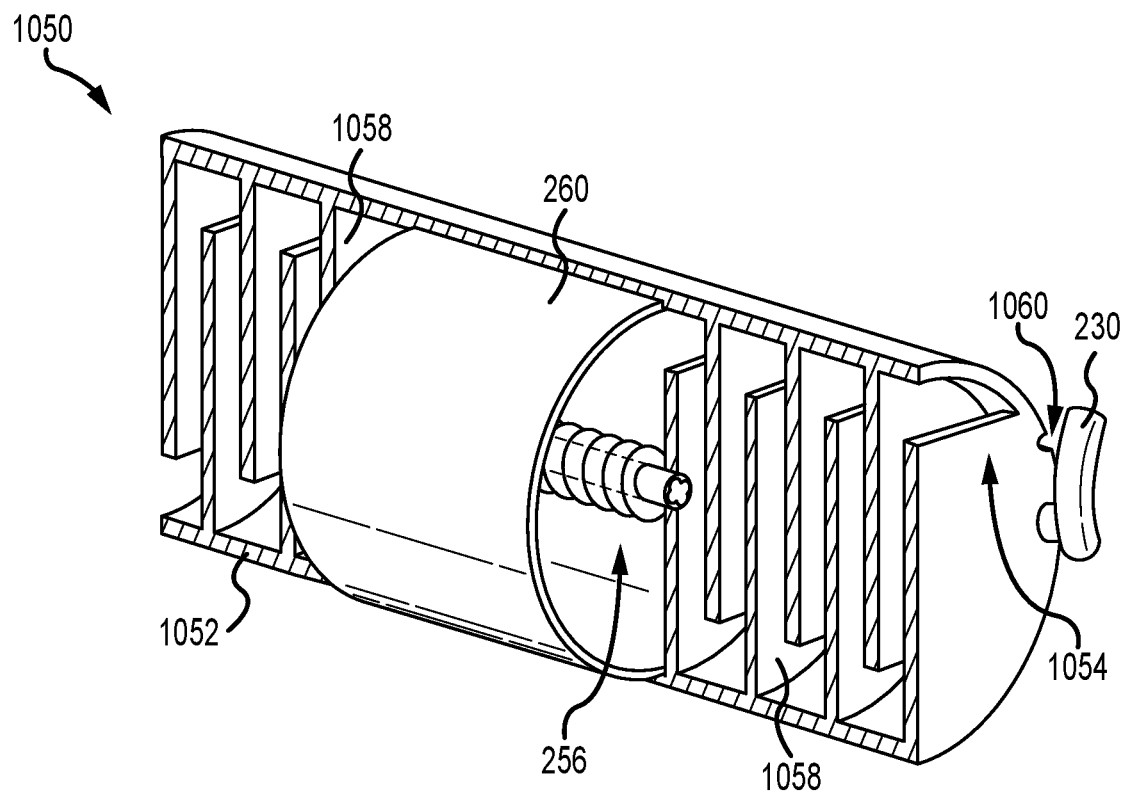
FIG. 78 is a partial sectional, perspective view of another ionization filter configured to be used in an electro-ionic device.
Figure 79A:
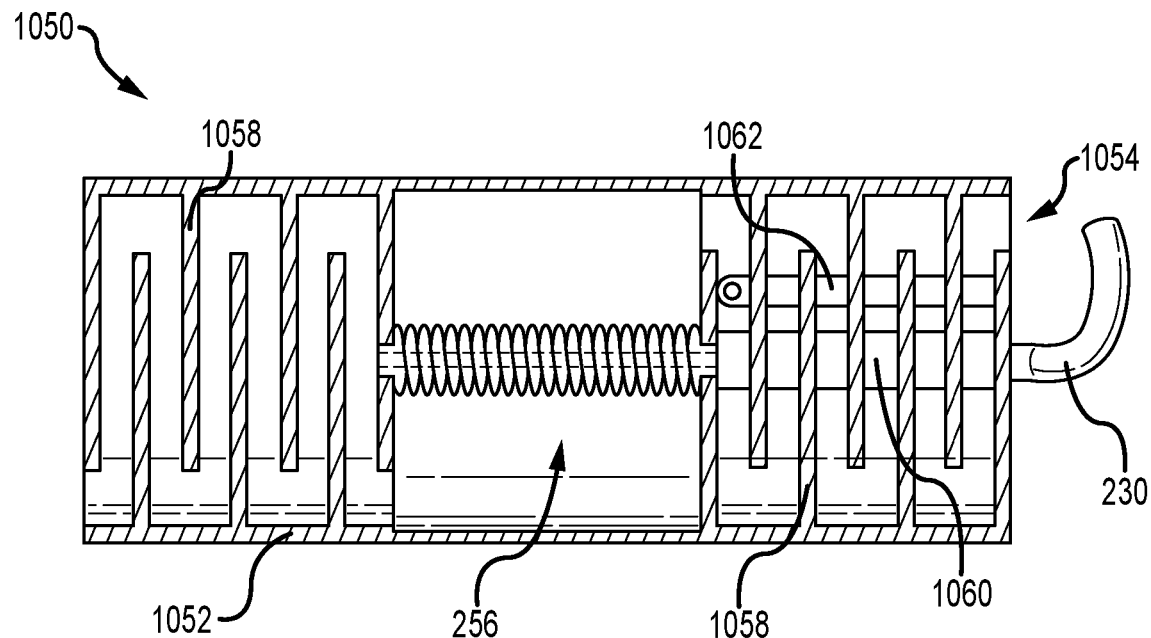
FIG. 79A is a front, sectional view of the ionization filter shown in FIG. 78 with a collector plate removed from view.
Figure 79B:
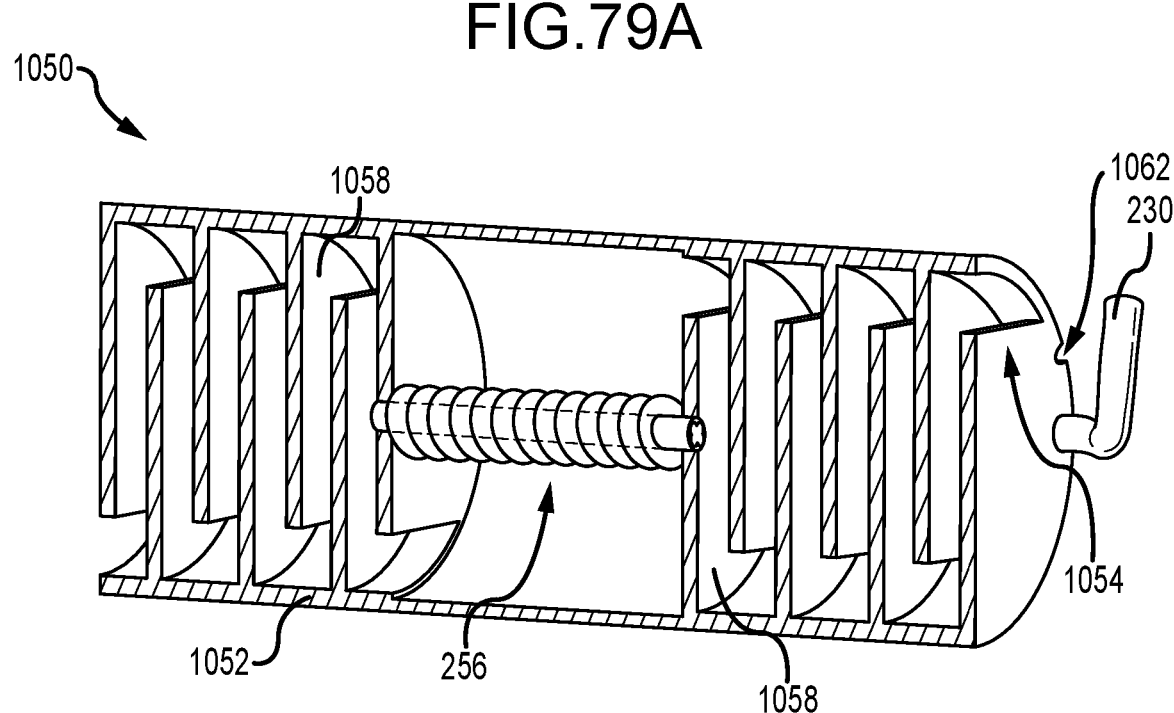
FIG. 79B is a perspective, sectional view of the ionization filter shown in FIG. 79A.

Turning to FIGS. 78-79B, an ionization filter 1050 is shown, which is similar to ionization filter 950. As with the ionization filter 950, the ionization filter includes the emitter 256 and collector plate 260, which operate in substantially the same manner as discussed above. Instead of having a helical airflow pathway, such as the pathway defined by the thread 958 of the spiral inserts 960 in the ionization filter 950, the airflow in the ionization filter 1050 has a radially alternating path that incrementally advances axially from an inlet 1054 to the central portion of an outer housing 1052. In particular, the outer housing 1052 includes an array of integrally formed radial baffles 1058, with each successive baffle 1058 opening at radial opposite sides. This alternating arrangement of the radial baffles 1058 causes the airflow to reverse 180 degrees around each radial baffle 1058 and flow substantially normal to the axial direction of the ionization filter 1050.

As shown in FIG. 79B, the cable 230 travels along the outer housing 1052 in an axially aligned first detent 1060 located at a radial outer position on its circumference away from the openings in the baffles 1058 to minimize its interference with the airflow. The outer housing 1052 may also include a second detent 1062 angularly spaced apart from the detent 1060, and also away from the openings in the baffles 1058. The second detent 1062 may be used to route a conductor from the cable 230 to the collector plate 260, whereas the first detent 1060 may be used to route a conductor that connects to the emitter 256.

The radial baffles 1058 may cause the shortest pathway along a non-conductive surface to zig-zag along the inwardly-facing surface of the outer housing 1052 between the radial baffles 1058. Thus, the minimum is a function of the radius of the outer housing 1052, the shape and width of the openings of the radial baffles 1058, and the number of radial baffles 1058. In some embodiments, the total minimum distance is greater than or equal to about 5 cm, greater than or equal to about 10 cm, greater than or equal to about 15 cm, or greater than or equal to about 20 cm. In a preferred embodiment, the minimum distance is greater than or equal to about 22 cm.

As with the spiral insert 960 between the user and the emitter 256, the radial baffles 1058 may comprise alloys or oxides containing nickel, chromium, manganese, cobalt, iron, copper, platinum, silver, rhodium, cerium or combinations thereof to assist in the decomposition of ozone before the air enters the lungs of the user. In some embodiments, both arrays of radial baffles 1058 may comprise the aforementioned materials.

Figure 80A:
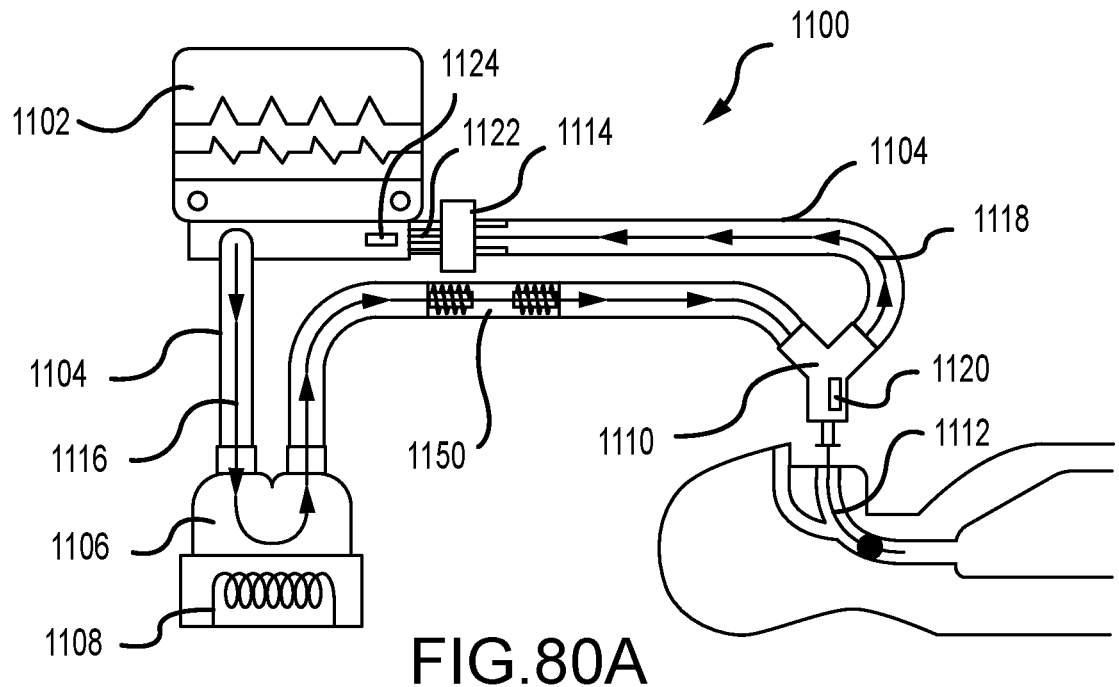
FIG. 80A is a schematic view of an exemplary ventilator system including an ionization filter.

FIG. 80A illustrates an exemplary ventilator system 1100 including a ventilator 1102 configured to assist a patient's breathing by applying positive and negative pressures, during inspiration and expiration, respectively. The ventilator 1102 delivers air (or air with added oxygen) through a network of tubing or channels 1104 along a circuit having an inspiration pathway 1116. After leaving the ventilator 1102, the inspiration pathway 1116 may pass through a humidifier 1106 having a heater 1108 for conditioning the air. In FIG. 80A, the heater 1108 is represented by a heating coil, but one having ordinary skill in the art would recognize that the heater 1108 may include any known heating element or process for transferring heat to the water and/or air in the humidifier. After exiting the humidifier 1106, the inspiration pathway 1116 may pass through an ionization filter 1150 for generating at least ozone and eliminating particles. Similar to the ionization filters 250, 950, and 1050, the ionization filter 1150 includes the emitter 256 and collector plate 260 as discussed above.

Following the ionization filter 1150, the inspiration pathway 1116 continues to a wye 1110 where it intersects an expiration pathway 1118 of the circuit. The wye 1110 may include a pair of check valves configured to prevent inspiration along a portion of the expiration pathway 1118 and expiration along a portion of the inspiration pathway 1116. The inspiration and expiration pathways 1116, 1118 converge along a common exit of the wye 1110 and an entrance to an endotracheal tube 1112 configured to intubate the patient. The tubing 1104 between the ionization filter 1150 and the wye 1110 or the wye 1110 itself may include a first set of one or more sensors 1120 configured to measure the concentration of oxygen and/or ozone and, in some embodiments, air pressure and the flow rate of the air therethrough.

As shown in FIG. 80A, the expiration pathway 1118 returns from the endotracheal tube 1112 to the wye 1110 and back to the ventilator 1102 through a filter 1114 adjacent the ventilator 1102. The filter 1114 may be a porous filter, such as a HEPA filter, or in other embodiments not shown, the filter 1114 may be an ionization filter similar to the ionization filter 1150.

The expiration pathway 1118 may pass through a ozone decomposition device 1122 between the filter 1114 and the ventilator 1102. The ozone decomposition device 1122 may comprise alloys or oxides containing nickel, chromium, manganese, cobalt, iron, copper, platinum, silver, rhodium, cerium, or combinations thereof to assist in the decomposition of ozone before exhausts into the atmosphere.

The ventilator 1102 may include a second set of one or more sensors 1124 configured to measure the concentration of exhausted ozone and in some embodiments the concentration of oxygen and air pressure of the atmosphere. The second set of one or more sensors 1124 may send a signal to the electronics unit representing at least the ozone concentration in the exhaust to ensure that it is maintained below a preterminal concentration, such as less than 0.05 ppm, for example.

Operation of the ventilator system 1100 can be divided into the inspiration and expiration phases of a breath cycle. During the inspiration phase, the ventilator 1102 forces air along the inspiration pathway 1116 into the patient's lungs by applying a positive pressure. As mentioned above, the air may have atmospheric levels of oxygen or it may be infused with oxygen. The air may be conditioned in the humidifier 1106 where it is humidified and warmed (via heater 1108).

Next the humidified air may pass through the ionization filter 1150 where ozone is generated and introduced into the air.

The ionization filter 1150 may be connected to an electronics unit, such as the electronics unit 224 discussed above, to control the voltage and consequently the ozone generated by the ionization filter 1150. The electronics unit may be a dedicated stand-alone unit, or it may be incorporated into the ventilator 1102. The electronics unit may receive a signal from the first set of one or more sensors 1120 representing the concentration of ozone to provide feedback control thereof. In addition, the electronics unit of the ionization filter 1150 may communicate with the ventilator 1102 to allow the ventilator 1102 to control the ionization filter 1150, such as to shut down ozone generation when certain conditions exist. Because some of the diatomic oxygen will ultimately form triatomic oxygen (ozone) during ionization, the density and pressure of the gas may decrease after passing through the ionization filter 1150 and the first set of one or more sensors 1120 may send signals to the ventilator providing information on the oxygen concentration, air pressure, and flow rate to allow feedback control of the oxygen concentration and pressure if so desired. The ozonated and oxygenated air may then be delivered to the patient through the wye 1110 and endotracheal tube 1112.

During the expiration phase, the ventilator 1102 may apply a vacuum to assist in evacuating the air from the patient's lungs. In doing so, the expired air may flow along the expiration pathway 1118 to back to the ventilator 1102 through the filter 1114 and the ozone decomposition device 1122. As discussed above, the filter 1114 may be a porous filter or another ionization filter but optimized to remove particles while minimizing ozone generation.

Figure 80B:
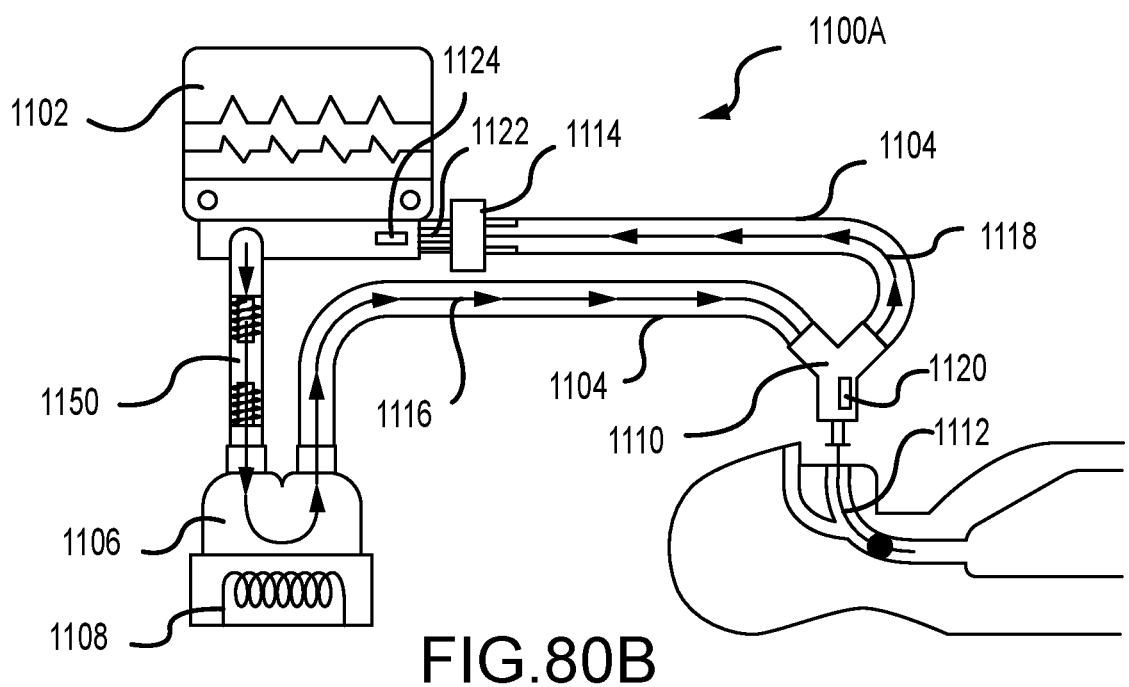
FIG. 80B is a schematic view of an exemplary ventilator system including an ionization filter.

FIG. 80B illustrates an exemplary ventilator system 1100A similar to ventilator system 1100, but the order is reversed for the humidifier 1106 and the ionization filter 1150 along the inspiration pathway 1116. For example, it may be desirable to humidify and warm the air after subjecting it to high voltages in the electrostatic filter 1150.

Figure 81A:
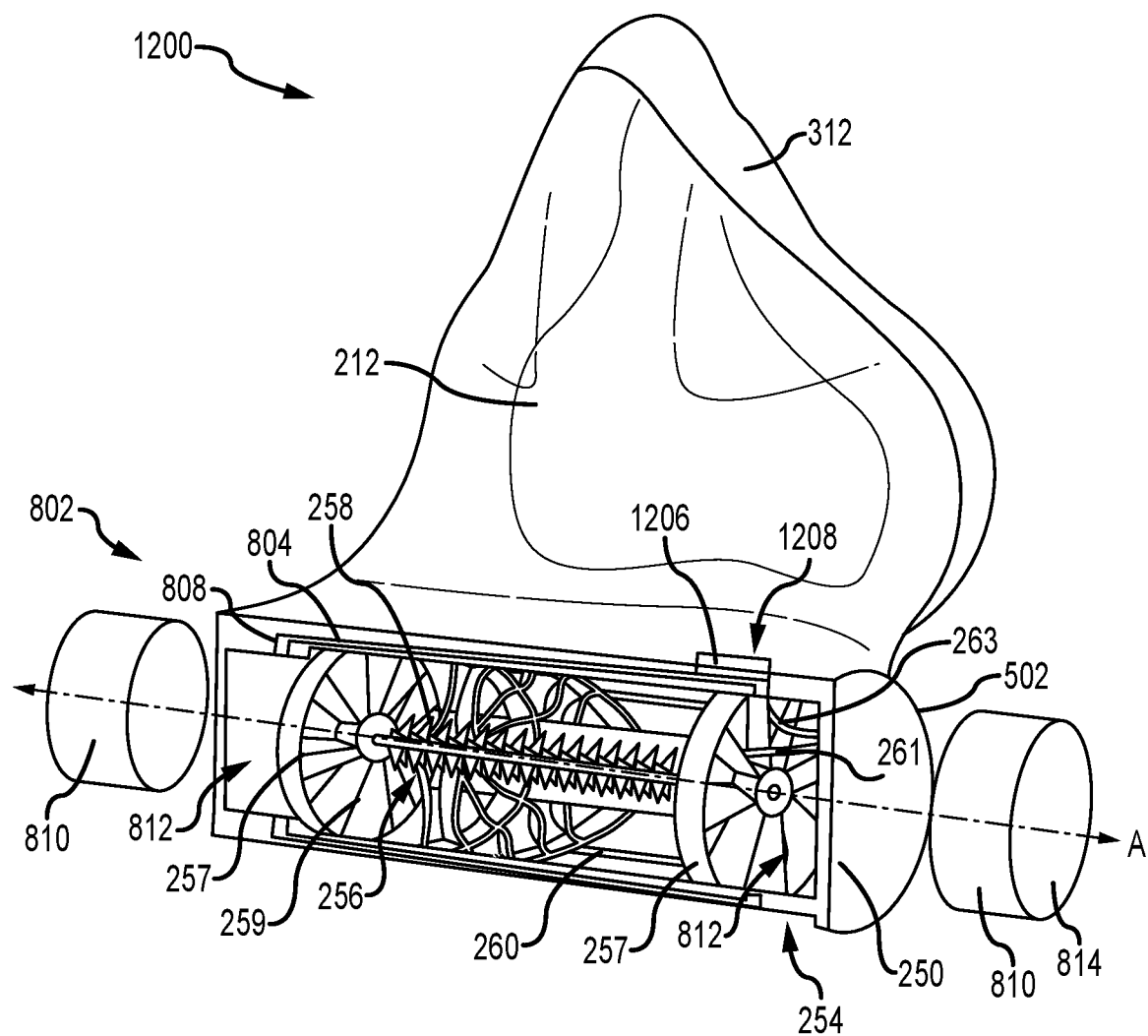
FIG. 81A is a partially exploded perspective view of an exemplary mask assembly configured to be used in an electro-ionic device.
Figure 81B:
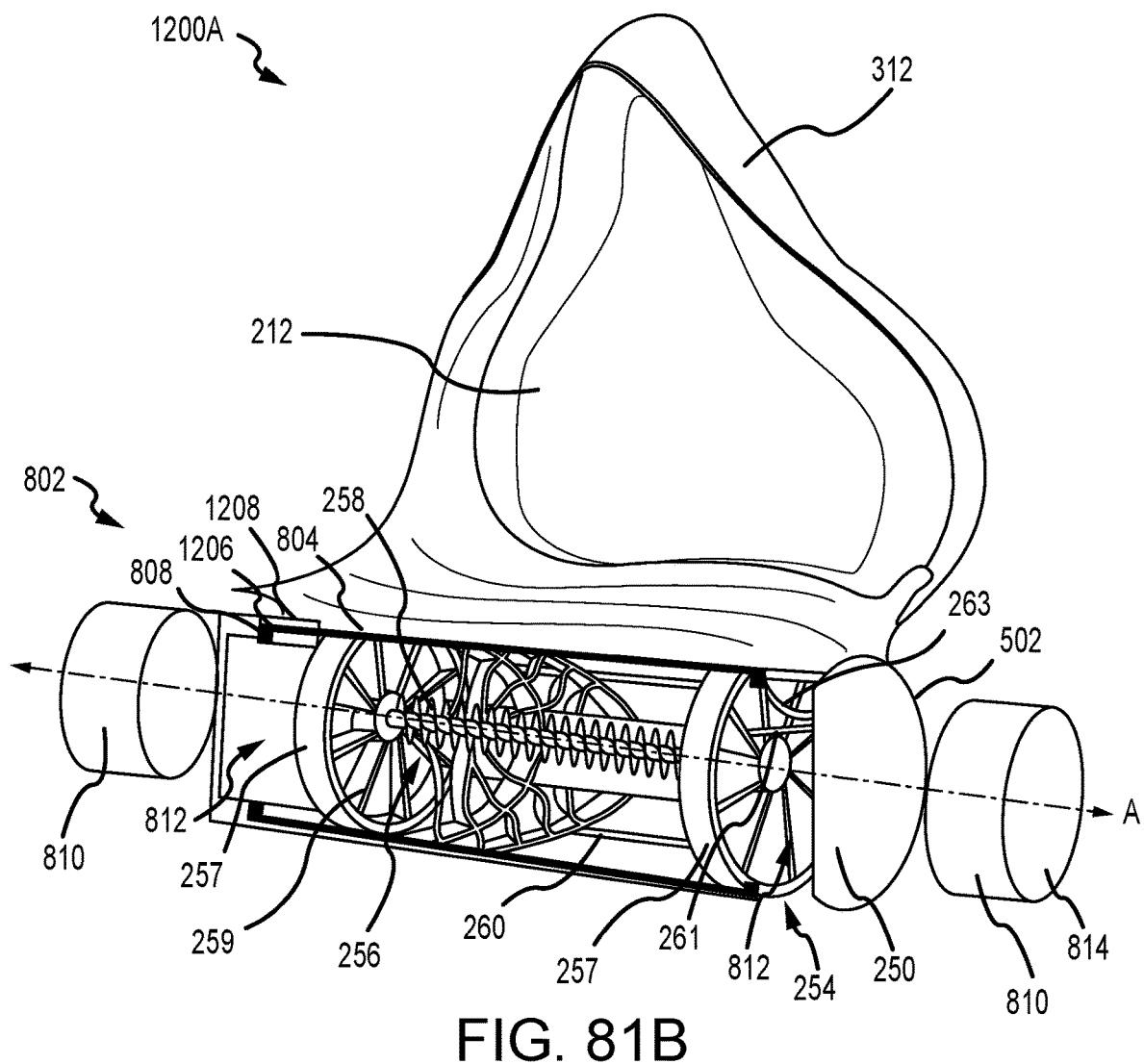
FIG. 81B is a partially exploded perspective view of another exemplary mask assembly configured to be used in an electro-ionic device.

FIGS. 81A and 81B illustrate partially exploded views of other embodiments of a mask assembly 1200 and 1200A and its various components for use in an electro-ionic device 200 in a similar manner as the mask assembly 800 discussed above. The mask assemblies 1200 and 1200A are configured to remove airborne radioactive particles. The mask assembly 800 is similar to mask assembly 500 except for the differences described below.

As shown in FIG. 81A, a radiation detector 1206 may be located on the outside surface of the solid shell 804 of the Faraday cage 802. The Faraday cage 802 may help shield the radiation detector 1206 from any potential electromagnetic interference that may be generated by the high voltage circuitry inside the ionization filter 250. In other embodiments that do not include a Faraday cage 802, the radiation detector 1206 may be located on the outside of the housing of the ionization filter 250. Alternatively shown in FIG. 81B, the radiation detector 1206 may be located inside the Faraday cage 802 and/or the housing of the ionization filter 250, such as adjacent the inwardly facing surface of the solid shell 804 and the inwardly protruding edge 808. With the radiation detector 1206 positioned inside the Faraday cage 802 and/or housing, the radiation detector 1206 may be exposed to the airflow pathway within the housing of the ionization filter 250 where sensitivity to radioactive particles is enhanced.

The radiation detector 1206 may include a display panel 1208 on a top surface thereof (FIG. 81A) or on the outer surface of the housing (FIG. 81B). As shown in FIG. 81B, the display panel 1208 is located on the outer surface of the housing opposite from the radiation detector 1206. In this embodiment, the radiation detector 1206 and the display panel 1208 may be electrically connected to each other via a cable (not shown) routed around the solid shell 804 and the protruding edge 808 of the Faraday cage 802.

Figure 82:
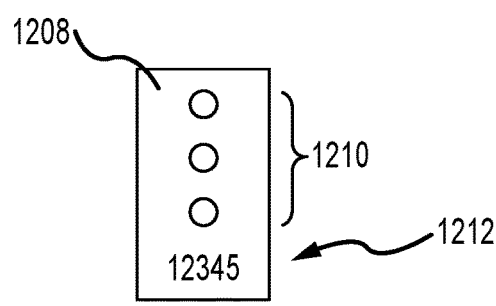
FIG. 82 is a top view of an exemplary radiation display from the mask assembly shown in FIG. 81A.

FIG. 82 illustrates a top view of the display panel 1208 of the radiation detector 1206. The display panel 1208 may include a plurality of indicator lights 1210, such as LEDs, arranged in an array. Each of the indicator lights 1210 may be adjacent indicia such as text or symbols, which may indicate whether power is on or off, radiation is currently being detected, and/or a predetermined level of accumulated radiation has been reached, among other things. For example, the radiation detector 1206 may receive power from the electronics unit 224 (see FIG. 54), therefore, the indicator lights may indicate that the electronics unit 224 and/or the radiation detector 1206 is on. The indicator lights 1210 may indicate that the radiation detector 1206 is currently detecting radiation by, for example, determining a change in the accumulated measured radiation. A plurality of the indicator lights 1210 may be used to indicate the strength of the detected radiation. Although FIG. 82 shows the indicator lights 1210 having three LEDs, in other embodiments, the indicator lights 1210 may have more or less than three LEDs.

The display panel 1208 may also have a numerical display 1212, such as a digital numerical display 1212 shown in FIG. 82. In other embodiments, the display panel 1210 may include more than one numerical display 1212, analog numerical displays, lcd displays, among other types of displays. The numerical display 1212 may indicate the strength of the radiation at any given moment, the cumulated radiation, or the amount of radiation emanating from particles collected in the mask assemblies 1200 and 1200A. Since the mask assemblies 1200 and 1200A are configured to remove radioactive particles passing through the ionization filter 250, doing so could create potential unintended effects of removing radioactive particles from a radioactive environment, and upon leaving that environment, keeping radioactive particles within close proximity to the user's face. Thus, monitoring the radiation emanating from the mask may be useful in determining when to dispose of the collector plate 260 or the mask assemblies 1200 and 1200A.

Figure 61:
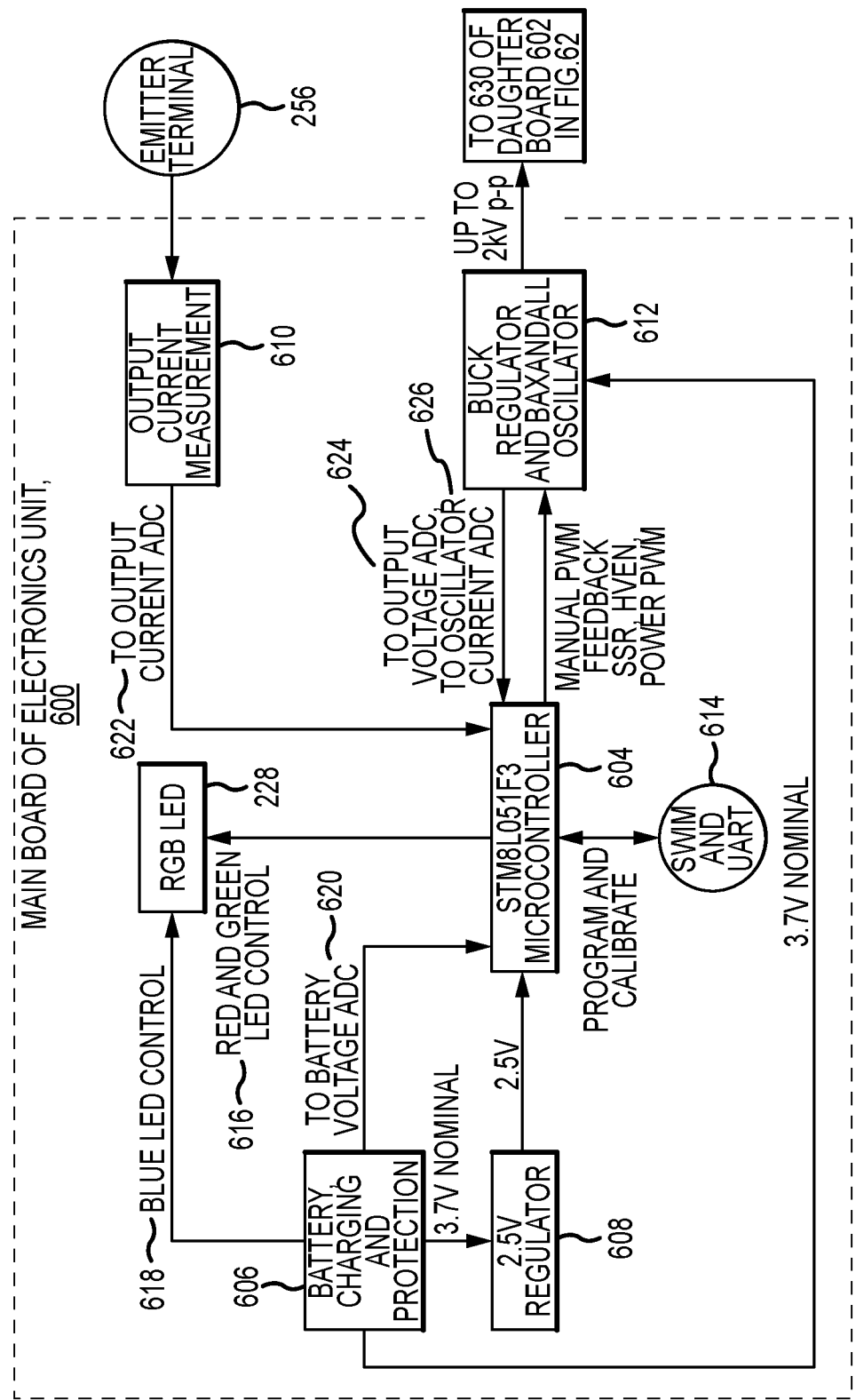
FIG. 61 is a circuit schematic of the main board contained in the electronics unit of any of the embodiments of the electro-ionic device disclosed herein.
Figure 62:
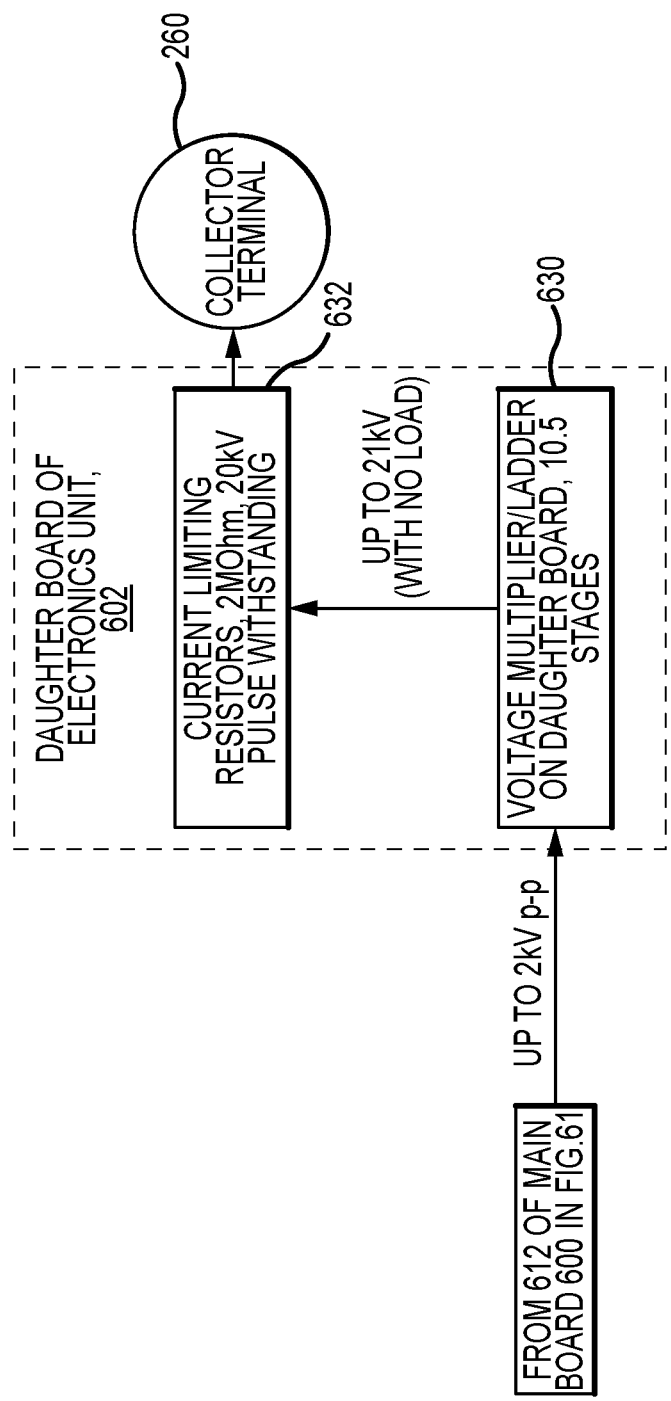
FIG. 62 is a circuit schematic of the daughter board contained in the electronics unit of any of the embodiments of the electro-ionic device disclosed herein, the daughter board being electrically coupled to the main board of FIG. 61.
Figure 64:
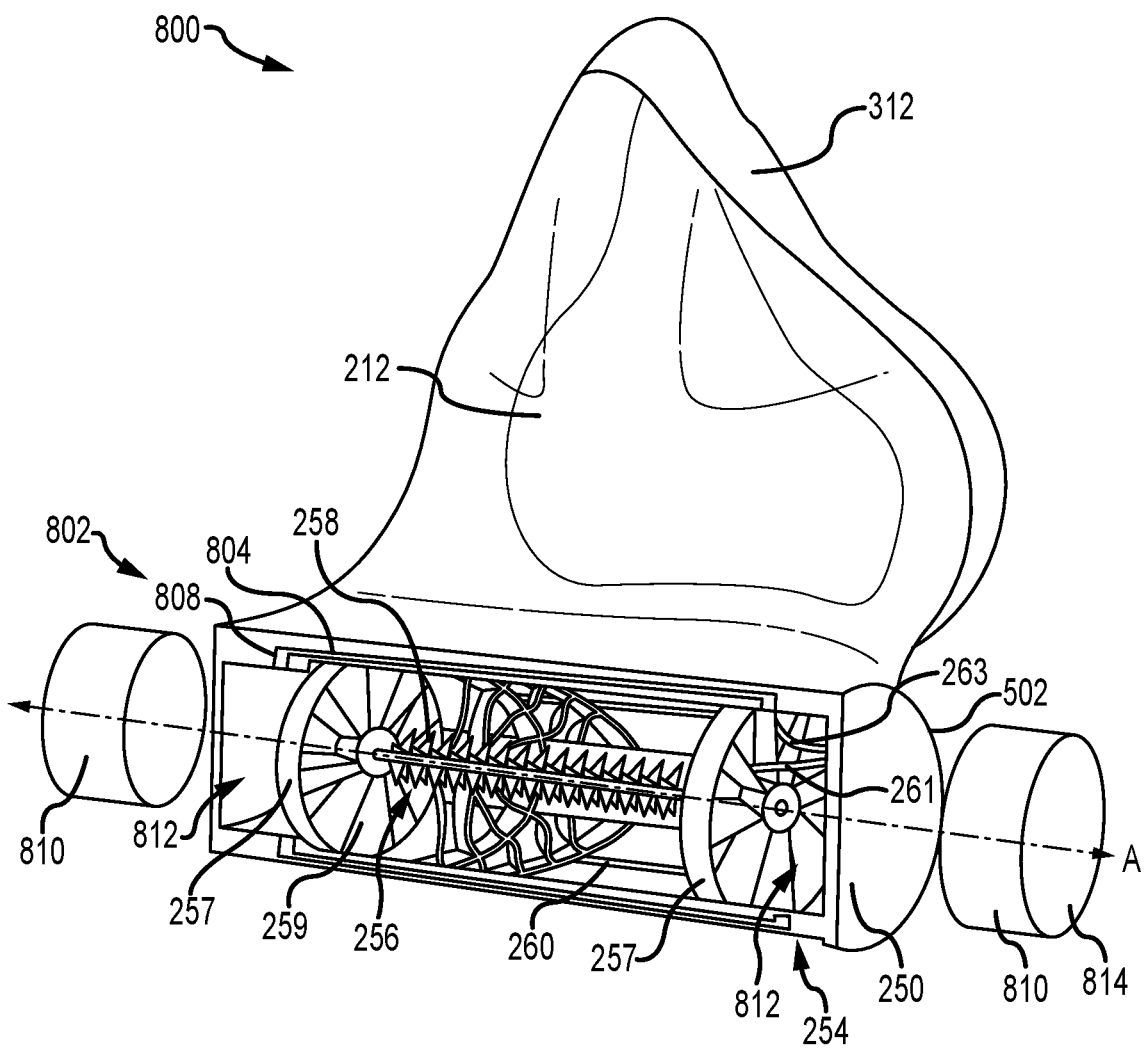
FIG. 64 is a partially exploded perspective view of an exemplary mask assembly configured to be used in an electro-ionic device.
Figure 65:
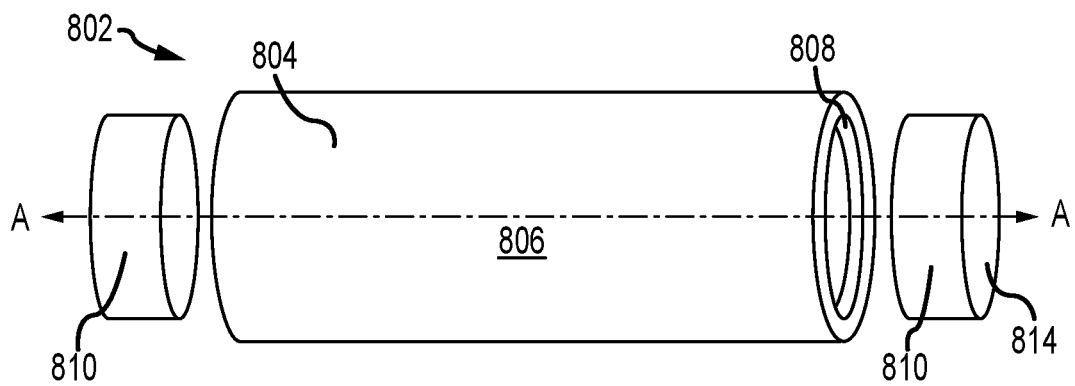
FIG. 65 is a partially exploded perspective view of a Faraday cage from the mask assembly shown in FIG. 64.

FIGS. 61 and 62 are respectively circuit schematics of the main board 600 and the daughter board 602 contained in the electronics unit 224 of any of the above-discussed embodiments of the electro-ionic device 100, 200, 300, 400, and 500, including the device 200 depicted in FIG. 54 or the electro-ionic device 200 including the mask assembly 800 depicted in FIGS. 64 and 65 or the electro-ionic device 500 including the ionization filters 850, 850A, 950, or 1050 depicted in FIGS. 66-79B. As shown in FIG. 61, the main board 600 includes a microcontroller 604, a battery module 606 with charging and protection controls, a 2.5 V regulator 608, an output current measurement module 610, a Buck regulator and Baxandall oscillator module 612, and a SWIM and UART 614.

The microcontroller 604 communicates with the red/blue/green LED (indicator light 228) via a red and green LED control 616, and the battery module 606 communicates with the indicator light 228 via a blue LED control 618. The battery module 606 communicates with the microcontroller 604 via a battery voltage ADC 620. The battery module 606 sends 3.7 V nominal to the 2.5 V regulator 608, which sends 2.5 V to the microcontroller 604. The battery module 606 sends 3.7 V nominal to the Buck regulator and Baxandall oscillator module 612

The microcontroller 604 and SWIM and UART 614 are linked with respect to programming and calibration.

The output current measurement module 610 reads the emitter terminal 256 and reports to the microcontroller 604 via an output current ADC 622. The Buck regulator and Baxandall oscillator module 612 communicates with the microcontroller 604 via an output voltage ADC 624 and an oscillator current ADC 626. The microcontroller 604 communicates with the Buck regulator and Baxandall oscillator module 612 regarding the following microcontroller signals: manual PWM; feedback SSR; HVEN; and power PWM. The Buck regulator and Baxandall oscillator module 612 send up to 2 kV p-p to the voltage multiplier/ladder 630 on the daughter board 602, as continued in FIG. 62.

Still referring to FIG. 61, in one embodiment, manual PWM is two PWM signals used to start the oscillator to build up enough voltage so it can provide feedback for itself to ensure startup with the highly capacitive load. Feedback SSR is a control for a solid-state relay used to allow the manual PWM signals to control the oscillator when off, and then when turned on, to allow the automatic feedback via the transformer after the oscillation is self-sustaining. HVEN is a high voltage enable signal to enable the Buck regulator that powers the oscillator. Finally, power PWM is a single PWM signal to set the desired Buck regulator operating point, and therefore the output power.

As shown in FIG. 62, the daughter board 602 of the electronics unit 224 includes a voltage multiplier/ladder 630 and a current limiting resistors module 632. The voltage multiplier/ladder 630 receives 2 kV p-p from the Buck regulator and Baxandall oscillator module 612 of the main board 600 and sends up to 21 kV (with no load) to the current limiting resistors module 632, which sends to the collector terminal 260. The main board 600 and the daughter board 602 may be contained in a common Faraday cage or separate Faraday cages.

Figure 63:
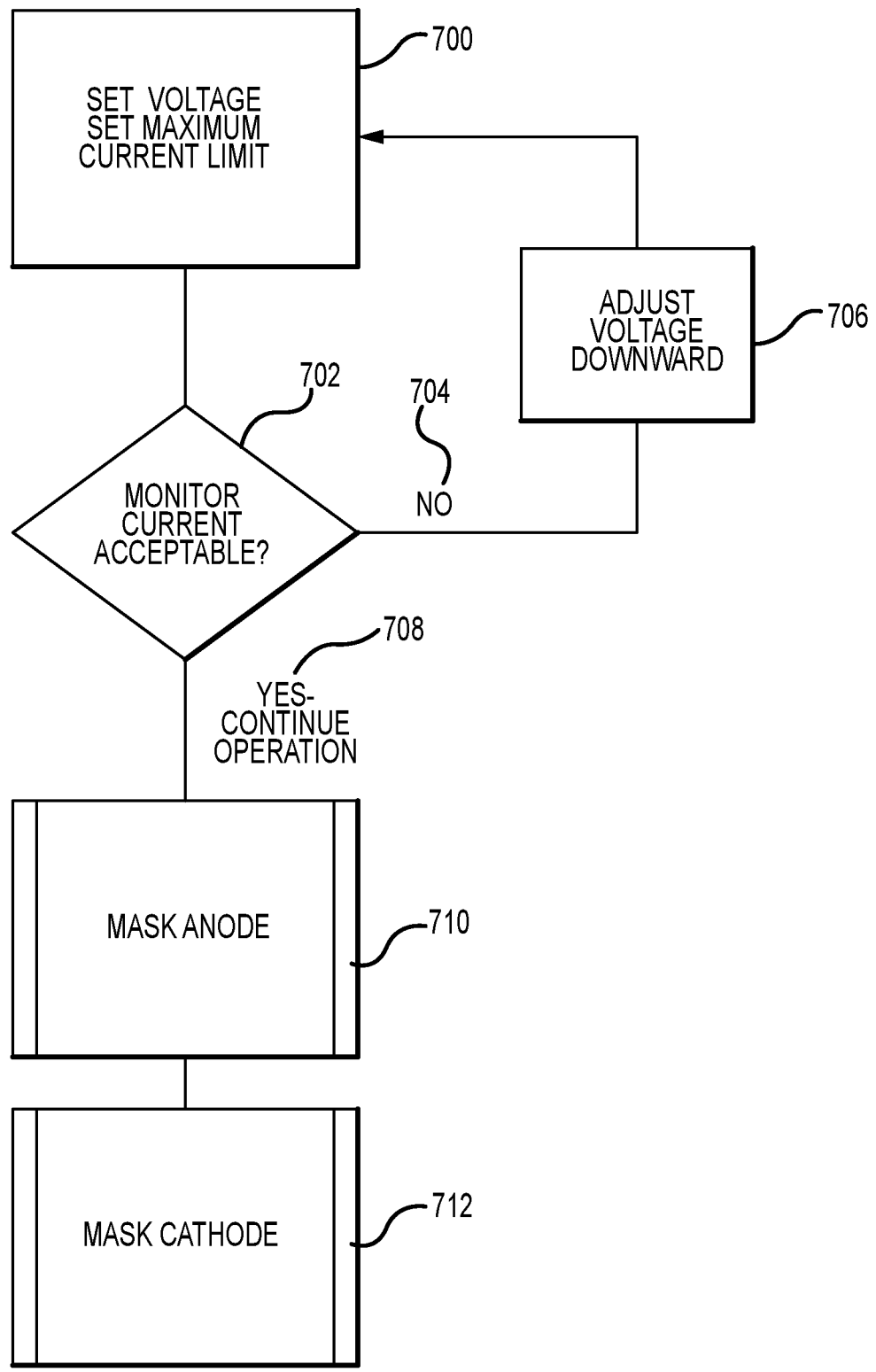
FIG. 63 is a flow chart illustrating voltage modulation for the ionization filter of any of the embodiments of the electro-ionic device disclosed herein.

FIG. 63 is a flow chart illustrating voltage modulation for the ionization filter of any of the embodiments of the electro-ionic device disclosed herein. As illustrated in FIG. 63, voltage and maximum current limit is set (700). The current is monitored to determine if acceptable (702). If current is not acceptable (704), then the voltage is adjusted downward (706). If current is acceptable, then continue operation (708) of the anode (710) and cathode (712) of the ionization filter 250 of the electro-ionic device.

As noted above, emitter/collector offset distance and voltage are variables that affect the performance of the ionization filter, as can the local elevation of where the ionization filter is being used. In calibrating the performance of the ionization filter for the local elevation and the overall situation, the operational point (e.g., operational voltage) can be set where there is effective particle removal in excess of 90% at the same time the ozone generation by the ionization filter remains at low levels. In some embodiments and situations, the optimal operational point may be where the particle reduction is maximized and the ozone generation over time remains below 0.1 parts per million in the inhaled air.

Once the ionization filter is calibrated for the optimal operational point for the local elevation and the overall situation, it may be recalibrated for a new elevation or new situation to again achieve that optimal operational point. This may be done electronically or mechanically. Some embodiments will rely solely on mechanical adjustment, and in doing so, the emitter/collector offset distance and/or geometry of the emitter/collector relationship can be modified/modulated. Mechanical modifications/modulations of the emitter/collector offset distance and/or geometry of the emitter/collector relationship for a new elevation or situation may be able to tune the ionization filter to within 12% to 20% of the former optimal operational point.

Some embodiments will rely solely on electronic recalibration, and in doing so, the voltage and current control can be modified/modulated to recalibrate for a new elevation or situation. Electronic modification/modulations of the voltage and current control may be able to tune the ionization filter to within 10% to 12% of the former optimal operational point.

Some embodiments can employ both mechanical and electronic recalibration. In doing so, the voltage and current control can be modified/modulated via electronics to get another 10% to 12% modification additional to the 12% to 20% provided via the mechanical recalibration.

In some embodiments, calibration and optimization of the performance of the ionization filter may occur at sea level because higher elevation will require lower voltage and should be easier on the electrical components.

It should be understood from the foregoing that, while particular aspects have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A protective device to protect a respiratory system of a wearer from hazards in surrounding ambient air, the protective device comprising:
    an airway having a first end and a second end, the first end configured to receive the surrounding ambient air, the second end interfaceable with the respiratory system of the wearer;
    a collector surrounding at least a portion of the airway;
    at least first and second conductive porous filters, wherein the collector is electrically connected to the first and second conductive porous filters; and
    an emitter extending though at least a portion of the collector, the emitter and the collector collectively forming an ionization filter, wherein the emitter is enclosed by a Faraday cage.

2. The protective device of claim 1, further comprising a mask portion with an interior including a nose region and a mouth region, the second end of the airway including the interior of the mask portion.

3. The protective device of claim 1, further comprising a mask portion with an interior including at least a mouth region, the second end of the airway including the interior of the mask portion.

4. The protective device of claim 3, wherein the airway includes an opening into the interior of the mask portion, and the opening includes a fluid filter configured to reduce an amount of, or prevent, fluids from the wearer entering the ionization filter.

5. The protective device of claim 4, wherein the fluid filter includes at least one of alloys or oxides containing at least one of nickel, chromium, manganese, cobalt, iron, copper, platinum, silver, rhodium, or cerium to assist in decomposition of ozone.

6. The protective device of claim 1, wherein the collector forms at least a portion of the Faraday cage.

7. The protective device of claim 1, wherein the Faraday cage also encloses circuitry within the ionization filter.

8. The protective device of claim 1, wherein the first and second conductive porous filters and the collector collectively form at least a portion of the Faraday cage, the Faraday cage encapsulating the emitter.

9. The protective device of claim 1, wherein the porous filters include a non-conductive fibrous mesh infused with electrically conductive materials, including conductive wires.

10. The protective device of claim 1, wherein the porous filters include a mesh of conductive materials without a non-conductive mesh.

11. The protective device of claim 10, wherein the mesh of conductive materials includes at least one of alloys or oxides containing at least one of nickel, chromium, manganese, cobalt, iron, copper, platinum, silver, rhodium, cerium, or combinations thereof.

12. The protective device of claim 11, wherein the porous filters assist in decomposition of ozone.

13. The protective device of claim 11, wherein the Faraday cage further includes an end cap.

14. The protective device of claim 13, wherein electrically conductive materials used to form the end cap of the Faraday cage include at least one of copper, aluminum, or steel alloys.

15. The protective device of claim 1, wherein the porous filters include an electrically conductive mesh having a pore size of at least one of the following: between 1 μm and 5 mm, between 10 μm and 2.5 mm, between 100 μm and 2.0 mm, or between 1 mm and 2 mm.

16. The protective device of claim 1, wherein first and last electrodes of the emitter are axially spaced farther apart from the first conductive porous filter and the second conductive porous filter, respectively, than their radial distance to the collector.

17. The protective device of claim 1, wherein the collector is a cylindrical collector.

18. A protective device to protect a respiratory system of a wearer from hazards in surrounding ambient air, the protective device comprising:
    an airway having a first end and a second end, the first end configured to receive the surrounding ambient air, the second end interfaceable with the respiratory system of the wearer;
    a collector surrounding at least a portion of the airway; and
    an emitter extending though at least a portion of the collector, the emitter and the collector collectively forming an ionization filter, wherein the emitter is enclosed by a Faraday cage, and wherein the emitter is housed at an axial center of the collector.

19. A protective device to protect a respiratory system of a wearer from hazards in surrounding ambient air, the protective device comprising:
    an airway having a first end and a second end, the first end configured to receive the surrounding ambient air, the second end interfaceable with the respiratory system of the wearer;
    a collector surrounding at least a portion of the airway; and
    an emitter extending though at least a portion of the collector, the emitter and the collector collectively forming an ionization filter, wherein the emitter is enclosed by a Faraday cage, wherein turbulence vanes are located within the airway and confines of the Faraday cage to increase an incidence of particles interfacing with the emitter.

20. The protective device of claim 18 or 19, wherein the emitter is configured to be inserted into, or removed from, the collector along an axial direction for cleaning or replacement.

21. The protective device of claim 18 or 19, wherein the collector defines the portion of the airway.

22. The protective device of claim 21, wherein the airway leading to one or both open ends of the portion of the airway defined by the collector includes a spiral, and the spiral is coated with, or at least partially formed of, at least one alloy or oxide containing at least one of nickel, chromium, manganese, cobalt, iron, copper, platinum, silver, rhodium, or cerium to assist in decomposition of ozone.

23. The protective device of claim 21, wherein the airway leading to one or both open ends of the portion of the airway defined by the collector includes a spiral pathway, and the spiral pathway defines an airflow travel distance along the spiral pathway of at least one of: greater than or equal to 5 cm, greater than or equal to 10 cm, greater than or equal to 15 cm, greater than or equal to 20 cm; or greater than or equal to 22 cm.

24. The protective device of claim 21, wherein the airway leading to one or both open ends of the portion of the airway defined by the collector includes a zigzag pathway formed by opposed and offset radially inward extending baffles.

25. The protective device of claim 21, wherein the airway leading to one or both open ends of the portion of the airway defined by the collector includes a zigzag pathway formed by opposed and offset radially inward extending baffles, and the zigzag pathway is coated with, or at least partially formed of, at least one alloy or oxide containing at least one of nickel, chromium, manganese, cobalt, iron, copper, platinum, silver, rhodium, or cerium to assist in decomposition of ozone.

26. The protective device of claim 21, wherein the airway leading to one or both open ends of the portion of the airway defined by the collector includes a zigzag pathway formed by opposed and offset radially inward extending baffles, and the zigzag pathway defines an airflow travel distance along the zigzag pathway of at least one of: greater than or equal to 5 cm, greater than or equal to 10 cm, greater than or equal to 15 cm, greater than or equal to 20 cm; or greater than or equal to 22 cm.

27. A protective device to protect a respiratory system of a wearer from hazards in surrounding ambient air, the protective device comprising:

an airway having a first end and a second end, the first end configured to receive the surrounding ambient air, the second end interfaceable with the respiratory system of the wearer;

a collector surrounding at least a portion of the airway and defining the portion of the airway; and an emitter extending though at least a portion of the collector, the emitter and the collector collectively forming an ionization filter, wherein the emitter is enclosed by a Faraday cage, wherein the airway leading to one or both open ends of the portion of the airway defined by the collector includes a spiral.

28. The protective device of claim 27, wherein the spiral is in a form of a spiral insert in the ionization filter.

29. The protective device of claim 27, wherein the spiral is in a form of a spiral pathway defined in an outer housing of the ionization filter.

30. The protective device of claim 27, wherein the airway leading to each open end of the portion of the airway respectively defined by the collector includes a spiral, a first spiral being clockwise and a second spiral being counter-clockwise.

* * * * *